(12) United States Patent
Ameriks et al.

(10) Patent No.: US 10,155,769 B2
(45) Date of Patent: Dec. 18, 2018

(54) FUSED AZAHETEROCYCLIC COMPOUNDS AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Brian Ngo Laforteza, San Diego, CA (US); Terry Patrick Lebold, San Diego, CA (US); Suchitra Ravula, San Diego, CA (US); Brad M. Savall, San Diego, CA (US); Brock T. Shireman, Poway, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/790,809

(22) Filed: Oct. 23, 2017

(65) Prior Publication Data

US 2018/0111942 A1    Apr. 26, 2018

Related U.S. Application Data

(60) Provisional application No. 62/412,867, filed on Oct. 26, 2016.

(51) Int. Cl.
*C07D 487/04*    (2006.01)
*C07D 403/14*    (2006.01)
*C07D 417/14*    (2006.01)
*C07D 471/04*    (2006.01)

(52) U.S. Cl.
CPC ......... *C07D 487/04* (2013.01); *C07D 403/14* (2013.01); *C07D 417/14* (2013.01); *C07D 471/04* (2013.01)

(58) Field of Classification Search
CPC .. C07D 487/04; C07D 403/14; C07D 471/04; C07D 417/14
See application file for complete search history.

(56) References Cited

U.S. PATENT DOCUMENTS

2015/0344468 A1    12/2015 Gardinier et al.
2016/0289238 A1*   10/2016 He ....................... C07D 519/00

FOREIGN PATENT DOCUMENTS

WO    WO 2000/001376    1/2000
WO    WO 2008/113795    9/2008

OTHER PUBLICATIONS

Bagshawe, *Drug Dev Res*. 1995, 34, 220-230.
Bertolini, et al., *J Med Chem*. 1997, 40, 2011-2016.
Bodor, *Adv Drug Res*. 1984, 13, 224-331.
Brewer, G. J. (1997). "Isolation and culture of adult rat hippocampal neurons." Journal of Neuroscience Methods 71(2): 143-155.
Chen et al., *Bipolar Disord.*, 13:1-15, 2011.
Cho et al. (2007). "Two families of TARP isoforms that have distinct effects on the kinetic properties of AMPA receptors and synaptic currents." *Neuron* 55(6): 890-904.
Du et al., *J Neurosci* 24: 6578-6589, 2004.
Du et al., *J Neurosci* 28: 68-79, 2008.
Engin and Treit, *Behav Pharmacol* 18:365-374, 2007.
Fleisher et al., *Adv. Drug Delivery Rev*. 1996, 19, 115-130.
G.D. Considine, ed., Van Nostrand's Encyclopedia of Chemistry, p. 261, 5th ed. (2005).
G.S. Paulekuhn, et al., "Trends in Active Pharmaceutical Ingredient Salt Selection based on Analysis of the Orange Book Database", *J. Med. Chem.*, 2007, 50:6665-72.
Gill and Bredt., *Neuropsychopharmacology* 36(1): 362-363 (2011).
Harrison, *Brain* 125:1428-1449, 2002.
Heckers and Konradi, *Curr Top Behav Neurosci*. 4:529-553, 2010.
Lazzaro et al. (2002). "Functional characterization of CP-465,022, a selective, noncompetitive AMPA receptor antagonist." *Neuropharmacology* 42(2): 143-153.
McNaughton et al., *Behav Pharmacol* 18: 329-346, 2007.
Nolen and Bloemkolk, *Neuropsychobiology*, 42 Suppl 1:11-7, 2000.
Pirotte Bi et al, "AMPA receptor positive allosteric modulators: a patent review", Expert Opinion on Therapeutic Patents, Informa Healthcare, GB, vol. 23, No. 5, May 1, 2013 (May 1, 2013), pp. 615-628.
Robinson et al., *J Med Chem*. 1996, 39 (1), 10-18.
Rogawski, Michael A., "Revisiting AMPA Receptors as an AntiEpileptic Drug Target" Epilepsy *Currents* 11.2 (2011).
S.M. Berge, et al., "Pharmaceutical Salts", *J Pharm Sci.*, 1977, 66:1-19.
Schobel et al., *Arch Gen Psych*, 66:938-946, 2009.
Shan, et al., *J Pharm Sci*. 1997, 86 (7), 765-767.
Shi et al (2009) "The stoichiometry of AMPA receptors and TARPs varies by neuronal cell type." *Neuron* 62(5): 633-640.

(Continued)

*Primary Examiner* — Rebecca L Anderson
(74) *Attorney, Agent, or Firm* — Thomas J. Dodd

(57) ABSTRACT

Provided herein are compounds of Formula (I), and pharmaceutically acceptable salts, N-oxides, or solvates thereof,

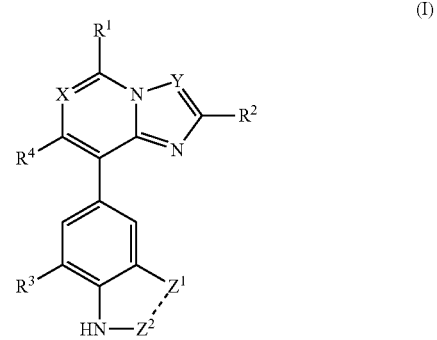

Also provided herein are pharmaceutical compositions comprising compounds of Formula (I) and methods of using compounds of Formula (I).

26 Claims, No Drawings

(56) References Cited

OTHER PUBLICATIONS

Simon et al., "Positive modulators of the AMPA receptor", Expert Opinion on Therapeutic Patents., vol. 10, No. 10, Oct. 1, 2000 (Oct. 1, 2000), pp. 1539-1548.
Small et al, *Nat. Rev. Neurosci.* 12:585-601, 2011.
Strange et al. (2006). "Functional characterisation of homomeric ionotropic glutamate receptors GluR1-GluR6 in a fluorescence-based high throughput screening assay." *Comb Chem High Throughput Screen* 9(2): 147-158.
Tomita et al. (2003). "Functional studies and distribution define a family of transmembrane AMPA receptor regulatory proteins." *J Cell Biol* 161(4): 805-816.
Tregellas et al.,*Am J Psychiatry* 171: 549-556, 2014.
Yeung et al., *Hippocampus* 23:278-286, 2013.
Yeung et al., *Neuropharmacology* 62: 155-160, 2012.
International Search Report for PCT/US2017/057564 dated Feb. 28, 2018.

\* cited by examiner

FUSED AZAHETEROCYCLIC COMPOUNDS AND THEIR USE AS AMPA RECEPTOR MODULATORS

CROSS-REFERENCED TO RELATED APPLICATIONS

This application claims priority from U.S. Application No. 62/412,867, filed on Oct. 26, 2016, which is incorporated herein by reference.

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., *Neuropsychopharmacology* 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anticonvulsant activity are close to or overlap with doses at which undesired effects are observed. (Michael A. Rogawski. "Revisiting AMPA Receptors as an AntiEpileptic Drug Target" Epilepsy *Currents* 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects, Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, *Nat. Rev. Neurosci.* 12:585-601, 2011). A meta-analysis of post-mortem neuro-pathology studies suggests that hippocampal volume is reduced in volume in patients with mood disorders (Harrison, *Brain* 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., *Bipolar Disord.*, 13:1-15, 2011). Chronic treatment with mood stabilizers such as lithium or valproate reduced AMPA receptor surface expression in hippocampus (Du et al., *J Neurosci* 28: 68-79, 2008). Tricyclic antidepressants can trigger mania in bipolar patients (Nolen and Bloemkolk, *Neuropsychobiology*, 42 Suppl 1:11-7, 2000); these treatments can increase AMPA receptor surface expression in hippocampus (Du et al., *J Neurosci* 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of $GABA_A$ agonists is sufficient to replicate their anxiolytic effects (Engin and Treit, *Behav Pharmacol* 18:365-374, 2007). Traditional anxiolytics with a variety of mechanisms-of-action, including $GABA_A$-receptor antagonists, $5\text{-}HT_{1A}$ receptor antagonists, and SSRIs, suppress brainstem-stimulated theta rhythm within hippocampus (McNaughton et al., *Behav Pharmacol* 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., *Hippocampus* 23:278-286, 2013). Intrahippocampal administration of phenytoin, a voltage-gated sodium channel inhibitor and anticonvulsant, showed similar effects on brainstem-stimulated theta rhythm frequency in anesthetized rat and was anxiolytic in conscious rat (Yeung et al., *Neuropharmacology* 62: 155-160, 2012).

Hippocampal overactivity has been observed in patients suffering from schizophrenia (Heckers and Konradi, *Curr Top Behav Neurosci.* 4:529-553, 2010). The degree of hyperactivity was be positively correlated to the severity of the symptoms (Tregellas et al., *Am J Psychiatry* 171: 549-556, 2014). Hypermetabolism in hippocampus (esp. CA1 region) correlates with disease progression in at-risk individuals, and with disease severity in patients diagnosed with schizophrenia (Schobel et al., *Arch Gen Psych,* 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, *Curr Top Behav Neurosci,* 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alia, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

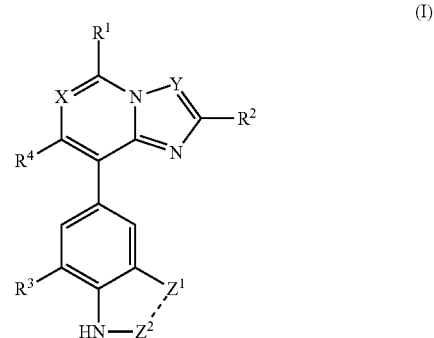

wherein
X is N or CH;
Y is selected from the group consisting of: N, CH, CF, and CCl;
$R^1$ is selected from the group consisting of: H, halo, and $CH_3$;

R² is selected from the group consisting of: $C_{1-6}$alkyl, $C_{1-6}$haloalkyl, $C_{1-6}$alkoxy, $C_{3-8}$cycloalkyl, and phenyl;

R³ is selected from the group consisting of: H, halo, $CH_3$, and $CF_3$;

R⁴ is selected from the group consisting of: $C_{1-6}$alkyl, $C_{1-6}$haloalkyl, $C_{1-6}$alkoxy, phenyl substituted with F, and pyridyl; and

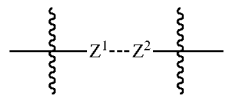

is selected from the group consisting of: —CH=N—, —CF=N—, —CH₂—C(=O)—, and —S—C(=O)—; and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with ¹⁴C), reaction kinetic studies (with, for example ²H or ³H), detection or imaging techniques [such as positron emission tomography (PET) or single-photon emission computed tomography (SPECT)] including drug or substrate tissue distribution assays, or in radioactive treatment of patients. For example, an ¹⁸F or ¹¹C labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

In another aspect provided herein are compounds of Formula (IA), Formula (IB), or Formula (IC) as well as pharmaceutically acceptable salts, N-oxides or solvates of compounds of Formula (IA), pharmaceutically acceptable prodrugs of compounds of Formula (IA), Formula (IB), or Formula (IC), and pharmaceutically active metabolites of Formula (IA), Formula (IB), or Formula (IC).

In a further aspect, provided herein are pharmaceutical compositions, comprising an effective amount of a compound of Formula (IA), Formula (IB), or Formula (IC), as well as pharmaceutically acceptable salts, N-oxides or solvates of compounds of Formula (IA), Formula (IB), or Formula (IC), pharmaceutically acceptable prodrugs of compounds of Formula (IA), Formula (IB), or Formula (IC), and pharmaceutically active metabolites of Formula (IA), Formula (IB), or Formula (IC).

In a further aspect, provided herein are compounds of Formula (IA), Formula (IB), or Formula (IC), as well as pharmaceutically acceptable salts, N-oxides or solvates of compounds of Formula (IA), Formula (IB), or Formula (IC), pharmaceutically acceptable prodrugs of compounds of Formula (IA), Formula (TB), or Formula (IC), and pharmaceutically active metabolites of Formula (IA), Formula (TB), or Formula (IC), for the treatment of any condition described herein.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

In one aspect, provided herein are compounds of Formula (I), and pharmaceutically acceptable salts, N-oxides, or solvates thereof,

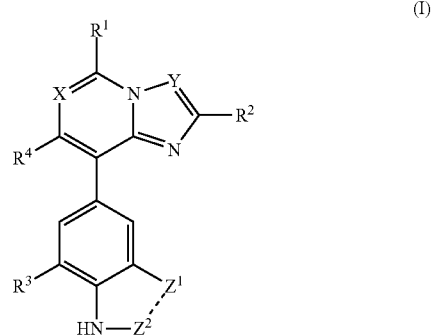

wherein
X is N or CH;
Y is selected from the group consisting of: N, CH, CF, and CCl;

$R^1$ is selected from the group consisting of: H, halo, and $CH_3$;

$R^2$ is selected from the group consisting of: $C_{1-6}$alkyl, $C_{1-6}$haloalkyl, $C_{1-6}$alkoxy, $C_{3-8}$cycloalkyl, and phenyl;

$R^3$ is selected from the group consisting of: H, halo, $CH_3$, and $CF_3$;

$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

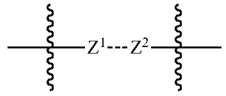

is selected from the group consisting of: —CH=N—; —CF=N—; —CH$_2$—C(=O)—; and —S—C(=O)—.

An additional embodiment of the invention is a compound of Formula (I) wherein X is N.

An additional embodiment of the invention is a compound of Formula (I) wherein X is CH.

An additional embodiment of the invention is a compound of Formula (I) wherein Y is N.

An additional embodiment of the invention is a compound of Formula (I) wherein Y is CH, CF, or Cl.

An additional embodiment of the invention is a compound of Formula (I) wherein Y is CH.

An additional embodiment of the invention is a compound of Formula (I) wherein $R^1$ is H.

An additional embodiment of the invention is a compound of Formula (I) wherein $R^1$ is $CH_3$.

An additional embodiment of the invention is a compound of Formula (I) wherein $R^2$ is $C_{1-6}$alkyl, $C_{1-6}$haloalkyl, $CH_2OCH_3$, cyclopropyl, cyclobutyl, cyclopentyl, or phenyl.

An additional embodiment of the invention is a compound of Formula (I) wherein $R^2$ is $CH_3$, $CH_2CH_3$, $CH(CH_3)_2$, $C(CH_3)_3$, $CF_2H$, $CF_3$.

An additional embodiment of the invention is a compound of Formula (I) wherein $R^2$ is $CF_3$.

An additional embodiment of the invention is a compound of Formula (I) wherein $R^3$ is H, F, Cl, or $CH_3$.

An additional embodiment of the invention is a compound of Formula (I) wherein $R^4$ is $C_{1-6}$alkyl, $C_{1-6}$haloalkyl, Cl, CN, $OCH_3$, phenyl substituted with F, cyclopropyl, cyclopentyl, azetidinyl, and azetidinyl substituted with F.

An additional embodiment of the invention is a compound of Formula (I) wherein $R^4$ is $CF_3$.

An additional embodiment of the invention is a compound of Formula (I) wherein

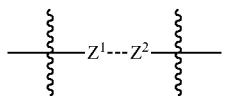

is —CH=N—.

An additional embodiment of the invention is a compound of Formula (I) wherein

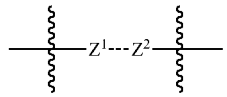

is $CH_2$—C(=O)—.

An additional embodiment of the invention is a compound of Formula (I) having the Formula (IA):

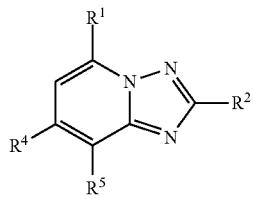

(IA)

wherein $R^1$ is H;

$R^2$ is selected from the group consisting of:
$C_{1-6}$alkyl, $C_{1-6}$haloalkyl, $CH_2OCH_3$, and $C_{3-8}$cycloalkyl;

$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and $R^5$ is selected from the group consisting of:

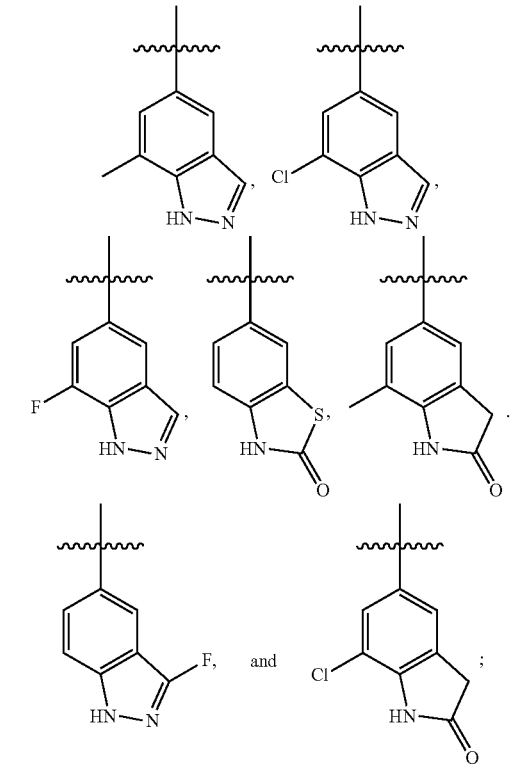

and pharmaceutically acceptable salts, N-oxides or solvates of compounds of Formula (IA).

An additional embodiment of the invention is a compound of Formula (I) having the Formula (IA) wherein $R^2$ is $C_{1-6}$alkyl, $C_{1-6}$haloalkyl, cyclopropyl, cyclobutyl, or cyclopentyl.

An additional embodiment of the invention is a compound of Formula (I) having the Formula (IA) wherein $R^4$ is $CF_3$.

An additional embodiment of the invention is a compound of Formula (I) having the Formula (IA) wherein $R^5$ is

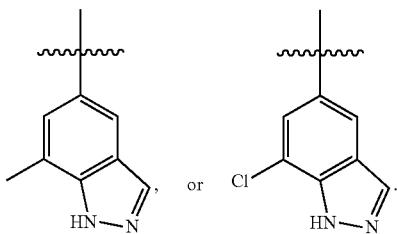 [SMILES: *c1cc(C)c2[nH]ncc2c1 ; *c1cc(Cl)c2[nH]ncc2c1]

An additional embodiment of the invention is a compound of Formula (I) having the Formula (IA) wherein $R^5$ is

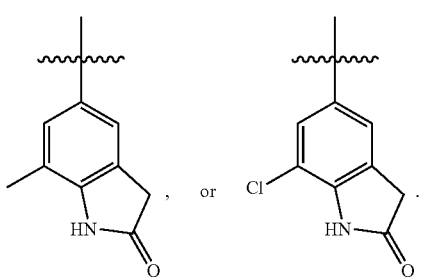 [SMILES: *c1cc(C)c2c(c1)CC(=O)N2 ; *c1cc(Cl)c2c(c1)CC(=O)N2]

An additional embodiment of the invention is a compound of Formula (I) having the Formula (IB):

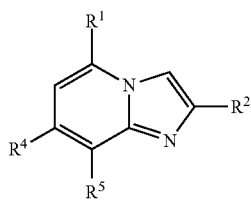

(IB)

wherein $R^1$ is H;

$R^2$ is selected from the group consisting of: $C_{1-6}$alkyl, $C_{1-6}$haloalkyl, $CH_2OCH_3$, $C_{3-8}$cycloalkyl and phenyl;

$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and $R^5$ is selected from the group consisting of:

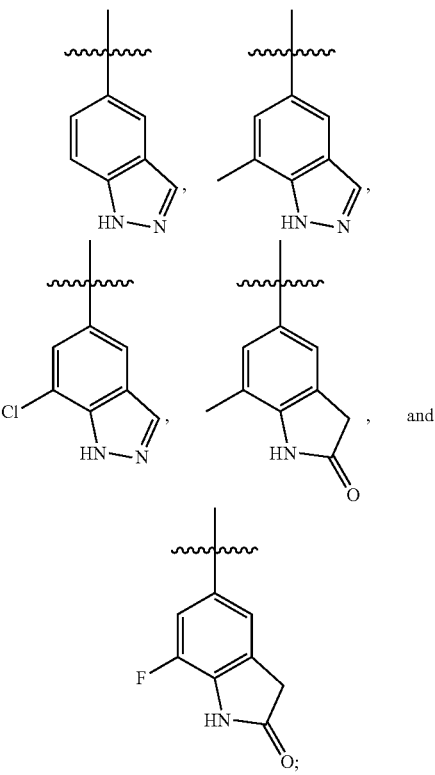

and pharmaceutically acceptable salts, N-oxides or solvates of compounds of Formula (IB).

An additional embodiment of the invention is a compound of Formula (I) having the Formula (IB) wherein $R^2$ is $CF_3$.

An additional embodiment of the invention is a compound of Formula (I) having the Formula (IB) wherein $R^4$ is $CF_3$ or $CH_3$.

An additional embodiment of the invention is a compound of Formula (I) having the Formula (IB) wherein $R^5$ is

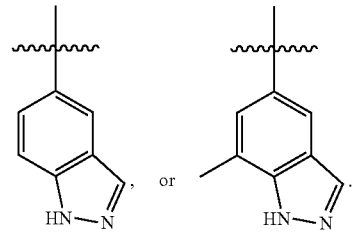 [SMILES: *c1ccc2[nH]ncc2c1 ; *c1cc(C)c2[nH]ncc2c1]

An additional embodiment of the invention is a compound of Formula (I) having the Formula (IC):

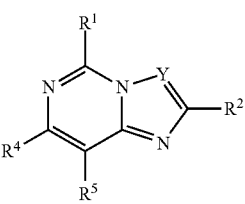

(IC)

wherein
Y is selected from the group consisting of: CH, CF, and CCl;
R$^1$ is H or CH$_3$;
R$^2$ is selected from the group consisting of: C$_{1-6}$alkyl, C$_{1-6}$haloalkyl, CH$_2$OCH$_3$, C$_{3-8}$cycloalkyl and phenyl;
R$^4$ is selected from the group consisting of: halo, C$_{1-6}$alkyl, C$_{1-6}$alkoxy, C$_{1-6}$haloalkyl, CN, C$_{3-8}$cycloalkyl, azetidinyl, azetidinyl substituted with F, and phenyl substituted with F; and
R$^5$ is selected from the group consisting of:

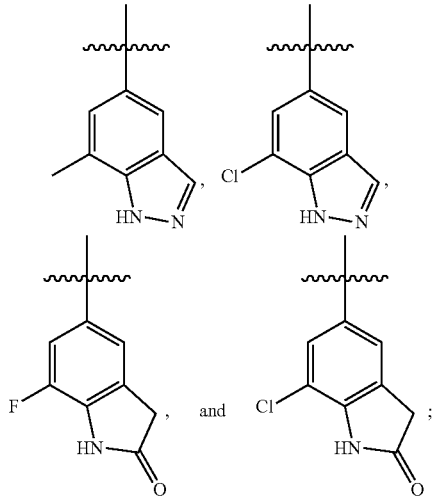

and pharmaceutically acceptable salts, N-oxides or solvates of compounds of Formula (IC).

An additional embodiment of the invention is a compound of Formula (I) having the Formula (IC) wherein R$^1$ is H.

An additional embodiment of the invention is a compound of Formula (I) having the Formula (IC) wherein R$^2$ is C$_{1-6}$haloalkyl.

An additional embodiment of the invention is a compound of Formula (I) having the Formula (IC) wherein R$^4$ is C$_{1-6}$alkyl, CF$_3$, or cyclopropyl.

An additional embodiment of the invention is a compound of Formula (I) having the Formula (IC) wherein R$^5$ is

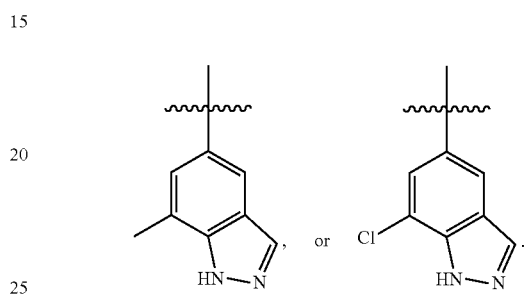

An additional embodiment of the invention is a compound selected from the group consisting of compounds of Formula (I), Formula (IA), Formula (IB), or Formula (IC), or a combination thereof.

A further embodiment of the current invention is a compound as shown below in Table 1.

| Ex # | Compound Name |
|---|---|
| 1 | 8-(7-Chloro-1H-indazol-5-yl)-2-(difluoromethyl)-7-(trifluoromethyl)-[1,2,4]triazolo[1,5-a]pyridine; |
| 2 | 7-Chloro-8-(7-methyl-1H-indazol-5-yl)-2-(trifluoromethyl)-[1,2,4]triazolo[1,5-a]pyridine; |
| 3 | 6-(2,7-Bis(trifluoromethyl)-[1,2,4]triazolo[1,5-a]pyridin-8-yl)benzo[d]thiazol-2(3H)-one; |
| 4 | 2-Cyclobutyl-7-(4-fluorophenyl)-8-(7-methyl-1H-indazol-5-yl)-[1,2,4]triazolo[1,5-a]pyridine; |
| 5 | 6-(7-(4-Fluorophenyl)-2-(trifluoromethyl)-[1,2,4]triazolo[1,5-a]pyridin-8-yl)benzo[d]thiazol-2(3H)-one; |
| 6 | 7-Cyclopentyl-8-(7-methyl-1H-indazol-5-yl)-2-(trifluoromethyl)-[1,2,4]triazolo[1,5-a]pyridine; |
| 7 | 7-(Azetidin-1-yl)-8-(7-methyl-1H-indazol-5-yl)-2-(trifluoromethyl)-[1,2,4]triazolo[1,5-a]pyridine; |
| 8 | 7-(3-Fluoroazetidin-1-yl)-8-(7-methyl-1H-indazol-5-yl)-2-(trifluoromethyl)-[1,2,4]triazolo[1,5-a]pyridine; |
| 9 | 2-Cyclopentyl-7-(4-fluorophenyl)-8-(7-methyl-1H-indazol-5-yl)-[1,2,4]triazolo[1,5-a]pyridine; |
| 10 | 8-(7-Methyl-1H-indazol-5-yl)-2-(trifluoromethyl)-[1,2,4]triazolo[1,5-a]pyridine-7-carbonitrile; |
| 11 | 7-Methyl-5-[7-methyl-2-(trifluoromethyl)imidazo[1,2-a]pyridin-8-yl]indolin-2-one; |
| 12 | 5-(7-(4-Fluorophenyl)-2-(trifluoromethyl)imidazo[1,2-a]pyridin-8-yl)-1H-indazole; |
| 13 | 8-(7-Chloro-1H-indazol-5-yl)-2,7-bis(trifluoromethyl)imidazo[1,2-c]pyrimidine; |
| 14 | 8-(7-Chloro-1H-indazol-5-yl)-2-(difluoromethyl)-7-(trifluoromethyl)imidazo[1,2-c]pyrimidine; |
| 15 | 2-(Difluoromethyl)-8-(7-methyl-1H-indazol-5-yl)-7-(trifluoromethyl)imidazo[1,2-c]pyrimidine; |
| 16 | 8-(7-Methyl-1H-indazol-5-yl)-2-(difluoromethyl)-7-(trifluoromethyl)-[1,2,4]triazolo[1,5-a]pyridine; |

| Ex # | Compound Name |
|---|---|
| 17 | 7-Chloro-5-(2-(difluoromethyl)-7-(trifluoromethyl)-[1,2,4]triazolo[1,5-a]pyridin-8-yl)indolin-2-one; |
| 18 | 7-Methyl-5-(2-(difluoromethyl)-7-(trifluoromethyl)-[1,2,4]triazolo[1,5-a]pyridin-8-yl)indolin-2-one; |
| 19 | 8-(7-Chloro-1H-indazol-5-yl)-2,7-bis(trifluoromethyl)-[1,2,4]triazolo[1,5-a]pyridine; |
| 20 | 8-(7-Methyl-1H-indazol-5-yl)-2,7-bis(trifluoromethyl)-[1,2,4]triazolo[1,5-a]pyridine; |
| 21 | 5-(2,7-Bis(trifluoromethyl)-[1,2,4]triazolo[1,5-a]pyridin-8-yl)-7-chloroindolin-2-one; |
| 22 | 5-(2,7-Bis(trifluoromethyl)-[1,2,4]triazolo[1,5-a]pyridin-8-yl)-7-methylindolin-2-one; |
| 23 | 8-(7-Chloro-1H-indazol-5-yl)-7-(difluoromethyl)-2-(trifluoromethyl)-[1,2,4]triazolo[1,5-a]pyridine; |
| 24 | 8-(7-Methyl-1H-indazol-5-yl)-7-(difluoromethyl)-2-(trifluoromethyl)-[1,2,4]triazolo[1,5-a]pyridine; |
| 25 | 7-Chloro-5-(7-(difluoromethyl)-2-(trifluoromethyl)-[1,2,4]triazolo[1,5-a]pyridin-8-yl)indolin-2-one; |
| 26 | 7-Methyl-5-(7-(difluoromethyl)-2-(trifluoromethyl)-[1,2,4]triazolo[1,5-a]pyridin-8-yl)indolin-2-one; |
| 27 | 7-Methyl-8-(7-methyl-1H-indazol-5-yl)-2-(trifluoromethyl)-[1,2,4]triazolo[1,5-a]pyridine; |
| 28 | 7-Ethyl-8-(7-methyl-1H-indazol-5-yl)-2-(trifluoromethyl)-[1,2,4]triazolo[1,5-a]pyridine; |
| 29 | 7-Methoxy-8-(7-methyl-1H-indazol-5-yl)-2-(trifluoromethyl)-[1,2,4]triazolo[1,5-a]pyridine; |
| 30 | 8-(7-Chloro-1H-indazol-5-yl)-2-cyclopropyl-7-(trifluoromethyl)-[1,2,4]triazolo[1,5-a]pyridine; |
| 31 | 2-Cyclopropyl-8-(7-methyl-1H-indazol-5-yl)-7-(trifluoromethyl)-[1,2,4]triazolo[1,5-a]pyridine; |
| 32 | 8-(7-Chloro-1H-indazol-5-yl)-2-methyl-7-(trifluoromethyl)-[1,2,4]triazolo[1,5-a]pyridine; |
| 33 | 2-Methyl-8-(7-methyl-1H-indazol-5-yl)-7-(trifluoromethyl)-[1,2,4]triazolo[1,5-a]pyridine; |
| 34 | 8-(7-Chloro-1H-indazol-5-yl)-2-ethyl-7-(trifluoromethyl)-[1,2,4]triazolo[1,5-a]pyridine; |
| 35 | 2-Ethyl-8-(7-methyl-1H-indazol-5-yl)-7-(trifluoromethyl)-[1,2,4]triazolo[1,5-a]pyridine; |
| 36 | 5-[2-Ethyl-7-(trifluoromethyl)-[1,2,4]triazolo[1,5-a]pyridin-8-yl]-7-methyl-indolin-2-one; |
| 37 | 8-(7-Chloro-1H-indazol-5-yl)-2-isopropyl-7-(trifluoromethyl)-[1,2,4]triazolo[1,5-a]pyridine; |
| 38 | 2-Isopropyl-8-(7-methyl-1H-indazol-5-yl)-7-(trifluoromethyl)-[1,2,4]triazolo[1,5-a]pyridine; |
| 39 | 5-[2-Isopropyl-7-(trifluoromethyl)-[1,2,4]triazolo[1,5-a]pyridin-8-yl]-7-methyl-indolin-2-one; |
| 40 | 2-Isopropyl-7-methyl-8-(7-methyl-1H-indazol-5-yl)-[1,2,4]triazolo[1,5-a]pyridine; |
| 41 | 7-Chloro-8-(7-chloro-1H-indazol-5-yl)-2-(trifluoromethyl)-[1,2,4]triazolo[1,5-a]pyridine; |
| 42 | 7-(4-Fluorophenyl)-8-(7-fluoro-1H-indazol-5-yl)-2-(trifluoromethyl)-[1,2,4]triazolo[1,5-a]pyridine; |
| 43 | 7-(4-Fluorophenyl)-8-(7-chloro-1H-indazol-5-yl)-2-(trifluoromethyl)-[1,2,4]triazolo[1,5-a]pyridine; |
| 44 | 7-(4-Fluorophenyl)-8-(7-methyl-1H-indazol-5-yl)-2-(trifluoromethyl)-[1,2,4]triazolo[1,5-a]pyridine; |
| 45 | 8-(3-Fluoro-1H-indazol-5-yl)-7-(4-fluorophenyl)-2-(trifluoromethyl)-[1,2,4]triazolo[1,5-a]pyridine; |
| 46 | 2-(Difluoromethyl)-7-(4-fluorophenyl)-8-(7-methyl-1H-indazol-5-yl)-[1,2,4]triazolo[1,5-a]pyridine; |
| 47 | 7-(4-Fluorophenyl)-2-(methoxymethyl)-8-(7-methyl-1H-indazol-5-yl)-[1,2,4]triazolo[1,5-a]pyridine; |
| 48 | 2-Cyclopropyl-7-(4-fluorophenyl)-8-(7-methyl-1H-indazol-5-yl)-[1,2,4]triazolo[1,5-a]pyridine; |
| 49 | 7-Isopropyl-8-(7-methyl-1H-indazol-5-yl)-2-(trifluoromethyl)-[1,2,4]triazolo[1,5-a]pyridine; |
| 50 | 8-(1H-Indazol-5-yl)-7-methyl-2-(trifluoromethyl)imidazo[1,2-a]pyridine; |
| 51 | 7-Fluoro-5-[7-methyl-2-(trifluoromethyl)imidazo[1,2-a]pyridin-8-yl]indolin-2-one; |
| 52 | 7-Methyl-8-(7-methyl-1H-indazol-5-yl)-2-(trifluoromethyl)imidazo[1,2-a]pyridine; |
| 53 | 2-tert-Butyl-7-methyl-8-(7-methyl-1H-indazol-5-yl)imidazo[1,2-a]pyridine; |
| 54 | 5-(2-tert-Butyl-7-methyl-imidazo[1,2-a]pyridin-8-yl)-7-methyl-indolin-2-one; |
| 55 | 7-Methyl-5-(7-methyl-2-phenyl-imidazo[1,2-a]pyridin-8-yl)indolin-2-one; |
| 56 | 7-Methyl-8-(7-methyl-1H-indazol-5-yl)-2-phenyl-imidazo[1,2-a]pyridine; |
| 57 | 2-Cyclopropyl-7-methyl-8-(7-methyl-1H-indazol-5-yl)imidazo[1,2-a]pyridine; |

| Ex # | Compound Name |
|---|---|
| 58 | 5-[7-Methoxy-2-(trifluoromethyl)imidazo[1,2-a]pyridin-8-yl]-7-methyl-indolin-2-one; |
| 59 | 7-Methoxy-8-(7-methyl-1H-indazol-5-yl)-2-(trifluoromethyl)imidazo[1,2-a]pyridine; |
| 60 | 7-Chloro-8-(7-methyl-1H-indazol-5-yl)-2-(trifluoromethyl)imidazo[1,2-a]pyridine; |
| 61 | 5-(2,7-Bis(trifluoromethyl)imidazo[1,2-a]pyridin-8-yl)-1H-indazole; |
| 62 | 5-(2,7-Bis(trifluoromethyl)imidazo[1,2-a]pyridin-8-yl)-7-methyl-1H-indazole; |
| 63 | 8-(7-Methyl-1H-indazol-5-yl)-2,7-bis(trifluoromethyl)imidazo[1,2-c]pyrimidine; |
| 64 | 8-(7-Chloro-1H-indazol-5-yl)-2-ethyl-7-(trifluoromethyl)imidazo[1,2-c]pyrimidine; |
| 65 | 2-Ethyl-8-(7-methyl-1H-indazol-5-yl)-7-(trifluoromethyl)imidazo[1,2-c]pyrimidine; |
| 66 | 8-(7-Chloro-1H-indazol-5-yl)-2-isopropyl-7-(trifluoromethyl)imidazo[1,2-c]pyrimidine; |
| 67 | 8-(7-Chloro-1H-indazol-5-yl)-2-cyclopropyl-7-(trifluoromethyl)imidazo[1,2-c]pyrimidine; |
| 68 | 2-Cyclopropyl-8-(7-methyl-1H-indazol-5-yl)-7-(trifluoromethyl)imidazo[1,2-c]pyrimidine; |
| 69 | 7-Chloro-5-[2-cyclopropyl-7-(trifluoromethyl)imidazo[1,2-c]pyrimidin-8-yl]indolin-2-one; |
| 70 | 5-[2-Cyclopropyl-7-(trifluoromethyl)imidazo[1,2-c]pyrimidin-8-yl]-7-fluoro-indolin-2-one; |
| 71 | 8-(7-Chloro-1H-indazol-5-yl)-7-isopropyl-2-(trifluoromethyl)imidazo[1,2-c]pyrimidine; |
| 72 | 8-(7-Chloro-1H-indazol-5-yl)-2-(difluoromethyl)-7-isopropyl-imidazo[1,2-c]pyrimidine; |
| 73 | 8-(7-Chloro-1H-indazol-5-yl)-7-ethyl-2-(trifluoromethyl)imidazo[1,2-c]pyrimidine; |
| 74 | 7-Ethyl-8-(7-methyl-1H-indazol-5-yl)-2-(trifluoromethyl)imidazo[1,2-c]pyrimidine; |
| 75 | 8-(7-Chloro-1H-indazol-5-yl)-2-(difluoromethyl)-7-ethyl-imidazo[1,2-c]pyrimidine; |
| 76 | 8-(7-Chloro-1H-indazol-5-yl)-7-methyl-2-(trifluoromethyl)imidazo[1,2-c]pyrimidine; |
| 77 | 8-(7-Chloro-1H-indazol-5-yl)-7-cyclopropyl-2-(trifluoromethyl)imidazo[1,2-c]pyrimidine; |
| 78 | 8-(7-Chloro-1H-indazol-5-yl)-7-cyclopropyl-2-(difluoromethyl)imidazo[1,2-c]pyrimidine; |
| 79 | 8-(7-Chloro-1H-indazol-5-yl)-7-cyclopropyl-5-methyl-2-trifluoromethyl)imidazo[1,2-c]pyrimidine; |
| 80 | 8-(7-Chloro-1H-indazol-5-yl)-7-cyclopropyl-2-(difluoromethyl)-5-methyl-imidazo[1,2-c]pyrimidine; |
| 81 | 3-Chloro-8-(7-chloro-1H-indazol-5-yl)-2-cyclopropyl-7-(trifluoromethyl)imidazo[1,2-c]pyrimidine; |
| 82 | 8-(7-Chloro-1H-indazol-5-yl)-2-cyclopropyl-3-fluoro-7-(trifluoromethyl)imidazo[1,2-c]pyrimidine; |
| 86 | 5-(2,7-Bis(trifluoromethyl)imidazo[1,2-a]pyridin-8-yl)-7-chloroindolin-2-one; |
| 87 | 5-(2,7-Bis(trifluoromethyl)imidazo[1,2-a]pyridin-8-yl)-7-methylindolin-2-one; |
| 88 | 5-(2,7-Bis(trifluoromethyl)imidazo[1,2-a]pyridin-8-yl)-7-chloro-1H-indazole; |
| 89 | 8-(7-Chloro-1H-indazol-5-yl)-2-isopropyl-7-(trifluoromethyl)imidazo[1,2-a]pyridine; |
| 90 | 2-Isopropyl-8-(7-methyl-1H-indazol-5-yl)-7-(trifluoromethyl)imidazo[1,2-a]pyridine; |
| 91 | 2-Cyclopropyl-8-(7-methyl-1H-indazol-5-yl)-7-(trifluoromethyl)imidazo[1,2-a]pyridine; |
| 92 | 2-Ethyl-8-(7-methyl-1H-indazol-5-yl)-7-(trifluoromethyl)imidazo[1,2-a]pyridine; |
| 93 | 2-(Difluoromethyl)-8-(7-methyl-1H-indazol-5-yl)-7-(trifluoromethyl)imidazo[1,2-a]pyridine; and |
| 94 | 2-Methyl-8-(7-methyl-1H-indazol-5-yl)-7-(trifluoromethyl)imidazo[1,2-a]pyridine; and | pharmaceutically acceptable salts, N-oxides, or solvates thereof.

A further embodiment of the current invention is a compound as shown below in Table 2.

TABLE 2

| Ex # | Compound Name |
|---|---|
| 83 | 7-Cyclopropyl-2-(difluoromethyl)-5-methyl-8-(7-(trifluoromethyl)-1H-indazol-5-yl)imidazo[1,2-c]pyrimidine; |
| 84 | 8-(7-Chloro-1H-indazol-5-yl)-7-(difluoromethyl)-2-ethyl-[1,2,4]triazolo[1,5-a]pyridine; and |
| 85 | 8-(7-Chloro-1H-indazol-5-yl)-2-cyclopropyl-7-(difluoromethyl)-[1,2,4]triazolo[1,5-a]pyridine; and | pharmaceutically acceptable salts, N-oxides, or solvates thereof.

An additional embodiment of the invention is a pharmaceutical composition comprising:
(A) an effective amount of at least one compound of Formula (I):

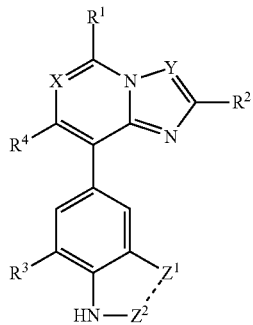

wherein
X is N or CH;
Y is selected from the group consisting of: N, CH, CF, and CCl;
$R^1$ is H or $CH_3$;
$R^2$ is selected from the group consisting of: $C_{1-6}$alkyl, $C_{1-6}$haloalkyl, $CH_2OCH_3$, $C_{3-8}$cycloalkyl, and phenyl;
$R^3$ is selected from the group consisting of: H, halo, $CH_3$, and $CF_3$;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

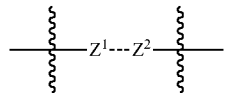

is selected from the group consisting of: —CH=N—; —CF=N—; —CH$_2$—C(=O)—; and —S—C(=O)—; and
pharmaceutically acceptable salts, N-oxides or solvates of compounds of Formula (I); and
(B) at least one pharmaceutically acceptable excipient.

An additional embodiment of the invention is a pharmaceutical composition comprising and effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising and effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising and effective amount of at least one compound of Formula (IC), as well as pharmaceutically acceptable salts, N-oxides or solvates of compounds of Formula (IC), pharmaceutically acceptable prodrugs of compounds of Formula (IC), and pharmaceutically active metabolites of Formula (IC); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are isotopic variations of compounds of Formula (I) as well as Formula (IA), Formula (IB) and Formula (IC), such as, e.g., deuterated compounds of Formula (I) as well as Formula (IA), Formula (TB) and Formula (IC). Also within the scope of the invention are the pharmaceutically acceptable salts, N-oxides or solvates of the isotopic variations of the compounds of Formula (I) as well as well as Formula (IA), Formula (TB) and Formula (IC). Also within the scope of the invention are the pharmaceutically acceptable prodrugs of the isotopic variations of the compounds of Formula (I) as well as Formula (IA), Formula (TB) and Formula (IC), and pharmaceutically active metabolites of the isotopic variations of the compounds of Formula (I) as well as Formula (IA), Formula (TB) and Formula (IC).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

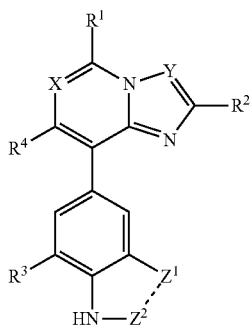

(I)

wherein
X is N or CH;
Y is selected from the group consisting of: N, CH, CF, and CCl;
$R^1$ is H or $CH_3$;
$R^2$ is selected from the group consisting of: $C_{1-6}$alkyl, $C_{1-6}$haloalkyl, $CH_2OCH_3$, $C_{3-8}$cycloalkyl, and phenyl;
$R^3$ is selected from the group consisting of: H, halo, $CH_3$, and $CF_3$;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

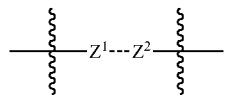

is selected from the group consisting of: —CH=N—; —CF=N—; —CH$_2$—C(=O)—; and —S—C(=O)—; and
pharmaceutically acceptable salts, N-oxides, or solvates thereof, to a subject in need thereof.

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (IA), Formula (IB), or Formula (IC) as well as pharmaceutically acceptable salts, N-oxides or solvates of compounds of Formula (IA), pharmaceutically acceptable prodrugs of compounds of Formula (IA), Formula (IB), or Formula (IC), and pharmaceutically active metabolites of Formula (IA), Formula (IB), or Formula (IC).

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes.

The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_1$-$C_6$alkyl group. In some embodiments, an alkyl group is a $C_1$-$C_4$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$haloalkyl group. In some embodiments, a haloalkyl group is a $C_1$-$C_4$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2Cl$, —$CH_2$—$CF_3$, and the like.

The term "cycloalkyl" refers to monocyclic, non-aromatic hydrocarbon groups having from 3 to 8 carbon atoms. Examples of cycloalkyl groups include, for example, cyclopropyl, cyclobutyl, cyclopentyl, cyclohexyl, and the like.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

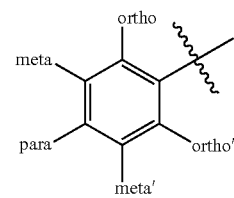

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

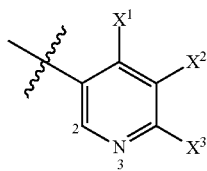

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5$^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

A wavy line "〜〜" indicates the point of attachment to the rest of the molecule.

Additionally, any formula given herein is intended to refer also to hydrates, solvates, and polymorphs of such compounds, and mixtures thereof, even if such forms are not listed explicitly.

Certain compounds of Formula (I) (as well as Formulas (IA), (IB), and (IC)), or pharmaceutically acceptable salts of Formula (I) (as well as Formulas (IA), (IB), and (IC)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), (IB), and (IC)) or pharmaceutically acceptable salts of compounds of Formula (I) (as well as Formulas (IA), (IB), and (IC)) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R-COOH$_{(sol)}$, and R-COO$^−_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R-COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R-COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium or tritium (i.e., $^2$H, $^3$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent S$^1_{example}$ is one of S$_1$ and S$_2$, and substituent S$^2_{example}$ is one of S$_3$ and S$_4$, then these assignments refer to embodiments of this invention given according to the choices S$^1_{example}$ is S$_1$ and S$^2_{example}$ is S$_3$; S$^1_{example}$ is S$_1$ and S$^2_{example}$ is S$_4$; S$^1_{example}$ is S$_2$ and S$^2_{example}$ is S$_3$; S$^1_{example}$ is S$_2$ and S$^2_{example}$ is S$_4$; and equivalents of each one of such choices. The shorter terminology "S$^1_{example}$ is one of S$_1$ and S$_2$, and S$^2_{example}$ is one of S$_3$ and S$_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as R$^1$, R$^2$, R$^3$, R$^4$, R$^{4a}$, R$^{4b}$, R$^{4c}$, R$^{4d}$, R$^5$, R$^6$, R$^7$, Hal, X, Y, Z$^1$, and Z$^2$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such $R^1$, $R^2$, $R^3$, $R^4$, $R^{4a}$, $R^{4b}$, $R^{4c}$, $R^{4d}$, $R^5$, $R^6$, $R^7$, Hal, X, Y, $Z^1$, and $Z^2$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), (IB), and (IC)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), (IB), and (IC)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), (IB), and (IC)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), (IB), and (IC)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), (IB), and (IC)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formulas (IA), (IB), and (IC)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), (IB), and (IC)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), (IB), and (IC)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), (IB), and (IC)), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), (IB), and (IC)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) (as well as Formulas (IA), (IB), and (IC)) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu.g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), (as well as Formulas (IA), (IB), and (IC)). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Table 3. Abbreviations and acronyms used herein include the following.

PREPARATIVE EXAMPLES

Exemplary compounds useful in methods of the invention will now be described by reference to the illustrative synthetic schemes for their general preparation below and the specific examples to follow.

SCHEME 1

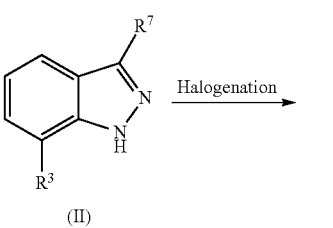

(II) → Halogenation

TABLE 3

| Term | Acronym/Abbreviation |
|---|---|
| acetonitrile | ACN |
| [(2-di-cyclohexylphosphino-3,6-dimethoxy-2',4',6'-triisopropyl-1,1'-biphenyl)-2-(2'-amino-1,1'-biphenyl)]palladium(II) methanesulfonate | BrettPhos-Pd-G3 |
| chloroform | $CHCl_3$ |
| cesium carbonate | $Cs_2C_2O_3$ |
| cesium fluoride | CsF |
| copper (II) acetate | $Cu(OAc)_2$ |
| copper (II) sulfate | $Cu_2SO_4$ |
| dichloromethane | DCM |
| N,N-dimethylformamide | DMF |
| 1,3-dimethyl-3,4,5,6-tetrahydro-2-pyrimidinone | DMPU |
| diethyl ether | $Et_2O$ |
| dimethylsulfoxide | DMSO |
| ethyl acetate | EtOAc |
| ethanol | EtOH |
| flash column chromatography | FCC |
| hydrochloric acid | HCl |
| High-Pressure Liquid Chromatography | HPLC |
| potassium carbonate | $K_2CO_3$ |
| potassium acetate | KOAc |
| magnesium sulfate | $MgSO_4$ |
| sodium fluoride | NaF |
| sodium hydroxide | NaOH |
| sodium sulfate | $Na_2SO_4$ |
| ammonia | $NH_3$ |
| nitrogen gas | $N_2$ |
| para-toluene sulfonate | OTs |
| [1,1'-bis(diphenylphosphino)ferrocene]dichloropalladium(II) | $Pd(dppf)Cl_2$ |
| [1,1'-bis(diphenylphosphino)ferrocene]dichloropalladium(II) dichloromethane complex | $Pd(dppf)Cl_2$—$CH_2Cl_2$ |
| tetrakis(triphenylphosphine) palladium(0) | $Pd(PPh_3)_4$ |
| pinacol | Pin |
| room temperature | rt |
| (2-dicyclohexylphosphino-2',6'-diisopropoxy-1,1'-biphenyl)[2-(2'-amino-1,1'-biphenyl)]palladium(II) methanesulfonate | RuPhos-Pd-G3 |
| 1-chloromethyl-4-fluoro-1,4-diazoniabicyclo[2.2.2]octane bis(tetrafluoroborate) | Selectfluor |
| trifluoroacetic acid | TFA |
| tetrahydrofuran | THF |
| chloro(2-dicyclohexylphosphino-2',4',6'-triisopropyl-1,1'-biphenyl)[2-(2'-amino-1,1'-biphenyl)]palladium(II) | XPhos-Pd-G2 |

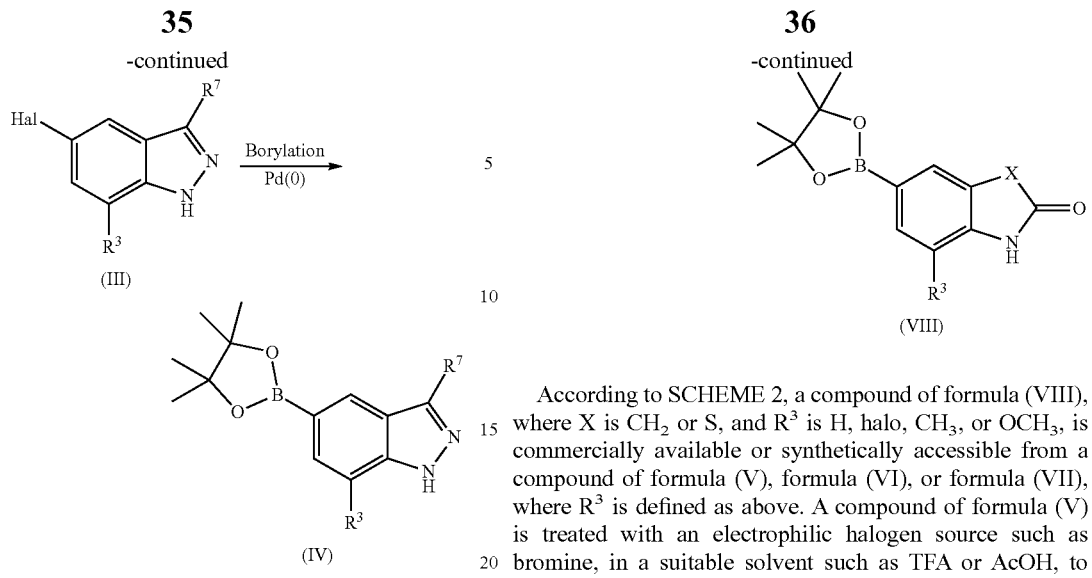

According to SCHEME 1, a compound of formula (IV), where $R^3$ is H, halo, $CH_3$, or $CF_3$, and $R^7$ is H or F, is commercially available or synthetically accessible from a compound of formula (II), where $R^3$ and $R^7$ are defined as above. An indazole compound of formula (II) is treated with an electrophilic halogen source such as bromine, in a suitable solvent such as TFA, to provide a compound of formula (III). A compound of formula (III) is treated with a borylating agent such as bis(pinacolato)diboron, in the presence of a palladium catalyst such as Pd(dppf)Cl$_2$, and a suitable base, such as potassium acetate, employing conventional heating, at a temperature such as 100° C., in a solvent such as 1,4-dioxane, and the like, to provide a compound of formula (IV), where $R^3$ is H, halo, $CH_3$, or $CF_3$, and $R^7$ is H or F.

According to SCHEME 2, a compound of formula (VIII), where X is $CH_2$ or S, and $R^3$ is H, halo, $CH_3$, or $OCH_3$, is commercially available or synthetically accessible from a compound of formula (V), formula (VI), or formula (VII), where $R^3$ is defined as above. A compound of formula (V) is treated with an electrophilic halogen source such as bromine, in a suitable solvent such as TFA or AcOH, to provide a compound of formula (VII), where X is $CH_2$ and $R^3$ is H, halo, or $CH_3$. Alternatively, an isatin compound of formula (VI), where $R^3$ is $OCH_3$, is treated with hydrazine hydrate at a temperature such as 80° C., in a suitable solvent such as butanol, followed by treatment with a suitable base, such as trieythlamine and heating at a temperature such as 100° C. to provide a compound of formula (VII), where X is $CH_2$ and $R^3$ is $OCH_3$. A compound of formula (VII) is treated with a borylating agent such as bis(pinacolato) diboron, in the presence of a palladium catalyst such as Pd(dppf)Cl$_2$, and the like, and a suitable base, such as potassium acetate, employing conventional heating, at a temperature such as 100° C., in a solvent such as 1,4-dioxane, and the like, to provide a compound of formula (VIII), where X and $R^3$ are defined as above.

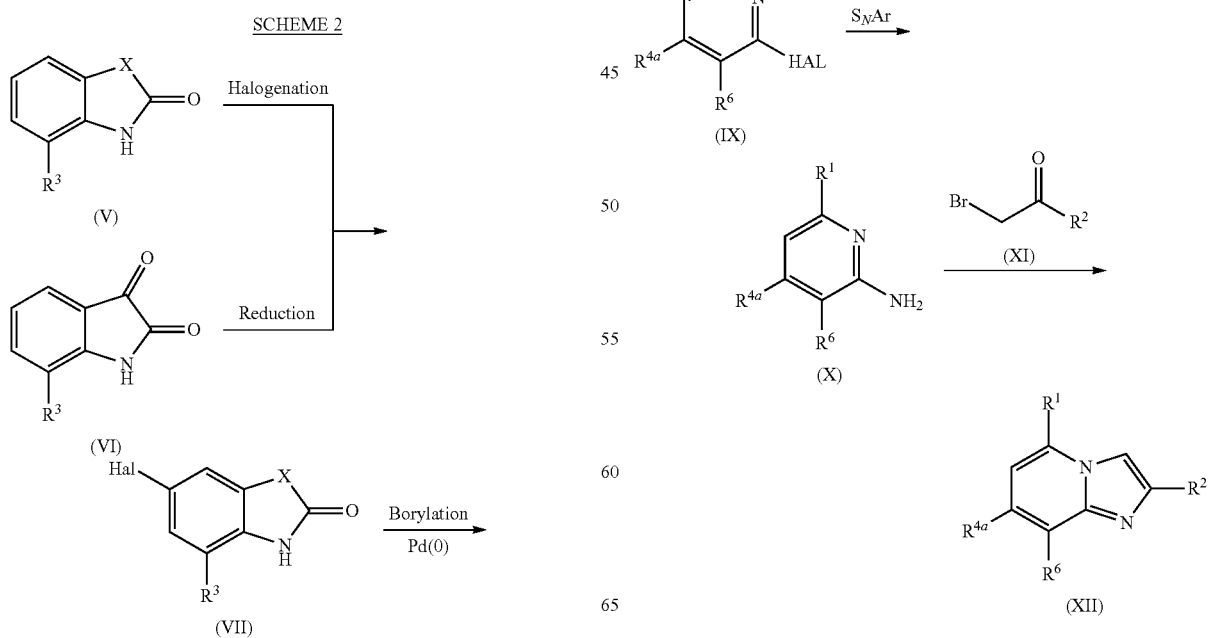

According to SCHEME 3, a compound of formula (XII), where $R^1$ is H; $R^2$ is $C_{1-6}$alkyl, $C_{1-6}$haloalkyl, $C_{3-8}$cycloalkyl, or phenyl; $R^{4a}$ is $CF_3$, $CH_3$, $OCH_3$, Cl, or I; and $R^6$ is Cl, Br, or I, is prepared from a compound of formula (X), which is either commercially available or prepared from a compound of formula (IX), where HAL is F or Cl; $R^1$ is H; $R^{4a}$ is I or $CF_3$; and $R^6$ is Cl. For example, a compound of formula (IX) is treated with an ammonia source such as ammonium hydroxide, and the like, in a suitable solvent such as DMSO, employing temperatures such as 105° C. to 200° C., to provide a compound of formula (X).

A compound of formula (X) is condensed with a bromoketone of formula (XI), where $R^2$ is $CF_3$, tBu, phenyl, or cyclopropyl, often in the presence of a base such as $K_3PO_4$, $K_2CO_3$, and the like, in a suitable solvent such as EtOH, with conventional or microwave heating at temperatures such as 100° C. to 180° C., to provide a compound of formula (XII), where $R^1$ is H; $R^2$ is $C_{1-6}$alkyl, $C_{1-6}$haloalkyl, $C_{3-8}$cycloalkyl, or phenyl; $R^{4a}$ is $CF_3$, $CH_3$, $OCH_3$, Cl, or I; and $R^6$ is Cl, Br, or I.

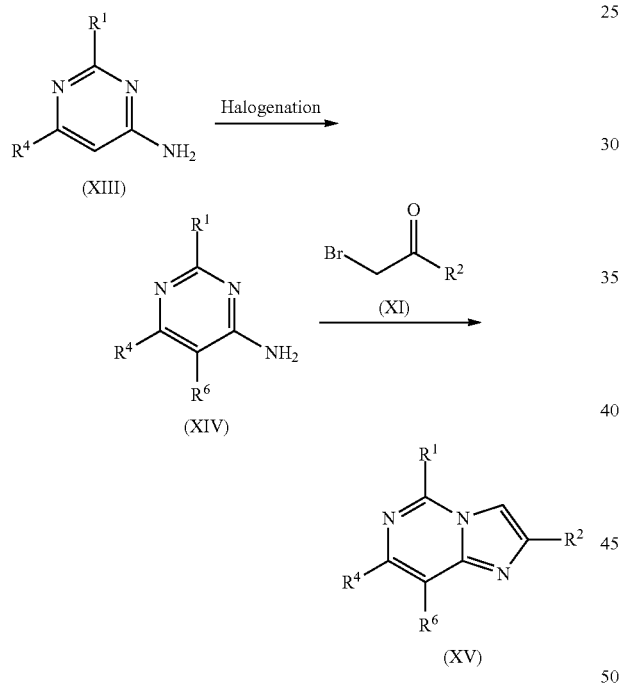

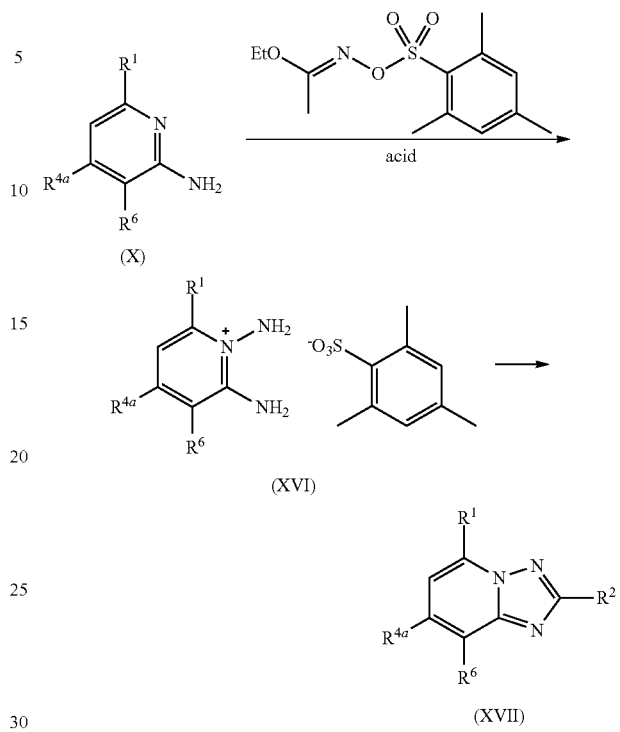

According to SCHEME 4, an aminopyrimidine compound of formula (XIII), where $R^1$ is H or $CH_3$; and $R^4$ is $C_{1-6}$alkyl, $C_{1-6}$haloalkyl, or $C_{3-8}$cycloalkyl, is treated with an electrophilic halogen source such as bromine, N-bromosuccinimide, and the like, in a suitable solvent such as MeOH, DMF, and the like, employing temperatures such as rt to 70° C., to provide a compound of formula (XIV), where $R^6$ is Br.

A compound of formula (XIV) is condensed with a bromoketone of formula (XI), where $R^2$ is $C_{1-6}$alkyl, $C_{1-6}$haloalkyl, or $C_{3-8}$cycloalkyl, in the presence of dehydrating agent such as molecular sieves, in a suitable solvent such as 1,4-dioxane, employing heating at a temperature such as 90° C., to provide a compound of formula (XV), where $R^1$ is H or $CH_3$; $R^2$ is $C_{1-6}$alkyl, $C_{1-6}$haloalkyl, $C_{3-8}$cycloalkyl; $R^{4a}$ is $C_{1-6}$alkyl, $C_{1-6}$haloalkyl, or $C_{3-8}$cycloalkyl; and $R^6$ is Br.

According to SCHEME 5, a compound of formula (X) where $R^1$ is H; $R^{4a}$ is halo, $C_{1-6}$alkoxy or $C_{1-6}$alkyl; and $R^6$ is halo, is dissolved in a solvent such as DCM and reacted with an aminating reagent (formed by treatment of (E)-N-((mesitylsulfonyl)oxy)acetimidate with an acid such as perchloric acid, TFA, and the like), in a solvent such as dioxane and water, at a temperature ranging from 0° C. to provide a compound of formula (XVI), where $R^1$, $R^{4a}$, and $R^6$ are defined as above.

A compound of formula (XVI), where $R^1$ is H; $R^{4a}$ is halo, $C_{1-6}$alkoxy or $C_{1-6}$alkyl; and $R^6$ is halo, is condensed with a suitably substituted anhydride such as trifluoroacetic anhydride, and the like, or a suitably substituted ester such as methyl difluoroacetate, methyl methoxyacetate, and the like, in the presence of a base such as triethylamine in a suitable solvent such as methanol to provide a compound of formula (XVII), where $R^1$ is H; $R^2$ is $CH_2OCH_3$ or $C_{1-6}$haloalkyl; $R^{4a}$ is halo, $C_{1-6}$alkoxy or $C_{1-6}$alkyl; and $R^6$ is halo.

In an alternate method, a compound of formula (XVI), where $R^1$ is H; $R^{4a}$ is halo or $C_{1-6}$haloalkyl; and $R^6$ is halo, is treated with an aliphatic or carbocyclic aldehyde of formula $R^7(C=O)H$, where $R^7$ is $C_{1-6}$alkyl or $C_{3-8}$cycloalkyl, in the presence of an additive such as $Na_2S_2O_5$, in a suitable solvent such as EtOH, DMF, and the like, at temperatures such as 100° C. to 130° C. to provide a compound of formula (XVII), where $R^1$ is H; $R^2$ is $C_{1-6}$alkyl or $C_{3-8}$cycloalkyl; $R^{4a}$ is halo or $C_{1-6}$haloalkyl; and $R^6$ is halo.

SCHEME 6

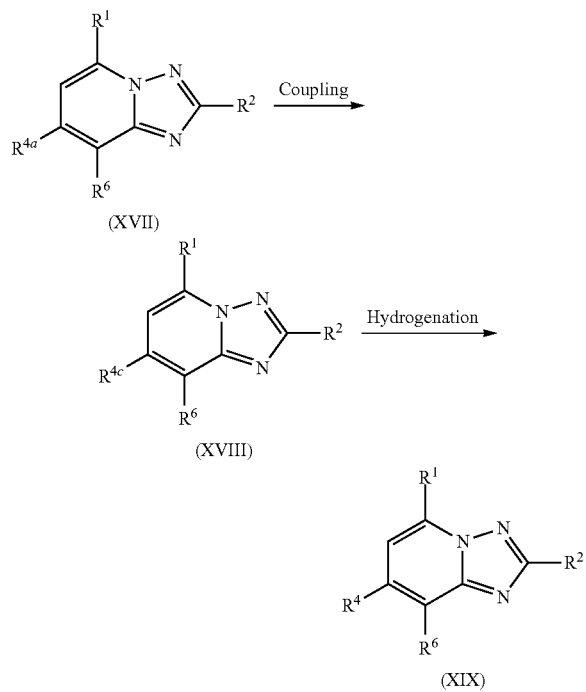

According to SCHEME 6, a compound of formula (XIX), where $R^{4c}$ is $C_{1-6}$alkenyl or $C_{3-8}$cycloalkenyl, is prepared from a compound of formula (XVII), where $R^1$ is H; $R^2$ is $CF_3$; $R^{4a}$ is I; and $R^6$ is Cl, in a metal mediated cross coupling reaction such as a Suzuki coupling. For example, a compound of formula (XVII) is treated with an organoboron reagent such as potassium vinyltrifluoroborate, cyclopenten-1-ylboronic acid, and the like, in a suitable solvent such as 1,4-dioxane, employing microwave heating, at a temperature such as 110° C., to provide a compound of formula (XVIII), where $R^{4c}$ is $CH=CH_2$ or 1-cyclopentenyl. Hydrogenation of a compound of formula (XVIII), under conditions known to one skilled in the art, for example, under an atmosphere of hydrogen gas, in the presence of suitable catalyst such as Pd/C, and the like, in a suitable solvent such as MeOH, and the like, provides a compound of formula (XIX), where $R^1$ is H; $R^2$ is $CF_3$; $R^{4a}$ is ethyl or cyclopentyl; and $R^6$ is Cl.

According to SCHEME 7, a compound of formula (XXII), where Y is N; $R^1$ is H; $R^2$ is $C_{1-6}$haloalkyl; $R^4$ is $C_{1-6}$haloalkyl; and $R^6$ is Cl, is prepared from a compound of formula (XX), where Y is N; $R^1$ is H; $R^2$ is $C_{1-6}$haloalkyl; $R^4$ is I; and $R^6$ is Cl. For example, a compound of formula (XX) undergoes a metal-halogen exchange reaction in the presence of a strong base such as isopropylmagnesium chloride, in a suitable solvent such as THF, and the like, at a temperature such as 0° C., followed by treatment with a formylating reagent such as N-formylpiperidine, to provide an aldehyde compound of formula (XXI), $R^{4b}$ is (C=O)H. A compound of formula (XXI) is treated with a nucleophilic fluorinating reagent such as DAST, in a suitable solvent such as DCM to provide a compound of formula (XXII), where $R^4$ is $C_{1-6}$haloalkyl.

In an alternate method, a compound of formula (XXII), where Y is N or CH; $R^1$ is H; $R^2$ is $C_{1-6}$ alkyl, $C_{3-8}$cycloalkyl, or $C_{1-6}$haloalkyl; $R^4$ is $C_{1-6}$haloalkyl; and $R^6$ is Cl, is prepared from a compound of formula (XX), where Y is N or CH; $R^1$ is H; $R^2$ is $C_{1-6}$ alkyl, $C_{3-8}$cycloalkyl, or $C_{1-6}$haloalkyl; $R^{4a}$ is I; and $R^6$ is Cl. A compound of formula (XX) is treated with a trifluoromethylating reagent such as methyl 2,2-difluoro-2-(fluorosulfonyl)acetate, in the presence of an additive such as CuI, in a suitable solvent system such as DMF/DMPU, employing microwave heating, at a temperature such as 130° C. to provide a compound of formula (XXII), where $R^4$ is $C_{1-6}$haloalkyl.

SCHEME 8

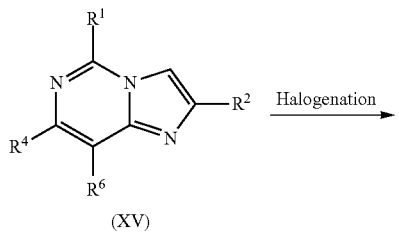

SCHEME 7

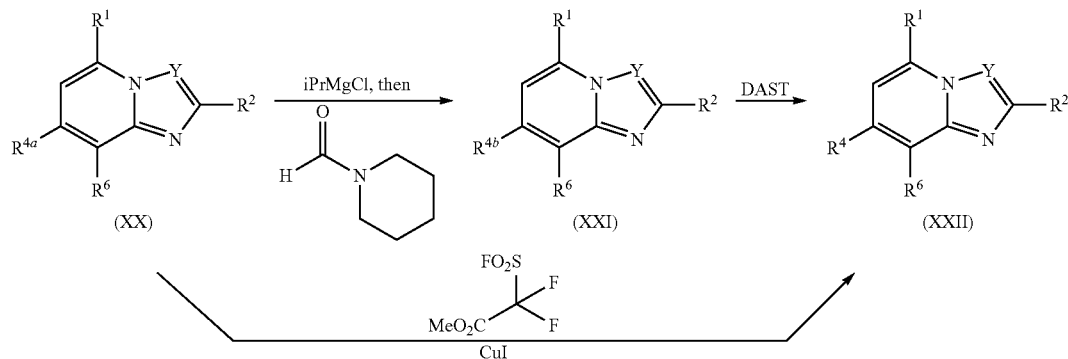

-continued

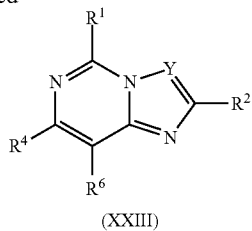

(XXIII)

According to SCHEME 8, a compound of formula (XV), where $R^1$ is H; $R^2$ is cyclopropyl; $R^4$ is $C_{1-6}$haloalkyl; and $R^6$ is Br, is treated with an electrophilic halogen source such as N-chlorosuccinimide, Selectfluor®, and the like, in a suitable solvent such as DCM, MeCN, and the like, at a temperature such as rt to 40° C. to provide a compound of formula (XXIII), where Y is C—Cl or C—F; $R^1$ is H; $R^2$ is cyclopropyl; $R^4$ is $C_{1-6}$haloalkyl; and $R^6$ is Br.

B(Pin), a suitable palladium catalyst such as Pd(PPh$_3$)$_4$ Pd(dppf)Cl$_2$—CH$_2$Cl$_2$, and the like, a base such as Na$_2$CO$_3$, and the like, employing microwave heating at temperatures such as 110° C. to 190° C., in a solvent system such as dioxane, water, or a mixture thereof, to provide a compound of formula (XXIV), which is not isolated. The compound of formula (XXIV), is treated immediately in the same reaction vessel with a commercially available or synthetically accessible boronic ester of formula (IV) or formula (VIII), where $R^3$ is H, F, Cl, or CH$_3$; and —$Z^1$—$Z^2$— is —CH=N—, —CF=N—, or —S—C(=O)—; in a Suzuki reaction using conditions previously described, to provide a compound of Formula (I), where Y is N or CH; $R^1$ is H; $R^2$ is CH$_2$OCH$_3$, $C_{1-5}$haloalkyl, or $C_{3-8}$cycloalkyl; $R^3$ is H, F, Cl, or CH$_3$; $R^4$ is phenyl substituted with F, $C_{1-6}$alkyl, $C_{3-6}$cycloalkyl; and —$Z^1$—$Z^2$— is —CH=N—, —CF=N—, or —S—C

SCHEME 9

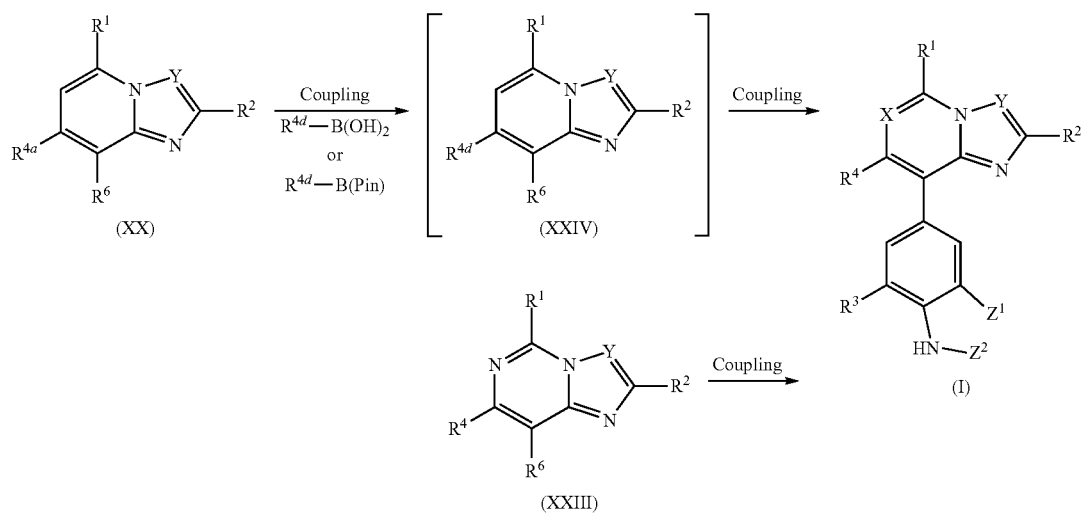

According to SCHEME 9, a compound of formula (XX) where Y is N or CH; $R^1$ is H; $R^2$ is CH$_2$OCH$_3$, $C_{1-5}$haloalkyl, or $C_{3-8}$cycloalkyl; $R^{4a}$ is I; and $R^6$ is Cl; is reacted in a Suzuki metal mediated cross coupling reaction with a suitably substituted commercially available phenyl, alkyl, or cycloalkyl boron reagent of formula $R^{4d}$—B(OH)$_2$ or $R^{4d}$—

(=O)—. In a similar fashion, a compound of formula (XXIII), is reacted in a coupling reaction with a commercially available or synthetically accessible boronic ester of formula (IV) or formula (VIII), to provide a compound of Formula (I), where X is N; Y is CH; $R^1$ is H or CH$_3$; and $R^2$ and $R^4$ are $C_{1-6}$alkyl, $C_{1-6}$haloalkyl, or $C_{3-8}$cycloalkyl.

SCHEME 10

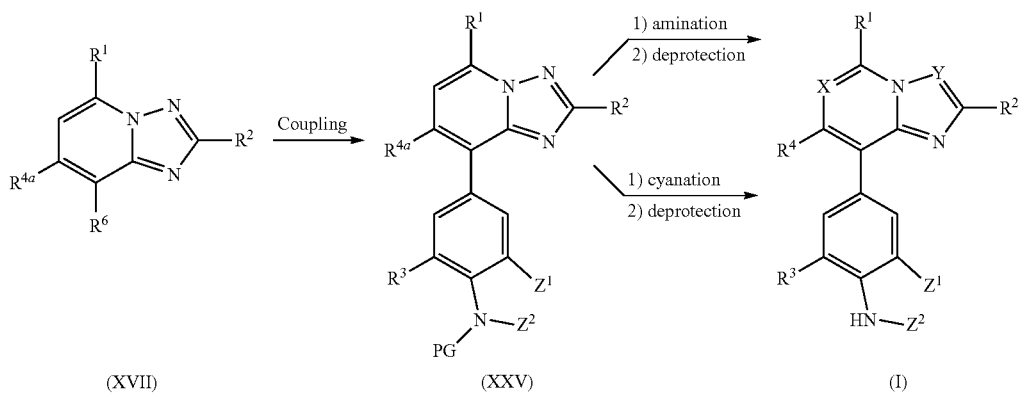

43

According to SCHEME 10, a compound of formula (XVII) where $R^1$ is H; $R^2$ is $C_{1-6}$haloalkyl; $R^{4a}$ is Cl; and $R^6$ is I; is reacted in a Suzuki metal mediated cross coupling reaction with a synthetically accessible boronic ester of formula (IV), where $R^3$ is $CH_3$; and $-Z^1-Z^2-$ is $-CH=N-$; a suitable palladium catalyst such as Pd(dppf)$Cl_2$—$CH_2Cl$, a base such as $Na_2CO_3$, and the like, employing heating at a temperature such as 90° C., in a solvent system such as dioxane, water, or a mixture thereof, to provide a compound of formula (XXV), where $R^1$ is H; $R^2$ is $C_{1-6}$haloalkyl; $R^3$ is $CH_3$ $R^{4a}$ is Cl; $-Z^1-Z^2-$ is $-CH=N-$, and PG is a suitable nitrogen protecting group such as trimethylsilylethoxy methyl (SEM).

A compound of formula (XXV) is reacted with a nitrogen nucleophile such as azetidine or 3-fluoroazetidine in the presence of suitable palladium catalyst such as BrettPhos-Pd-G3, RuPhos-Pd-G3, and the like, and a suitable base such as NaOtBu, employing microwave heating at temperatures such as 130° C. to 150° C., in a solvent system such as 1,4-dioxane, toluene, and the like, followed by deprotection of the SEM protecting group by treatment with an acid such as TFA in a suitable solvent such as DCM, to provide a compound of Formula (I), where $R^1$ is H; $R^2$ is $C_{1-6}$haloalkyl; $R^3$ is $CH_3$; $R^4$ is azetidine or 3-fluoroazetidine; and $-Z^1-Z^2-$ is $-CH=N-$.

In another embodiment, a compound of formula (XXV) is reacted with a cyanide source such as $Zn(CN)_2$ in the presence of a palladium catalyst such as $Pd(PPh_3)_4$, employing microwave heating at a temperature such as 130° C., in a suitable solvent such as DMF, followed by deprotection of the SEM protecting group by treatment with an acid such as TFA in a suitable solvent such as DCM, to provide a compound of Formula (I), where $R^1$ is H; $R^2$ is $C_{1-6}$haloalkyl; $R^3$ is $CH_3$; $R^4$ is CN; and $-Z^1-Z^2-$ is $-CH=N-$.

SCHEME 11

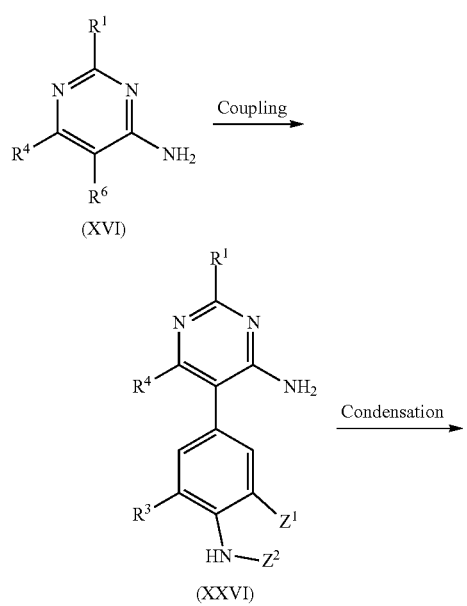

44

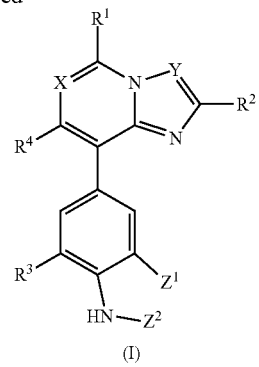

According to SCHEME 11, a compound of formula (XVI) where $R^1$ is H; $R^2$ is $C_{1-6}$alkyl, or $C_{1-6}$haloalkyl; $R^4$ is $C_{1-6}$haloalkyl, $C_{1-6}$alkyl, $C_{3-8}$cycloalkyl; and $R^6$ is halo; is reacted in a Suzuki metal mediated cross coupling reaction with a commercially available or synthetically accessible boronic ester of formula (IV) or (VII) employing methods previously described to provide a compound of formula (XXVI). A compound of formula (XXVI) is condensed with a bromoketone of formula (XI), where $R^2$ is $C_{1-6}$haloalkyl or $C_{1-6}$alkyl, employing conditions previously described to provide a compound of Formula (I), where X is N and Y is CH. Where a protecting group is present on a compound of formula (IV) or (VII), a final deprotection step is added, employing conditions known to one skilled in the art, to provide a compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, $CH_3OH$, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via ⅟₁₆" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 µM, 30×100 or 50×150 mm) or an XBridge $^{18}$C OBD column (5 µM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 µm, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 µm, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 µm, 100×50 mm), mobile phase of 5-99% ACN in 20 mM $NH_4OH$ over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Intermediate 1

7-Chloro-5-(4,4,5,5-tetramethyl-1,3,2-dioxaborolan-2-yl)-1H-indazole

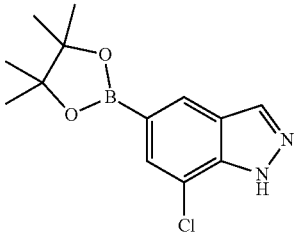 [SMILES: CC1(C)OB(c2cc(Cl)c3[nH]ncc3c2)OC1(C)C]

To a solution of 5-bromo-7-chloro-1H-indazole (1 g, 4.3 mmol) in dioxane (15.0 mL) was added potassium acetate (850 mg, 8.6 mmol), bis(pinacolato)diboron (1.3 g, 5.2 mmol) and $PdCl_2(dppf)-CH_2Cl_2$ (316 mg, 0.43 mmol). The solution was degassed with nitrogen and then heated at 85° C. for 16 hours. After cooling to rt, the reaction mixture was diluted with brine and extracted with EtOAc (×2). The combined organic extracts were dried ($Na_2SO_4$), concentrated, and the crude product was triturated with DCM to provide the title compound as a white solid (916 mg, 76%). MS (ESI): mass calcd. for $C_{13}H_{16}BClN_2O_2$, 278.5; m/z found, 279.0 [M+H]$^+$. $^1$H NMR (400 MHz, DMSO-d$_6$) δ 13.72 (s, 1H), 8.25 (s, 1H), 8.18-8.05 (m, 1H), 7.56 (s, 1H), 1.31 (s, 12H).

Intermediate 2

7-Methyl-5-(4,4,5,5-tetramethyl-1,3,2-dioxaborolan-2-yl)-1H-indazole

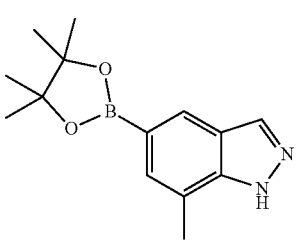 [SMILES: Cc1cc(B2OC(C)(C)C(C)(C)O2)cc2cn[nH]c12]

The title compound is prepared in a manner analogous to Intermediate 1, using 5-bromo-7-methyl-1H-indazole. MS (ESI): mass calcd. for $C_{14}H_{19}BN_2O_2$, 258.1; m/z found, 259.1 [M+H]$^+$. $^1$H NMR (400 MHz, DMSO-d$_6$) δ 13.21 (s, 1H), 8.10 (d, J=1.3 Hz, 1H), 7.98 (s, 1H), 5.76 (s, 1H), 2.52 (s, 3H), 1.30 (s, 12H).

Intermediate 3

7-Methyl-5-(4,4,5,5-tetramethyl-1,3,2-dioxaborolan-2-yl)-1-((2-(trimethylsilyl)ethoxy)methyl)-1H-indazole

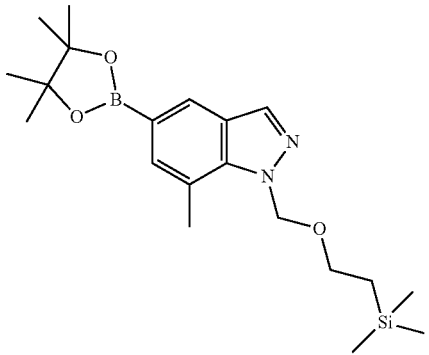

Step A: 5-Bromo-7-methyl-1-((2-(trimethylsilyl)ethoxy)methyl)-1H-indazole. To a cooled (0° C.) solution of 5-bromo-7-methyl-1H-indazole (1 g, 4.7 mmol) in THF (10.0 mL) was added portion wise sodium hydride (284 mg, 60 wt % in mineral oil, 7.1 mmol). Stirring was maintained for 20 minutes at same temperature and then added (2-(chloromethoxy) ethyl) trimethylsilane (0.84 mL, 4.7 mmol), drop wise over a period of 10 minutes. The mixture was warmed to rt and stirred for 2 hours. The crude mixture was diluted with water and extracted with DCM (×2). The combined organic extracts were washed with brine, dried (Na$_2$SO$_4$) and concentrated in vacuo. Purification (FCC; SiO$_2$; 0-50% EtOAc/hexanes) provided the title compound as a white solid (755 mg, 47%). MS (ESI): mass calcd. for C$_{14}$H$_{21}$BrN$_2$OSi, 341.3; m/z found, 343.0 [M+H]$^+$. $^1$H NMR (400 MHz, DMSO-d$_6$) δ 8.19 (s, 1H), 7.98 (s, 1H), 7.48 (s, 1H), 5.93 (s, 2H), 3.68-3.58 (m, 2H), 2.83 (s, 3H), 0.91 (t, J=7.8 Hz, 2H), 0.00 (s, 9H).

Step B: 7-Methyl-5-(4,4,5,5-tetramethyl-1,3,2-dioxaborolan-2-yl)-1-((2-(trimethylsilyl)ethoxy)methyl)-1H-indazole. The title compound was prepared in a manner analogous to Intermediate 1 using 5-bromo-7-methyl-1-((2-(trimethylsilyl) ethoxy) methyl)-1H-indazole from Step A. MS (ESI): mass calcd. for C$_{20}$H$_{33}$BN$_2$O$_3$Si, 388.4; m/z found, 389.3 [M+H]$^+$. $^1$H NMR (400 MHz, DMSO-d$_6$) δ 8.13 (s, 1H), 8.01-7.98 (m, 1H), 7.43 (t, J=1.1 Hz, 1H), 5.82 (s, 2H), 3.48 (t, J=7.9 Hz, 2H), 2.71 (s, 3H), 1.31 (s, 12H), 0.78 (dd, J=8.4, 7.4 Hz, 2H), −0.13 (s, 9H).

Intermediate 4

3-Fluoro-5-(4,4,5,5-tetramethyl-1,3,2-dioxaborolan-2-yl)-1H-indazole

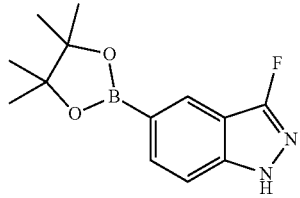 [SMILES: CC1(C)OB(c2ccc3[nH]nc(F)c3c2)OC1(C)C]

The title compound is prepared in a manner analogous to Intermediate 1 using 5-bromo-3-fluoro-1H-indazole. MS (ESI): mass calcd. for C$_{13}$H$_{16}$BFN$_2$O$_2$, 262.1; m/z found, 263.1 [M+H]+.

Intermediate 5

7-Methyl-5-(4,4,5,5-tetramethyl-1,3,2-dioxaborolan-2-yl)indolin-2-one

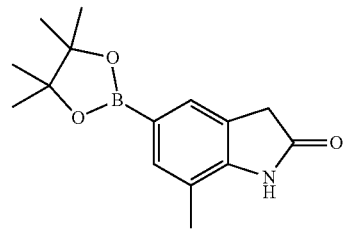 [SMILES: Cc1cc(B2OC(C)(C)C(C)(C)O2)cc2c1NC(=O)C2]

The title compound is prepared in a manner analogous to Intermediate 1 using 5-bromo-7-methylindolin-2-one. MS (ESI): mass calcd. for C$_{16}$H$_{12}$ClF$_2$NO$_2$, 273.1; m/z found, 275.1 [M+H]$^+$. $^1$H NMR (400 MHz, DMSO-d$_6$) δ 10.55 (s, 1H), 7.32 (s, 1H), 7.31 (s, 1H), 3.47 (s, 2H), 2.19 (s, 3H), 1.26 (s, 12H).

Intermediate 6

7-Fluoro-5-(4,4,5,5-tetramethyl-1,3,2-dioxaborolan-2-yl)indolin-2-one

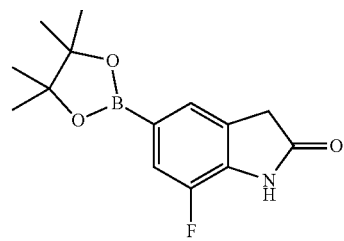 [SMILES: CC1(C)OB(c2cc(F)c3c(c2)CC(=O)N3)OC1(C)C]

The title compound is prepared in a manner analogous to Intermediate 1 using 5-bromo-7-fluoroindolin-2-one. MS (ESI): mass calcd. for C$_{14}$H$_{17}$BFNO$_3$, 277.1; m/z found, 278.1 [M+H]$^+$. $^1$H NMR (500 MHz, DMSO-d$_6$) δ 11.02 (s, 1H), 7.37-7.26 (m, 1H), 7.30-7.20 (m, 1H), 3.57-3.56 (m, 2H), 1.28 (s, 12H).

Intermediate 7

7-Chloro-5-(4,4,5,5-tetramethyl-1,3,2-dioxaborolan-2-yl)indolin-2-one

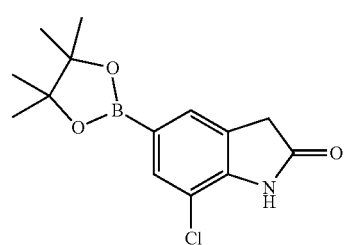 [SMILES: CC1(C)OB(c2cc(Cl)c3c(c2)CC(=O)N3)OC1(C)C]

Step A: 5-bromo-7-chloroindolin-2-one. To a cooled (0° C.) solution of 7-chloroindolin-2-one (1.0 g, 6.0 mmol) in TFA (11 mL) was added N-bromosuccinimide (1.0 g, 6.0 mmol) portion wise, and the resulting mixture was stirred at 0° C. for 6 h. The solvent was removed in vacuo and the residue was diluted and evaporated successively with DCM (25 mL) and EtOAc (25 mL). The crude product was triturated with EtOH to provide the title compound as a white solid (861 mg, 58% yield). MS (ESI): mass calcd. for $C_8H_5BrClNO$, 244.9; m/z found, 246.0 [M+H]$^+$. $^1$H NMR (500 MHz, DMSO-$d_6$) δ 10.92 (s, 1H), 7.52-7.48 (m, 1H), 7.38 (d, J=1.2 Hz, 1H), 3.62 (s, 2H).

Step B: 7-chloro-5-(4,4,5,5-tetramethyl-1,3,2-dioxaborolan-2-yl)indolin-2-one. The title compound was prepared in a manner analogous to Intermediate 1, substituting 5-bromo-7-chloroindolin-2-one for 5-bromo-7-chloro-1H-indazole. The crude product was triturated with DCM to provide the title compound as a white solid (1.6 g, 65% yield). MS (ESI): mass calcd. for $C_{14}H_{17}BClNO_3$, 293.1; m/z found, 294.1 [M+H]$^+$. $^1$H NMR (400 MHz, DMSO-$d_6$) δ 10.94 (s, 1H), 7.43 (d, J=1.1 Hz, 1H), 7.41 (d, J=1.2 Hz, 1H), 3.60 (t, J=1.0 Hz, 2H), 1.28 (s, 12H).

Intermediate 8

7-Methoxy-5-(4,4,5,5-tetramethyl-1,3,2-dioxaborolan-2-yl)indolin-2-one

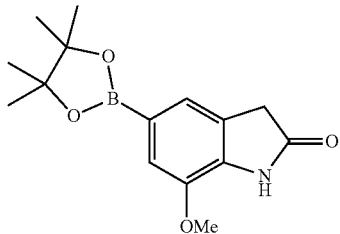 [SMILES: COc1cc(B2OC(C)(C)C(C)(C)O2)cc2c1NC(=O)C2]

Step A: 5-Bromo-7-methoxyindoline-2,3-dione. To a suspension of 7-methoxyindoline-2,3-dione (1 g, 5.6 mmol) in AcOH (5.6 mL) was added bromine (0.35 mL, 6.7 mmol) at 0° C. The mixture was allowed to stir at ambient temperature for 2 hours and then poured into ice and stirred for 30 minutes. The resulting mixture was filtered and the solids were washed with $H_2O$ to afford the title compound as an orange solid (1.3 g, 92%). MS (ESI): mass calcd. for $C_9H_6BrNO_3$, 256.0; m/z found, 257.6 [M+H]$^+$. $^1$H NMR (400 MHz, DMSO-$d_6$) δ 11.22 (s, 1H), 7.48 (d, J=1.7 Hz, 1H), 7.25 (dd, J=1.8, 0.7 Hz, 1H), 3.90 (s, 3H).

Step B: 5-Bromo-7-methoxyindolin-2-one. To a solution of 5-bromo-7-methoxyindoline-2,3-dione (673 mg, 2.6 mmol) in n-butanol (8 mL) was added hydrazine hydrate (153 μL, 3.1 mmol). The mixture was heated at 80° C. for 3 h. The temperature was maintained at 80° C. and TEA (548 μL, 3.9 mmol) was added. The temperature was then increased to 100° C. and the reaction was stirred at reflux for 24 hours. The reaction was cooled to rt and the mixture was concentrated in vacuo. The crude residue was suspended in hexanes and the resulting mixture was filtered. The solids were washed with hexanes to afford the title compound (297 mg, 46%). MS (ESI): mass calcd. for $C_9H_8BrNO_2$, 242.0; m/z found, 243.9 [M+H]$^+$. $^1$H NMR (400 MHz, DMSO-$d_6$) δ 10.52 (s, 1H), 7.09 (d, J=1.7 Hz, 1H), 7.02 (q, J=1.2 Hz, 1H), 3.82 (s, 3H), 3.50 (t, J=1.0 Hz, 2H).

Step C: 7-Methoxy-5-(4,4,5,5-tetramethyl-1,3,2-dioxaborolan-2-yl)indolin-2-one. The title compound was prepared in a manner analogous to Intermediate 1, using 5-bromo-7-methoxyindolin-2-one. The crude product was triturated with EtOAc to provide the title compound as yellow solid (74%). MS (ESI): mass calcd. for $C_{15}H_{20}BNO_4$, 289.1; m/z found, 290.1 [M+H]$^+$. $^1$H NMR (400 MHz, DMSO-$d_6$) δ 10.55 (s, 1H), 7.16 (d, J=1.1 Hz, 1H), 7.10 (s, 1H), 3.82 (s, 3H), 3.48 (s, 2H), 1.28 (s, 12H).

Intermediate 9

6-(4,4,5,5-Tetramethyl-1,3,2-dioxaborolan-2-yl)-3-((2-(trimethylsilyl)ethoxy)methyl)benzo[d]thiazol-2(3H)-one

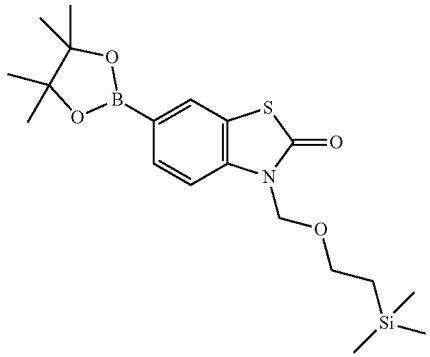

The title compound is prepared in a manner analogous to Intermediate 3 using 6-bromobenzo[d]thiazol-2(3H)-one, in Step A. $^1$H NMR (400 MHz, DMSO-$d_6$) δ 8.02 (d, J=1.1 Hz, 1H), 7.74 (dd, J=8.1, 1.2 Hz, 1H), 7.45 (d, J=8.1 Hz, 1H), 5.43 (s, 2H), 0.04--0.13 (m, 9H), 3.64 (dd, J=8.4, 7.5 Hz, 2H), 1.38 (s, 12H), 0.97-0.89 (m, 2H).

Intermediate 10

3-Chloro-4-iodopyridin-2-amine

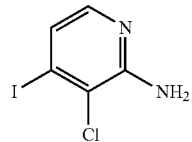

To a high pressure sealable tube charged with 3-chloro-2-fluoro-4-iodopyridine (3.15 g, 12.25 mmol) was added $NH_3$ (5.0 mL, 28% in $H_2O$) followed by DMSO (5 mL). The tube was capped and the reaction mixture heated to 105° C. for 3 hours after which the reaction was allowed to cool to rt. The resulting solids were filtered off, washed with $H_2O$ (×3), and dried to afford the title compound as colorless flakes (3.09 g). The resulting filtrate was extracted with EtOAc (×3). The combined organic extracts were washed with 5% LiCl sol'n (×2), brine, dried (MgSO$_4$), filtered, and concentrated in vacuo to afford additional title compound as an off-white solid (220 mg). MS (ESI): mass calcd. for $C_5H_4ClN_2I$, 253.9; m/z found, 254.9 [M+H]$^+$. $^1$H NMR (400 MHz, CDCl$_3$) δ 7.58 (d, J=5.2 Hz, 1H), 7.13 (d, J=5.2 Hz, 1H), 5.00 (br s, 2H).

Intermediate 11

3-Chloro-4-(trifluoromethyl)pyridin-2-amine

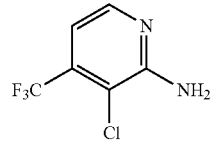 [SMILES: Nc1nccc(C(F)(F)F)c1Cl]

A Parr bomb was charged with 2,3-dichloro-4-(trifluoromethyl)pyridine (5 g, 23 mmol) and NH$_3$ (200 mL, 28% in H$_2$O). The apparatus was sealed and heated at 200° C. for 12.5 hours. The reaction was allowed to cool to rt. The resulting solids were filtered, washed with H$_2$O, and dried to afford the title compound as a colorless solid (3.77 g). The resulting filtrate was extracted with Et$_2$O (×3). The combined organic extracts were dried (MgSO$_4$), filtered, and concentrated to afford additional title compound as a light yellow solid (625 mg). MS (ESI): mass calcd. for C$_6$H$_3$ClF$_3$N$_2$I, 196.0; m/z found, 197.0 [M+H]$^+$. $^1$H NMR (400 MHz, CDCl$_3$) δ 8.11 (d, J=5.2 Hz, 1H), 6.92 (d, J=5.1 Hz, 1H), 5.18 (s, 2H).

Intermediate 12

5-Bromo-6-(trifluoromethyl)pyrimidin-4-amine

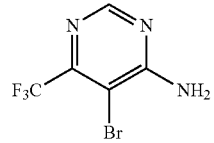

Method A:

To a cooled (0° C.) solution of 6-(trifluoromethyl)pyrimidin-4-amine (2.0 g, 12.3 mmol) in MeOH (100.0 mL) was added bromine (1.3 mL, 24.5 mmol) drop wise over a period of 10 minutes. The mixture was stirred at rt for 2 hours. The reaction was quenched with H$_2$O and concentrated in vacuo to obtain crude HBr salt (3.57 g). The crude product was purified by reverse-phase HPLC using a XBridge C18 column (5 μm, 100×4.6 mm), mobile phase of 10-100% ACN in 20 mM NH$_4$OH, to afford the title compound as tan solid (2.4 g, 80%). MS (ESI): mass calcd. for C$_5$H$_3$BrF$_3$N$_3$, 241.9; m/z found, 243.9 [M+H]$^+$. $^1$H NMR (500 MHz, DMSO-d$_6$) δ 8.46 (s, 1H), 8.25 (s, 1H), 7.52 (s, 1H).

Method B:

To a solution of 6-(trifluoromethyl) pyrimidin-4-amine (1.0 g, 6.2 mmol) in DMF (30 mL) was added NBS (1.2 g, 6.8 mmol). The mixture was heated to 70° C. for 1 hour. The reaction mixture was cooled to rt, diluted with H$_2$O, and extracted with EtOAc (×2). The combined organic extracts were washed with brine; dried (Na$_2$SO$_4$) and concentrated in vacuo. The crude product was triturated in DCM to obtain title compound as white solid (1.38 g, 93%).

Intermediate 13

5-Bromo-6-isopropylpyrimidin-4-amine

The title compound is prepared in a manner analogous to Intermediate 12 (Method A) using 6-isopropylpyrimidin-4-amine. MS (ESI): mass calcd. for C$_7$H$_{10}$BrN$_3$, 216.0; m/z found, 217.9 [M+H]$^+$.

Intermediate 14

5-Bromo-6-ethylpyrimidin-4-amine

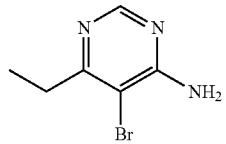

The title compound is prepared in a manner analogous to Intermediate 12 (Method B) using 6-ethylpyrimidin-4-amine. MS (ESI): mass calcd. for C$_6$H$_8$BrN$_3$, 202.0; m/z found, 204.0 [M+H]$^+$. $^1$H NMR (400 MHz, DMSO-d$_6$) δ 8.23 (s, 1H), 7.08 (s, 2H), 2.70 (q, J=7.5 Hz, 2H), 1.16 (t, J=7.5 Hz, 3H).

Intermediate 15

5-Bromo-6-methylpyrimidin-4-amine

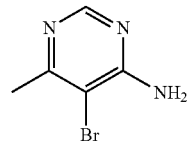

The title compound is prepared in a manner analogous to Intermediate 12 (Method B) using 6-methylpyrimidin-4-amine. MS (ESI): mass calcd. for C$_5$H$_6$BrN$_3$, 188.0; m/z found, 189.9 [M+H]$^+$. $^1$H NMR (400 MHz, DMSO-d$_6$) δ 8.18 (s, 1H), 7.08 (s, 2H), 2.38 (s, 3H).

Intermediate 16

5-Bromo-6-cyclopropylpyrimidin-4-amine

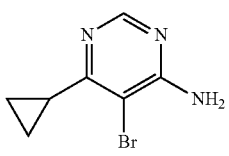 [SMILES: Nc1ncnc(C2CC2)c1Br]

The title compound is prepared in a manner analogous to Intermediate 12 (Method B) using 6-cyclopropylpyrimidin-4-amine. MS (ESI): mass calcd. for $C_7H_8BrN_3$, 214.0; m/z found, 216.0 $[M+H]^+$.

Intermediate 17

5-Bromo-6-cyclopropyl-2-methylpyrimidin-4-amine

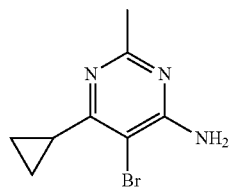

The title compound is prepared in a manner analogous to Intermediate 12 (Method B) using 6-cyclopropyl-2-methylpyrimidin-4-amine. MS (ESI): mass calcd. for $C_8H_{10}BrN_3$, 228.0; m/z found, 229.0 $[M+H]^+$.

Intermediate 18

3-Bromo-1,1-difluoropropan-2-one

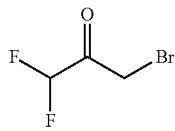

To a cooled (−78° C.) mixture of ethyl 2,2-difluoroacetate (1.6 mL, 15.2 mmol) and dibromomethane (2.1 mL, 30.4 mmol) in THF (60 mL) was added methyllithium (1.6M in diethylether, 19.0 mL, 30.4 mmol) drop wise over a period of 10 minutes. Stirring was maintained at −78° C. for 45 minutes. The reaction was quenched with AcOH (3.5 mL, 61 mmol) and the mixture was slowly warmed to 0° C. The reaction mixture was diluted with $H_2O$, extracted with $Et_2O$ (×2) and the combined organic extracts were dried ($Na_2SO_4$). The crude product was concentrated under reduced pressure using a rotary evaporator to obtain title compound as colorless oil (2.32 g).

Intermediate 19

8-Chloro-7-iodo-2-(trifluoromethyl)-[1,2,4]triazolo[1,5-a]pyridine

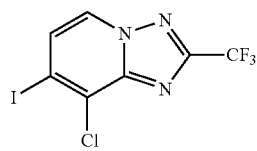 [SMILES: FC(F)(F)c1nc2c(Cl)c(I)ccn2n1]

Step A: O-(Mesitylsulfonyl)hydroxylamine. To a solution of ethyl O-mesitylsulfonylacetohydroxamate (1.68 g, 5.88 mmol) in 1,4-dioxane (9.7 mL) at 0° C. was added a 70% aqueous solution of perchloric acid (8.4 mL, 98.7 mmol) drop wise via syringe. The mixture was maintained at 0° C. for 10 minutes, and then cold $H_2O$ (40 mL) was added. Most of the solvent was then removed via vacuum filtration (do not filter to complete dryness; intermediate is reported to be potentially explosive when dry). The wet solid was then dissolved in DCM (17 mL), the aqueous layer separated, and the remaining organic layer was dried ($Na_2SO_4$), and filtered.

Step B: 1,2-Diamino-3-chloro-4-iodopyridin-1-ium 2,4,6-trimethylbenzenesulfonate. The filtrate from Step A (O-(mesitylsulfonyl)hydroxylamine) was then added to a cold (0° C.) solution of 3-chloro-4-iodopyridin-2-amine (Intermediate 10, 1.00 g, 3.93 mmol) in DCM (34 mL), and the mixture allowed to warm to rt and stirred until LCMS analysis indicated complete conversion. $Et_2O$ (150 mL) was added, and the precipitate was collected via vacuum filtration to afford the title compound as a white solid (1.75 g, 95% yield). $^1$H NMR (600 MHz, DMSO-$d_6$) δ 8.72 (bs, 2H), 7.80 (d, J=7.1 Hz, 1H), 7.38 (d, J=7.0 Hz, 1H), 6.88 (s, 2H), 6.76-6.70 (m, 2H), 2.49 (s, 6H), 2.17 (s, 3H).

Step C: 8-Chloro-7-iodo-2-(trifluoromethyl)-[1,2,4]triazolo[1,5-a]pyridine. To a suspension of 1,2-diamino-3-chloro-4-iodopyridin-1-ium 2,4,6-trimethylbenzenesulfonate (2 g, 4.26 mmol) in MeOH (16.5 mL) at 0° C. was added $Et_3N$ (1.78 mL, 12.8 mmol), followed by trifluoroacetic anhydride (0.90 mL, 6.51 mmol) dropwise via syringe. The reaction mixture was maintained at 0° C. for 10 minutes, then allowed to warm to rt and stirred overnight. The reaction mixture was concentrated in vacuo, and purified (FCC, $SiO_2$, 0-100% EtOAc/hexanes) to afford the title compound as a white solid (1.26 g, 85% yield). MS (ESI): mass calcd. for $C_7H_2ClF_3IN_3$, 346.9; m/z found, 347.9 $[M+H]^+$. $^1$H NMR (400 MHz, $CDCl_3$) δ 8.31 (d, J=7.1 Hz, 1H), 7.59 (d, J=7.2 Hz, 1H).

Intermediate 20

7-Chloro-8-iodo-2-(trifluoromethyl)-[1,2,4]triazolo[1,5-a]pyridine

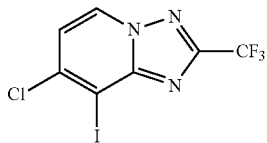 [SMILES: FC(F)(F)c1nc2c(I)c(Cl)ccn2n1]

The title compound was prepared in a manner analogous to Intermediate 19 using 4-chloro-3-iodopyridin-2-amine in Step B. MS (ESI): mass calcd. for $C_7H_2ClF_3IN_3$, 346.9; m/z found, 347.9 $[M+H]^+$. $^1$H NMR (500 MHz, DMSO-$d_6$) δ 9.11 (d, J=7.2 Hz, 1H), 7.61 (d, J=7.2 Hz, 1H).

Intermediate 21

8-Bromo-7-methyl-2-(trifluoromethyl)-[1,2,4]triazolo[1,5-a]pyridine

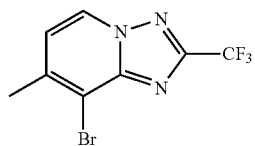

The title compound was prepared in a manner analogous to Intermediate 19 using 3-bromo-4-methylpyridin-2-amine in Step B. MS (ESI): mass calcd. for $C_8H_5BrF_3N_3$, 279.0; m/z found, 280.1 [M+H]$^+$. $^1$H NMR (400 MHz, CDCl$_3$) δ 8.48 (d, J=6.9 Hz, 1H), 7.08 (d, J=7.0 Hz, 1H), 1.56 (s, 3H).

Intermediate 22

8-Iodo-7-methoxy-2-(trifluoromethyl)-[1,2,4]triazolo[1,5-a]pyridine

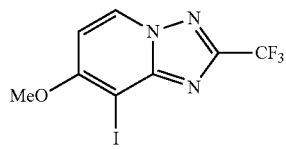 [SMILES: COc1ccn2nc(C(F)(F)F)nc2c1I]

The title compound was prepared in a manner analogous to Intermediate 19 using 3-iodo-4-methoxypyridin-2-amine in Step B. MS (ESI): mass calcd. for $C_8H_5F_3IN_3O$, 342.9; m/z found, 344.0 [M+H]$^+$. $^1$H NMR (500 MHz, CDCl$_3$) δ 8.54 (d, J=7.6 Hz, 1H), 6.90 (d, J=7.6 Hz, 1H), 4.09 (s, 3H).

Intermediate 23

8-Chloro-2-(difluoromethyl)-7-iodo-[1,2,4]triazolo[1,5-a]pyridine

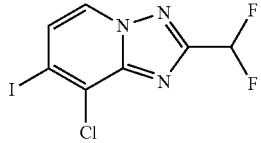 [SMILES: FC(F)c1nc2c(Cl)c(I)ccn2n1]

The title compound was prepared in a manner analogous to Intermediate 19 using methyl difluoroacetate in Step C. MS (ESI): mass calcd. for $C_7H_3ClF_2IN_3$, 328.9; m/z found, 330.0 [M+H]$^+$.

Intermediate 24

8-Chloro-7-iodo-2-(methoxymethyl)-[1,2,4]triazolo[1,5-a]pyridine

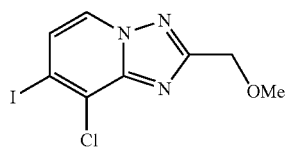 [SMILES: COCc1nc2c(Cl)c(I)ccn2n1]

The title compound was prepared in a manner analogous to Intermediate 19 using methyl methoxyacetate in Step C. MS (ESI): mass calcd. for $C_8H_7ClIN_3O$, 322.9; m/z found, 324.0 [M+H]$^+$.

Intermediate 25

8-Chloro-2-(difluoromethyl)-7-(trifluoromethyl)-[1,2,4]triazolo[1,5-a]pyridine

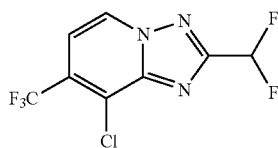 [SMILES: FC(F)c1nc2c(Cl)c(C(F)(F)F)ccn2n1]

The title compound was prepared in a manner analogous to Intermediate 19 using 3-chloro-4-(trifluoromethyl)pyridin-2-amine (Intermediate 11) in Step B and methyl difluoroacetate in Step C. MS (ESI): mass calcd. for $C_8H_3ClF_5N_3$, 271.0; m/z found, 272.0 [M+H]$^+$. $^1$H NMR (500 MHz, CDCl$_3$) δ 8.70-8.66 (m, 1H), 7.43 (d, J=7.2 Hz, 1H), 6.94 (t, J=55 Hz, 1H).

Intermediate 26

8-Chloro-2-cyclopropyl-7-iodo-[1,2,4]triazolo[1,5-a]pyridine

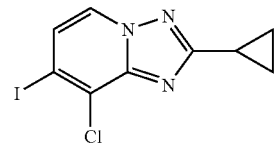 [SMILES: Clc1c(I)ccn2nc(C3CC3)nc12]

To a solution of 1,2-diamino-3-chloro-4-iodopyridin-1-ium 2,4,6-trimethylbenzenesulfonate (Intermediate 19, product from Step B, 0.3 g, 0.179 mmol) and cyclopropanecarboxaldehyde (0.18 mL, 2.40 mmol) in DMF (3.1 mL) in a microwave vial was added Na$_2$S$_2$O$_5$ (258 mg, 1.36 mmol). The vial was capped and sealed, and the mixture stirred at 100° C. for 2 h. After cooling to rt, the reaction was diluted with EtOAc, and washed with H$_2$O. The aqueous layer was extracted with EtOAc (×2), and the combined organics were washed with brine (×3), dried (Na$_2$SO$_4$), and filtered. The filtrate was concentrated in vacuo, and the residue purified (FCC, SiO$_2$, 0-50% EtOAc/hexanes) to afford the title compound as a white solid (97.2 mg, 48% yield). MS (ESI): mass calcd. for $C_9H_7ClIN_3$, 318.9; m/z found, 320.0 [M+H]$^+$. $^1$H NMR (500 MHz, CDCl$_3$) δ 8.10 (d, J=7.1 Hz, 1H), 7.30 (d, J=7.1 Hz, 1H), 2.26-2.18 (m, 1H), 1.19-1.15 (m, 2H), 1.14-1.08 (m, 2H).

Intermediate 27

8-Chloro-7-iodo-2-methyl-[1,2,4]triazolo[1,5-a]pyridine

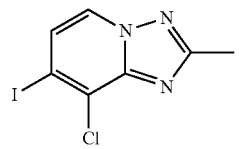

The title compound is prepared in a manner analogous to Intermediate 26 using acetaldehyde. MS (ESI): mass calcd. for $C_7H_5ClIN_3$, 293.5; m/z found, 294.0 [M+H]$^+$. $^1$H NMR (400 MHz, DMSO-$d_6$) δ 8.63 (d, J=7.0 Hz, 1H), 7.55 (d, J=7.0 Hz, 1H), 2.49 (s, 3H).

Intermediate 28

8-Chloro-2-ethyl-7-iodo-[1,2,4]triazolo[1,5-a]pyridine

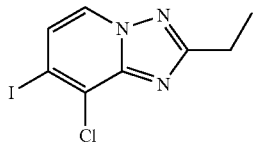

The title compound is prepared in a manner analogous to Intermediate 26 using propionaldehyde. MS (ESI): mass calcd. for $C_8H_7ClIN_3$, 307.5; m/z found, 308.0 [M+H]$^+$. $^1$H NMR (400 MHz, DMSO-$d_6$) δ 8.64 (d, J=7.0 Hz, 1H), 7.55 (d, J=7.0 Hz, 1H), 2.86 (q, J=7.6 Hz, 2H), 1.32 (t, J=7.6 Hz, 3H).

Intermediate 29

8-Chloro-2-cyclobutyl-7-iodo-[1,2,4]triazolo[1,5-a]pyridine

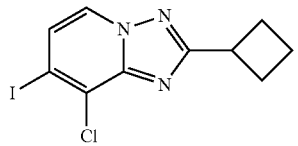 [SMILES: Clc1c(I)ccn2nc(C3CCC3)nc12]

The title compound was prepared in a manner analogous to Intermediate 26 using cyclobutanecarboxaldehyde. MS (ESI): mass calcd. for $C_{10}H_9ClIN_3$, 333.0; m/z found, 334.0 [M+H]$^+$.

Intermediate 30

8-Chloro-7-iodo-2-isopropyl-[1,2,4]triazolo[1,5-a]pyridine

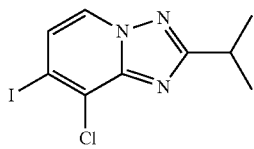

The title compound is prepared in a manner analogous to Intermediate 26 using isobutyraldehyde. MS (ESI): mass calcd. for $C_9H_9ClIN_3$, 321.5; m/z found, 322.0 [M+H]$^+$. $^1$H NMR (400 MHz, DMSO-$d_6$) δ 8.65 (d, J=7.0 Hz, 1H), 7.55 (d, J=7.0 Hz, 1H), 3.24-3.12 (m, 1H), 1.35 (d, J=6.9 Hz, 6H).

Intermediate 31

8-Chloro-2-cyclopentyl-7-iodo-[1,2,4]triazolo[1,5-a]pyridine

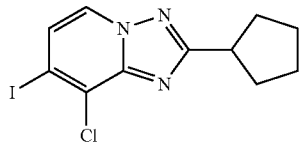 [SMILES: Clc1c(I)ccn2nc(C3CCCC3)nc12]

The title compound was prepared in a manner analogous to Intermediate 26 using cyclopentanecarboxaldehyde. MS (ESI): mass calcd. for $C_{11}H_{11}ClIN_3$, 347.0; m/z found, 348.0 [M+H]$^+$. $^1$H NMR (400 MHz, DMSO-$d_6$) δ 8.65 (d, J=7.0 Hz, 1H), 7.55 (d, J=7.0 Hz, 1H), 3.24-3.12 (m, 1H), 1.35 (d, J=6.9 Hz, 6H).

Intermediate 32

8-Bromo-2-isopropyl-7-methyl-[1,2,4]triazolo[1,5-a]pyridine

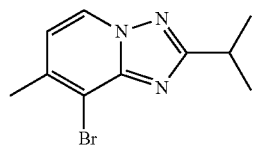

Step A: 1,2-Diamino-3-bromo-4-methylpyridin-1-ium 2,4,6-trimethylbenzenesulfonate. The title compound was prepared in a manner analogous to Intermediate 19, Step B using 3-bromo-4-methylpyridin-2-amine. $^1$H NMR (400 MHz, DMSO-$d_6$) δ 8.34 (s, 3H), 8.05 (d, J=6.9 Hz, 1H), 6.93-6.89 (m, 3H), 6.78-6.69 (m, 2H), 2.49 (s, 6H), 2.42 (s, 3H), 2.17 (s, 3H).

Step B: 8-Bromo-2-isopropyl-7-methyl-[1,2,4]triazolo[1,5-a]pyridine. To a solution of isobutyraldehyde (21.3 µL, 0.23 mmol) in EtOH (0.78 mL) was added a solution of $Na_2S_2O_5$ (25.1 mg, 0.13 mmol) in $H_2O$ (0.1 mL). The reaction was stirred for 5 minutes, and then additional EtOH (0.5 mL) was added. The mixture was allowed to sit in a refrigerator at −20° C. for several hours. The precipitate was collected via vacuum filtration and added at once to a solution of 1,2-diamino-3-bromo-4-methylpyridin-1-ium 2,4,6-trimethylbenzenesulfonate (25.0 mg, 0.062 mmol) in DMF (0.3 mL). The mixture was heated at 130° C. in a sealed microwave vial for 4 hours. After cooling to rt, the reaction was diluted with EtOAc and washed with $H_2O$. The aqueous layer was extracted twice with EtOAc, and the combined organics were washed with brine (×3), dried ($Na_2SO_4$) and filtered. The filtrate was concentrated in vacuo, and the residue purified (FCC, $SiO_2$, 0-50% EtOAc/hexanes) to afford the title compound as a white solid (11.3 mg, 72% yield). MS (ESI): mass calcd. for $C_{10}H_{12}BrN_3$, 253.0; m/z found, 254.1 [M+H]$^+$. $^1$H NMR (400 MHz, CDCl$_3$) δ 8.35 (d, J=6.9 Hz, 1H), 6.82 (d, J=6.9 Hz, 1H), 3.35-3.23 (m, 1H), 2.53 (s, 3H), 1.44 (d, J=7.0 Hz, 6H).

Intermediate 33

8-Chloro-2,7-bis(trifluoromethyl)-[1,2,4]triazolo[1,5-a]pyridine

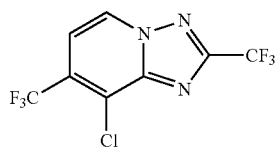

A microwave vial was charged with 8-chloro-7-iodo-2-(trifluoromethyl)-[1,2,4]triazolo[1,5-a]pyridine (Intermediate 19, 300 mg, 0.863 mmol), methyl 2,2-difluoro-2-(fluorosulfonyl)acetate (0.28 mL, 2.16 mmol), CuI (411 mg, 2.16 mmol), DMPU (0.59 mL, 4.89 mmol), and DMF (5.4 mL). The vial was then evacuated and refilled with $N_2$ (×3), then capped and sealed. The reaction was then stirred in a microwave reactor at 130° C. for 30 minutes. After cooling to rt, the mixture was filtered over a pad of Celite®, eluting with MeOH. After concentrating the filtrate, the residue was re-dissolved in a mixture of EtOAc and $H_2O$. The organic layer was washed with sat. aq. $NH_4Cl$, and then the combined aqueous layers extracted with EtOAc (×2). The combined organics were washed with brine (×3), dried ($Na_2SO_4$) and filtered. The filtrate was concentrated in vacuo, and the residue purified (FCC, $SiO_2$, 0-50% EtOAc/hexanes) to afford the title compound as a white solid (171 mg, 68% yield). MS (ESI): mass calcd. for $C_8H_2ClF_6N_3$, 289.0; m/z found, 290.0 $[M+H]^+$. $^1$H NMR (500 MHz, DMSO-$d_6$) δ 9.38-9.31 (m, 1H), 7.80 (d, J=7.3 Hz, 1H).

Intermediate 34

8-Chloro-2-methyl-7-(trifluoromethyl)-[1,2,4]triazolo[1,5-a]pyridine

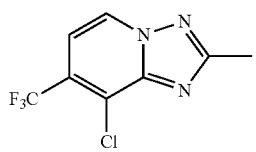

The title compound was prepared in a manner analogous to Intermediate 33 using 8-chloro-7-iodo-2-methyl-[1,2,4]triazolo[1,5-a]pyridine (Intermediate 27). MS (ESI): mass calcd. for $C_8H_5ClF_3N_3$, 235.5; m/z found, 236.1 $[M+H]^+$. $^1$H NMR (400 MHz, DMSO-$d_6$) δ 9.09 (d, 1H), 7.50 (d, J=7.3 Hz, 1H), 2.56 (s, 3H).

Intermediate 35

8-Chloro-2-cyclopropyl-7-(trifluoromethyl)-[1,2,4]triazolo[1,5-a]pyridine

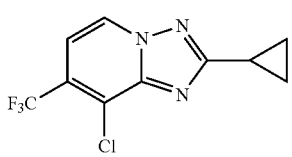

The title compound was prepared in an analogous manner to Intermediate 33 using 8-chloro-2-cyclopropyl-7-iodo-[1,2,4]triazolo[1,5-a]pyridine (Intermediate 26). MS (ESI): mass calcd. for $C_{10}H_7ClF_3N_3$, 261.0; m/z found, 262.0 $[M+H]^+$. $^1$H NMR (500 MHz, DMSO-$d_6$) δ 9.04 (dd, J=7.0, 0.9 Hz, 1H), 7.46 (d, J=7.2 Hz, 1H), 2.28-2.22 (m, 1H), 1.17-1.08 (m, 2H), 1.07-0.98 (m, 2H).

Intermediate 36

8-Chloro-2-ethyl-7-(trifluoromethyl)-[1,2,4]triazolo[1,5-a]pyridine

The title compound is prepared in a manner analogous to Intermediate 33 using 8-chloro-2-ethyl-7-iodo-[1,2,4]triazolo[1,5-a]pyridine (Intermediate 28). MS (ESI): mass calcd. for $C_9H_7ClF_3N_3$, 249.6; m/z found, 250.1 $[M+H]^+$. $^1$H NMR (500 MHz, DMSO-$d_6$) δ 9.10 (d, J=7.1 Hz, 1H), 7.50 (dd, J=7.1, 1.2 Hz, 1H), 2.93 (qd, J=7.5, 1.2 Hz, 2H), 1.35 (td, J=7.6, 1.2 Hz, 3H).

Intermediate 37

8-Chloro-2-isopropyl-7-(trifluoromethyl)-[1,2,4]triazolo[1,5-a]pyridine

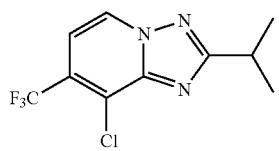 [SMILES: CC(C)c1nc2c(Cl)c(C(F)(F)F)ccn2n1]

The title compound is prepared in a manner analogous to Intermediate 33 using 8-chloro-7-iodo-2-isopropyl-[1,2,4]triazolo[1,5-a]pyridine (Intermediate 30). MS (ESI): mass calcd. for $C_{10}H_9ClF_3N_3$, 263.6; m/z found, 264.0 $[M+H]^+$. $^1$H NMR (500 MHz, DMSO-$d_6$) δ 9.10 (d, J=7.2 Hz, 1H), 7.49 (d, J=7.1 Hz, 1H), 3.25 (dt, J=13.8, 6.9 Hz, 1H), 1.45-1.31 (m, 6H).

Intermediate 38

8-Chloro-7-(difluoromethyl)-2-(trifluoromethyl)-[1,2,4]triazolo[1,5-a]pyridine

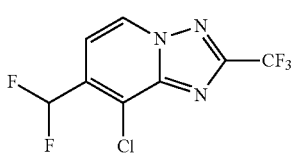 [SMILES: FC(F)c1ccn2nc(C(F)(F)F)nc2c1Cl]

Step A: 8-Chloro-2-(trifluoromethyl)-[1,2,4]triazolo[1,5-a]pyridine-7-carbaldehyde. To a solution of 8-chloro-7-iodo-2-(trifluoromethyl)-[1,2,4]triazolo[1,5-a]pyridine (Intermediate 19, 300 mg, 0.863 mmol) in THF (2.9 mL) at 0° C. was added isopropylmagnesium chloride (2.0 M in THF; 0.52 mL, 1.04 mmol) dropwise. The mixture was stirred at 0° C. for 1.5 h, and then N-formylpiperidine (0.12 mL, 1.04 mmol) was added. The reaction warmed to rt and stirred for 2 h. The mixture was then transferred to a stirring solution of AcOH (1 mL) and subsequently diluted with EtOAc and H$_2$O. The aqueous layer was extracted with EtOAc (×2), and the combined organics washed with sat. aq. NaHCO$_3$ (×3) and brine. After drying over Na$_2$SO$_4$, filtering, and concentrating in vacuo, the residue was purified (FCC, SiO$_2$, 0-100% EtOAc/hexanes) to afford the title compound as a white solid (120 mg, 47% yield). $^1$H NMR (500 MHz, CDCl$_3$) δ 10.61 (d, J=0.9 Hz, 1H), 8.67-8.62 (m, 1H), 7.70 (d, J=7.0 Hz, 1H).

Step B: 8-Chloro-7-(difluoromethyl)-2-(trifluoromethyl)-[1,2,4]triazolo[1,5-a]pyridine. To a solution of 8-chloro-2-(trifluoromethyl)-[1,2,4]triazolo[1,5-a]pyridine-7-carbaldehyde (171 mg, 0.47 mmol) in DCM (10.9 mL) at 0° C. under an N$_2$ atmosphere was added diethylaminosulfur trifluoride (0.22 mL, 1.64 mmol) dropwise via syringe. The mixture was allowed to warm to rt and stirred overnight, before pouring over ice (ca. 25 mL). Sat. aq. NaHCO$_3$ (30 mL) was then added, the mixture stirred vigorously for 5 minutes, and EtOAc (30 mL) added. The aqueous layer was extracted with EtOAc (×2), and the combined organics washed with brine, dried (Na$_2$SO$_4$), filtered, and concentrated. The residue was purified (FCC, SiO$_2$, 0-100% EtOAc/hexanes) to afford the title compound as a white solid (117 mg, 87% yield). MS (ESI): mass calcd. for C$_8$H$_3$ClF$_5$N$_3$, 271.0; m/z found, 272.0 [M+H]$^+$. $^1$H NMR (500 MHz, CDCl$_3$) δ 8.71-8.66 (m, 1H), 7.48 (d, J=7.1 Hz, 1H), 7.12 (t, J=54.0 Hz, 1H).

Intermediate 39

8-Chloro-7-ethyl-2-(trifluoromethyl)-[1,2,4]triazolo[1,5-a]pyridine

Step A: 8-Chloro-2-(trifluoromethyl)-7-vinyl-[1,2,4]triazolo[1,5-a]pyridine. A microwave vial was charged with 8-chloro-7-iodo-2-(trifluoromethyl)-[1,2,4]triazolo[1,5-a]pyridine (Intermediate 19, 60 mg, 0.173 mmol), potassium vinyltrifluoroborate (24.3 mg, 0.181 mmol), Pd(PPh$_3$)$_4$ (10 mg, 5 mol %), saturated aqueous Na$_2$CO$_3$ (0.59 mL), and 1,4-dioxane (2.4 mL). The vial was evacuated and refilled with N$_2$ (×3), then capped and sealed. The reaction was stirred in a microwave reactor at 110° C. for 1 h. The mixture was diluted with EtOAc and H$_2$O, and the aqueous layer was extracted with EtOAc (×2). The combined organics were washed with brine, dried (Na$_2$SO$_4$) and filtered. After concentrating in vacuo, the residue was used directly in the next step without further purification. MS (ESI): mass calcd. for C$_9$H$_5$ClF$_5$N$_3$, 247.0; m/z found, 248.1 [M+H]$^+$. $^1$H NMR (500 MHz, CDCl$_3$) δ 8.52-8.46 (m, 1H), 7.39 (d, J=7.3 Hz, 1H), 7.25-7.19 (m, 1H), 6.04 (d, J=17.6 Hz, 1H), 5.77 (d, J=11.1 Hz, 1H).

Step B: 8-Chloro-7-ethyl-2-(trifluoromethyl)-[1,2,4]triazolo[1,5-a]pyridine. To a solution of 8-chloro-2-(trifluoromethyl)-7-vinyl-[1,2,4]triazolo[1,5-a]pyridine (42.8 mg, 0.173 mmol) in MeOH (1.71 mL) was added 10% palladium on carbon (8.6 mg, 5 mol %). The mixture was stirred under an atmosphere of H$_2$ overnight, then filtered over a pad of Celite®. The filtrate was then concentrated and the residue used directly in the next step without further purification. MS (ESI): mass calcd. for C$_9$H$_7$ClF$_5$N$_3$, 249.0; m/z found, 250.1 [M+H]$^+$.

Intermediate 40

8-Bromo-7-methyl-2-(trifluoromethyl)imidazo[1,2-a]pyridine

To a microwave vial charged with EtOH (2.5 mL) were added 3-bromo-4-methylpyridin-2-amine (250 mg, 1.34 mmol) and 3-bromo-1,1,1-trifluoropropan-2-one (0.28 mL, 2.7 mmol). The vial was capped and heated to 160° C. in the microwave for 60 minutes. The reaction mixture was diluted with H$_2$O and extracted with DCM (×3). The combined organic extracts were dried (MgSO$_4$), filtered, and concentrated. Purification (FCC, SiO$_2$; 0-25% EtOAc/hexanes) provided the title compound as a colorless solid (240 mg, 64% yield). MS (ESI): mass calcd. for C$_9$H$_6$BrF$_3$N$_2$, 278.0; m/z found, 279.0 [M+H]$^+$. $^1$H NMR (400 MHz, CDCl$_3$) δ 8.00 (d, J=6.9 Hz, 1H), 7.90 (d, J=1.1 Hz, 1H), 6.79 (d, J=6.9 Hz, 1H), 2.52 (s, 3H).

Intermediate 41

8-Bromo-2-(tert-butyl)-7-methylimidazo[1,2-a]pyridine

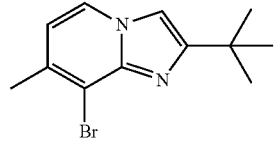

To a microwave vial charged with EtOH (3 mL) were added 3-bromo-4-methylpyridin-2-amine (100 mg, 0.54 mmol), 1-bromo-3,3-dimethylbutan-2-one (0.16 mL, 1.18 mmol), and potassium phosphate (340 mg, 1.60 mmol). The vial was capped and heated to 160° C. in the microwave for 60 minutes. The reaction mixture was diluted with H$_2$O and extracted with EtOAc (×2). The combined organic extracts were washed with brine, dried (MgSO$_4$), filtered, and concentrated. Purification (FCC, SiO$_2$; 0-30% EtOAc/hexanes) provided the title compound as a light yellow oil (105 mg, 74% yield). MS (ESI): mass calcd. for C$_{12}$H$_{15}$BrN$_2$, 266.0;

m/z found, 67.1 [M+H]+. 1H NMR (500 MHz, CDCl3) δ 7.88 (d, J=6.8 Hz, 1H), 7.34 (s, 1H), 6.56 (d, J=6.8 Hz, 1H), 2.45 (s, 3H), 1.41 (s, 9H).

Intermediate 42

8-Bromo-7-methyl-2-phenylimidazo[1,2-a]pyridine

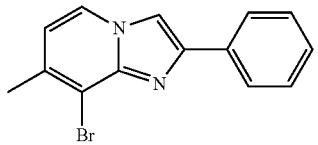 [SMILES: Cc1ccn2cc(-c3ccccc3)nc2c1Br]

To a microwave vial charged with EtOH (2 mL) were added 3-bromo-4-methylpyridin-2-amine (100 mg, 0.54 mmol) and 2-bromo-1-phenylethan-1-one (213 mg, 1.07 mmol). The vial was capped and heated to 160° C. in the microwave for 60 minutes. After cooling to rt, the reaction was diluted with sat. aq. NaHCO3 and extracted with EtOAc (×3). The combined organic extracts were washed with brine, dried (MgSO4), filtered, and concentrated. Purification (FCC, SiO2; 0-25% EtOAc/hexanes) provided the title compound as a light yellow solid (94 mg, 61% yield). MS (ESI): mass calcd. for $C_{14}H_{11}BrN_2$, 286.0; m/z found, 287.0 [M+H]+. 1H NMR (500 MHz, CDCl3) δ 7.99-7.95 (m, 2H), 7.93 (d, J=6.8 Hz, 1H), 7.82 (s, 1H), 7.44-7.39 (m, 2H), 7.34-7.29 (m, 1H), 6.61 (d, J=6.8 Hz, 1H), 2.47 (s, 3H).

Intermediate 43

8-Bromo-2-cyclopropyl-7-methylimidazo[1,2-a]pyridine

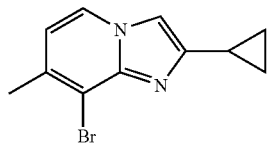

To a microwave vial charged with EtOH (3.0 mL) were added 3-bromo-4-methylpyridin-2-amine (100 mg, 0.535 mmol), 2-bromo-1-cyclopropylethan-1-one (115 μL, 1.176 mmol), and potassium phosphate (340 mg, 1.60 mmol). The vial was capped and the heated to 160° C. in the microwave for 60 minutes. After cooling to rt, additional 2-bromo-1-cyclopropylethan-1-one (120 μL, 1.23 mmol) and potassium phosphate (340 mg, 1.60 mmol) were added. The vial was capped and reaction heated to 160° C. in the microwave for an additional 60 minutes. After cooling to rt, the reaction was diluted with H2O and extracted with EtOAc (×3). The combined organic extracts were washed with brine, dried (MgSO4), filtered, and concentrated. Purification (FCC, SiO2; 0-20% EtOAc/hexanes) provided the title compound as a light orange/yellow solid (36 mg, 27% yield). MS (ESI): mass calcd. for $C_{11}H_{11}BrN_2$, 250.0; m/z found, 251.0 [M+H]+. 1H NMR (500 MHz, CDCl3) δ 7.84 (d, J=6.8 Hz, 1H), 7.24 (s, 1H), 6.57 (d, J=6.8 Hz, 1H), 2.45 (s, 3H), 2.14-2.06 (m, 1H), 1.00-0.94 (m, 2H), 0.85-0.80 (m, 2H).

Intermediate 44

8-Iodo-7-methoxy-2-(trifluoromethyl)imidazo[1,2-a]pyridine

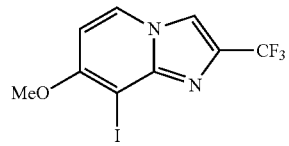 [SMILES: COc1ccn2cc(C(F)(F)F)nc2c1I]

To a microwave vial charged with EtOH (1.0 mL) were added 3-iodo-4-methoxypyridin-2-amine (100 mg, 0.4 mmol) and 3-bromo-1,1,1-trifluoropropan-2-one (83 μL, 2.7 mmol). The vial was capped and the reaction mixture was stirred at rt for 2 h, then heated at 50° C. for 18 h, and then at 100° C. for 3.5 h. The reaction mixture was cooled to rt and concentrated in vacuo. The residue was diluted with sat. aq. NaHCO3 and extracted with DCM (×3). The combined organic extracts were concentrated. Purification (FCC, SiO2; 0-40% EtOAc/hexanes) provided the title compound as an off-white solid (81 mg, 59% yield). MS (ESI): mass calcd. for $C_9H_6IF_3N_2O$, 341.9; m/z found, 343.0 [M+H]+. 1H NMR (500 MHz, CDCl3) δ 8.07 (d, J=7.5 Hz, 1H), 7.92-7.90 (m, 1H), 6.72 (d, J=7.5 Hz, 1H), 4.01 (s, 3H).

Intermediate 45

7-Chloro-8-iodo-2-(trifluoromethyl)imidazo[1,2-a]pyridine

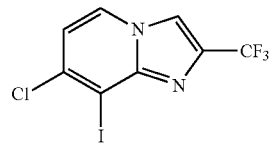 [SMILES: FC(F)(F)c1cn2ccc(Cl)c(I)c2n1]

To a microwave vial charged with EtOH (2.0 mL) were added 4-chloro-3-iodopyridin-2-amine (150 mg, 0.59 mmol) and 3-bromo-1,1,1-trifluoropropan-2-one (122 μL, 1.18 mmol). The vial was capped and the reaction mixture was stirred at rt for 1 h, followed by heating at 100° C. in the microwave for 1 h. After cooling to rt, the reaction mixture was concentrated in vacuo. The residue was diluted with sat. aq. NaHCO3 and extracted with EtOAc (×3). The combined organic extracts were concentrated. Purification (FCC, SiO2; 0-30% EtOAc/hexanes) provided the title compound as an off-white solid (190 mg, 93% yield). MS (ESI): mass calcd. for $C_8H_3ClF_3IN_2$, 345.9; m/z found, 346.9 [M+H]+. 1H NMR (400 MHz, CDCl3) δ 8.07-7.98 (m, 2H), 6.97 (d, J=7.1 Hz, 1H).

Intermediate 46

8-Chloro-7-iodo-2-(trifluoromethyl)imidazo[1,2-a]pyridine

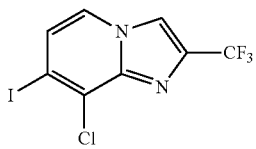 [SMILES: FC(F)(F)c1cn2ccc(I)c(Cl)c2n1]

A microwave vial was charged with Intermediate 10 (3-chloro-4-iodopyridin-2-amine) (144 mg, 0.57 mmol), 3-bromo-1,1,1-trifluoroacetone (0.12 mL, 1.13 mmol), $K_3CO_3$ (78.2 mg, 0.57 mmol), and EtOH (1.14 mL). The reaction was stirred in a microwave reactor at 180° C. for 30 minutes. The reaction was filtered and the filtrate concentrated. The residue was purified by reverse-phase preparative HPLC (XBridge $^{18}C$ OBD column, 5-99% ACN in 20 mM $NH_4OH$) to afford the title compound (72 mg, 37% yield). MS (ESI): mass calcd. for $C_8H_3ClF_3IN_2$, 345.9; m/z found, 346.8 [M+H]$^+$. $^1H$ NMR (400 MHz, CDCl$_3$) δ 7.94 (d, J=0.9 Hz, 1H), 7.84 (d, J=7.1 Hz, 1H), 7.27 (d, J=7.2 Hz, 1H).

Intermediate 47

8-Chloro-2,7-bis(trifluoromethyl)imidazo[1,2-a]pyridine

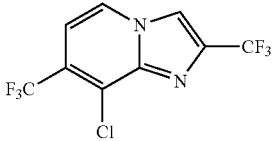

A microwave vial was charged with 8-chloro-7-iodo-2-(trifluoromethyl)imidazo[1,2-a]pyridine (Intermediate 46, 30 mg, 86.6 μmol), methyl 2,2-difluoro-2-(fluorosulfonyl)acetate (27.6 μL, 0.216 mmol), CuI (41.2 mg, 0.216 mmol), DMPU (59.3 μL, 0.49 mmol), and DMF (0.6 mL). The vial was then evacuated and refilled with N$_2$ (×3), then capped and sealed. The reaction was then stirred in a microwave reactor at 130° C. for 30 minutes. After cooling to rt, the mixture was filtered over a pad of Celite®, eluting with EtOAc. After concentrating the filtrate, the residue was re-dissolved in a mixture of EtOAc and H$_2$O. The organic layer was washed with 1N HCl, and then the combined aqueous layers extracted with EtOAc (×2). The combined organics were washed with sat. aq. NH$_4$Cl, followed by brine (×3), dried (Na$_2$SO$_4$), and filtered. The filtrate was concentrated in vacuo, and the residue used without further purification. MS (ESI): mass calcd. for $C_9H_3ClF_6N_2$, 288.0; m/z found, 288.9 [M+H]$^+$.

Intermediate 48

8-Bromo-2,7-bis(trifluoromethyl)imidazo[1,2-c]pyrimidine

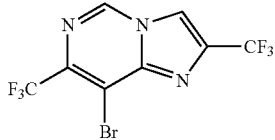 [SMILES: FC(F)(F)c1cn2cnc(C(F)(F)F)c(Br)c2n1]

To a solution of 5-bromo-6-(trifluoromethyl)pyrimidin-4-amine (Intermediate 12, 150 mg, 0.62 mmol) in 1,4 dioxane (0.45 mL) were added 4A° molecular sieves followed by the addition of 3-bromo-1,1,1-trifluoropropan-2-one (0.45 mL, 4.3 mmol). The mixture was heated to 90° C. for 2 h. The reaction mixture was cooled to rt, diluted with sat.aq. NaHCO$_3$, and extracted with EtOAc (×2). The combined organic extracts were washed with brine; dried (Na$_2$SO$_4$), and concentrated in vacuo. Purification (FCC, SiO$_2$; 0-50% EtOAc/hexanes) provided the title compound as off-white solid (143 mg, 69% yield). MS (ESI): mass calcd. for $C_8H_2BrF_6N_3$, 334.0; m/z found, 335.9 [M+H]$^+$.

Intermediate 49

8-Bromo-2-cyclopropyl-7-(trifluoromethyl)imidazo[1,2-c]pyrimidine

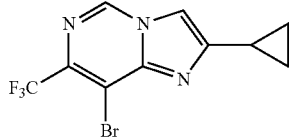 [SMILES: FC(F)(F)c1ncn2cc(C3CC3)nc2c1Br]

The title compound was prepared in a manner analogous to Intermediate 48 using 2-bromo-1-cyclopropylethan-1-one. MS (ESI): mass calcd. for $C_{10}H_7BrF_3N_3$, 306.0; m/z found, 308.0 [M+H]$^+$. $^1H$ NMR (400 MHz, DMSO-d$_6$) δ 9.39 (s, 1H), 8.12 (s, 1H), 2.21-2.13 (m, 1H), 1.07-0.97 (m, 2H), 0.94-0.87 (m, 2H).

Intermediate 50

8-Bromo-2-ethyl-7-(trifluoromethyl)imidazo[1,2-c]pyrimidine

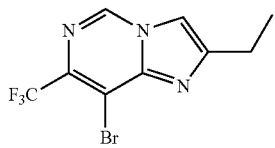 [SMILES: CCc1cn2cnc(C(F)(F)F)c(Br)c2n1]

The title compound was prepared in a manner analogous to Intermediate 48 using 1-bromobutan-2-one. MS (ESI): mass calcd. for $C_9H_7BrF_3N_3$, 294.0; m/z found, 296.0 [M+H]$^+$.

Intermediate 51

8-Bromo-2-isopropyl-7-(trifluoromethyl)imidazo[1,2-c]pyrimidine

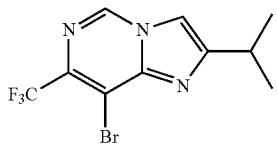 [SMILES: CC(C)c1cn2cnc(C(F)(F)F)c(Br)c2n1]

The title compound was prepared in a manner analogous to Intermediate 48 using 1-bromo-3-methylbutan-2-one. MS (ESI): mass calcd. for $C_{10}H_9BrF_3N_3$, 308.1; m/z found, 309.9 [M+H]$^+$.

Intermediate 52

8-Bromo-7-isopropyl-2-(trifluoromethyl)imidazo[1,2-c]pyrimidine

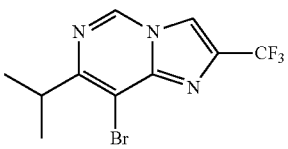 [SMILES: CC(C)c1ncn2cc(C(F)(F)F)nc2c1Br]

The title compound was prepared in a manner analogous to Intermediate 48 using 5-bromo-6-isopropylpyrimidin-4-amine (Intermediate 13). MS (ESI): mass calcd. for $C_{10}H_9BrF_3N_3$, 308.1; m/z found, 309.0 [M+H]$^+$.

Intermediate 53

8-Bromo-2-(difluoromethyl)-7-isopropylimidazo[1,2-c]pyrimidine

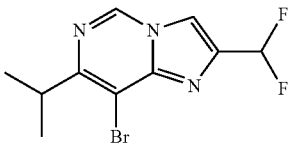 [SMILES: CC(C)c1ncn2cc(C(F)F)nc2c1Br]

The title compound was prepared in a manner analogous to Intermediate 48 using 5-bromo-6-isopropylpyrimidin-4-amine (Intermediate 13) and 3-bromo-1,1-difluoropropan-2-one (Intermediate 18) and the reaction mixture was heated to 60° C. for 15 h. MS (ESI): mass calcd. for $C_{10}H_{10}BrF_2N_3$, 290.1; m/z found, 291.9 [M+H]$^+$.

Intermediate 54

8-Bromo-7-ethyl-2-(trifluoromethyl)imidazo[1,2-c]pyrimidine

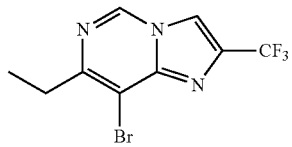 [SMILES: CCc1ncn2cc(C(F)(F)F)nc2c1Br]

The title compound was prepared in a manner analogous to Intermediate 48 using 5-bromo-6-ethylpyrimidin-4-amine (Intermediate 14). MS (ESI): mass calcd. for $C_9H_7BrF_3N_3$, 294.0; m/z found, 296.0 [M+H]$^+$. $^1$H NMR (400 MHz, DMSO-$d_6$) δ 9.37 (s, 1H), 8.67 (q, J=1.2 Hz, 1H), 2.92 (q, J=7.6 Hz, 2H), 1.29-1.19 (m, 3H).

Intermediate 55

8-Bromo-2-(difluoromethyl)-7-ethylimidazo[1,2-c]pyrimidine

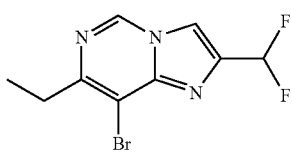

The title compound was prepared in a manner analogous to Intermediate 48 using 5-bromo-6-ethylpyrimidin-4-amine (Intermediate 14) and 3-Bromo-1,1-difluoropropan-2-one (Intermediate 18). MS (ESI): mass calcd. for $C_9H_8BrF_2N_3$, 276.0; m/z found, 277.0 [M+H]$^+$. $^1$H NMR (400 MHz, DMSO-$d_6$) δ 9.37 (s, 1H), 8.43-8.30 (m, 1H), 7.37-7.00 (m, 1H), 2.91 (q, J=7.6 Hz, 2H), 1.24 (t, J=7.5 Hz, 3H).

Intermediate 56

8-Bromo-7-methyl-2-(trifluoromethyl)imidazo[1,2-c]pyrimidine

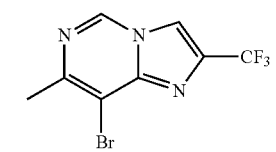

The title compound was prepared in a manner analogous to Intermediate 48 using 5-bromo-6-methylpyrimidin-4-amine (Intermediate 15). MS (ESI): mass calcd. for $C_8H_5BrF_3N_3$, 280.0; m/z found, 282.0 [M+H]$^+$. $^1$H NMR (400 MHz, DMSO-$d_6$) δ 9.34 (s, 1H), 8.67 (q, J=1.2 Hz, 1H), 2.60 (s, 3H).

Intermediate 57

8-Bromo-7-cyclopropyl-2-(trifluoromethyl)imidazo[1,2-c]pyrimidine

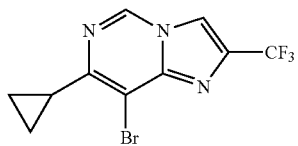 [SMILES: FC(F)(F)c1cn2cnc(C3CC3)c(Br)c2n1]

The title compound was prepared in a manner analogous to Intermediate 48 using 5-bromo-6-cyclopropylpyrimidin-4-amine (Intermediate 16). MS (ESI): mass calcd. for $C_{10}H_7BrF_3N_3$, 306.0; m/z found, 308.0 [M+H]$^+$.

Intermediate 58

8-Bromo-7-cyclopropyl-2-(difluoromethyl)imidazo[1,2-c]pyrimidine

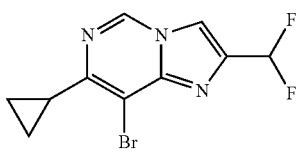 [SMILES: FC(F)c1cn2cnc(C3CC3)c(Br)c2n1]

The title compound was prepared in a manner analogous to Intermediate 48 using 5-bromo-6-cyclopropylpyrimidin-4-amine (Intermediate 16) and 3-bromo-1,1-difluoropropan-2-one (Intermediate 18). MS (ESI): mass calcd. for $C_{10}H_8BrF_2N_3$, 288.0; m/z found, 290.0 [M+H]$^+$.

Intermediate 59

8-Bromo-7-cyclopropyl-5-methyl-2-(trifluoromethyl)imidazo[1,2-c]pyrimidine

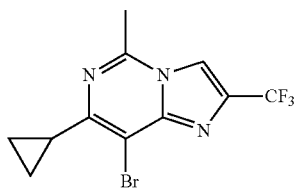 [SMILES: Cc1nc(C2CC2)c(Br)c2nc(C(F)(F)F)cn12]

The title compound was prepared in a manner analogous to Intermediate 48 using 5-bromo-6-cyclopropyl-2-methylpyrimidin-4-amine (Intermediate 17). MS (ESI): mass calcd. for $C_{11}H_9BrF_3N_3$, 320.1; m/z found, 322.0 [M+H]$^+$. $^1$H NMR (400 MHz, DMSO-d$_6$) δ 8.69 (q, J=1.2 Hz, 1H), 2.73 (s, 3H), 2.50-2.44 (m, 1H), 1.12-1.02 (m, 4H).

Intermediate 60

8-Bromo-7-cyclopropyl-2-(difluoromethyl)-5-methylimidazo[1,2-c]pyrimidine

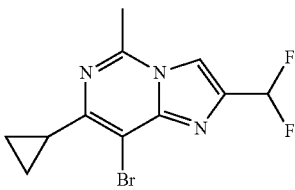 [SMILES: Cc1nc(C2CC2)c(Br)c2nc(C(F)F)cn12]

The title compound was prepared in a manner analogous to Intermediate 48 using 5-bromo-6-cyclopropyl-2-methylpyrimidin-4-amine (Intermediate 17) and 3-bromo-1,1-difluoropropan-2-one (Intermediate 18). MS (ESI): mass calcd. for $C_{11}H_{10}BrF_2N_3$, 302.1; m/z found, 304.0 [M+H]$^+$. $^1$H NMR (400 MHz, DMSO-d$_6$) δ 8.34 (dd, J=2.2, 1.7 Hz, 1H), 7.35-6.98 (m, 1H), 2.72 (s, 3H), 2.49-2.43 (m, 1H), 1.10-1.01 (m, 4H).

Intermediate 61

8-Bromo-3-chloro-2-cyclopropyl-7-(trifluoromethyl)imidazo[1,2-c]pyrimidine

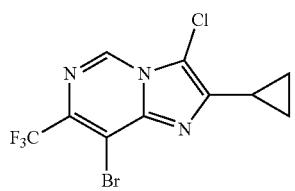 [SMILES: Fc1c(C2CC2)nc2c(Br)c(C(F)(F)F)ncn12]

To a solution of 8-bromo-2-cyclopropyl-7-(trifluoromethyl)imidazo[1,2-c]pyrimidine (Intermediate 49, 113 mg, 0.37 mmol) in DCM (3.5 mL) was added N-chlorosuccinimide (198 mg, 1.5 mmol) and the mixture was heated to 40° C. for 20 h. After cooling to rt, the crude reaction mixture was transferred to a silica gel column and purified by flash chromatography (0-50% EtOAc/hexanes) to afford the title compound as white solid (88 mg, 70% yield). MS (ESI): mass calcd. for $C_{10}H_6BrClF_3N_3$, 340.5; m/z found, 341.8 [M+H]$^+$.

Intermediate 62

8-Bromo-2-cyclopropyl-3-fluoro-7-(trifluoromethyl)imidazo[1,2-c]pyrimidine

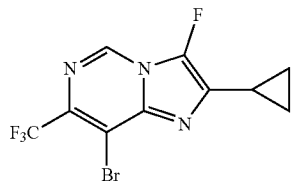

To a solution of 8-bromo-2-cyclopropyl-7-(trifluoromethyl)imidazo[1,2-c]pyrimidine (Intermediate 49, 63 mg, 0.23 mmol) in ACN (3.0 mL) was added Selectfluor® (80 mg, 0.23 mmol) and the mixture was stirred at rt for 1 h. The crude mixture was concentrated to dryness, diluted with water, and extracted with DCM (×2). The combined organics were washed with brine, dried ($Na_2SO_4$), and filtered. The crude reaction mixture was purified (FCC, $SiO_2$; 0-50% EtOAc/hexanes) to afford the title compound as white solid (30.5 mg, 46% yield). MS (ESI): mass calcd. for $C_{10}H_6BrClF_4N_3$, 324.0; m/z found, 326.0 [M+H]$^+$. $^1$H NMR (400 MHz, DMSO-$d_6$) δ 9.30 (d, J=2.2 Hz, 1H), 2.18-2.10 (m, 1H), 1.12-1.05 (m, 2H), 1.00-0.95 (m, 2H).

Intermediate 63

8-Chloro-2-(difluoromethyl)-7-(trifluoromethyl)imidazo[1,2-a]pyridine

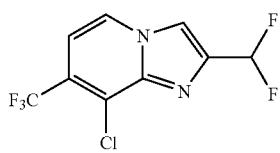 [SMILES: FC(F)c1cn2ccc(C(F)(F)F)c(Cl)c2n1]

The title compound was prepared in a manner analogous to Intermediate 48 using 3-chloro-4-(trifluoromethyl)pyridine-2-amine and 3-bromo-1,1-difluoropropan-2-one (Intermediate 18). MS (ESI): mass calcd. for $C_9H_4ClF_5N_2$, 270.0; m/z found, 271.0 [M+H]$^+$. $^1$H NMR (500 MHz, DMSO-$d_6$) δ 8.80-8.75 (m, 1H), 8.59-8.54 (m, 1H), 7.39-7.34 (m, 1H), 7.26 (t, J=54.4 Hz, 1H).

Intermediate 64

8-Chloro-2-methyl-7-(trifluoromethyl)imidazo[1,2-a]pyridine

The title compound was prepared in a manner analogous to Intermediate 48 using 3-chloro-4-(trifluoromethyl)pyridine-2-amine and 1-bromopropane-2-one. MS (ESI): mass calcd. for $C_9H_6ClF_3N_2$, 234.0; m/z found, 235.0 [M+H]$^+$.

Intermediate 65

8-Chloro-2-ethyl-7-(trifluoromethyl)imidazo[1,2-a]pyridine

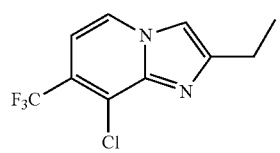 [SMILES: CCc1cn2ccc(C(F)(F)F)c(Cl)c2n1]

The title compound was prepared in a manner analogous to Intermediate 48 using 3-chloro-4-(trifluoromethyl)pyridine-2-amine and 1-bromobutan-2-one. MS (ESI): mass calcd. for $C_{10}H_8ClF_3N_2$, 248.0; m/z found, 249.1 [M+H]$^+$.

Intermediate 66

8-Chloro-2-isopropyl-7-(trifluoromethyl)imidazo[1,2-a]pyridine

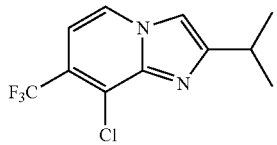 [SMILES: CC(C)c1cn2ccc(C(F)(F)F)c(Cl)c2n1]

The title compound was prepared in a manner analogous to Intermediate 48 using 3-chloro-4-(trifluoromethyl)pyridine-2-amine and 1-bromo3-methylbutan-2-one. MS (ESI): mass calcd. for $C_{11}H_{10}ClF_3N_2$, 262.1; m/z found, 263.1 [M+H]$^+$.

Intermediate 67

8-Chloro-2-cyclopropyl-7-(trifluoromethyl)imidazo[1,2-a]pyridine

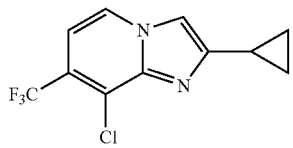 [SMILES: FC(F)(F)c1ccn2cc(C3CC3)nc2c1Cl]

The title compound was prepared in a manner analogous to Intermediate 48 using 3-chloro-4-(trifluoromethyl)pyridine-2-amine and 2-bromo-1-cyclopropylethan-1-one. MS (ESI): mass calcd. for $C_{11}H_8ClF_3N_2$, 260.0; m/z found, 261.1 [M+H]$^+$.

Example 1

8-(7-Chloro-1H-indazol-5-yl)-2-(difluoromethyl)-7-(trifluoromethyl)-[1,2,4]triazolo[1,5-a]pyridine

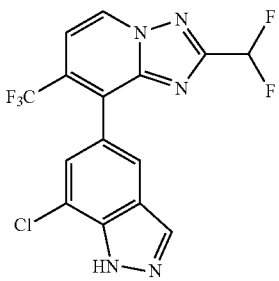

A microwave vial was charged with 8-chloro-2-(difluoromethyl)-7-(trifluoromethyl)-[1,2,4]triazolo[1,5-a]pyridine (Intermediate 25, 29 mg, 0.107 mmol), 7-chloro-5-(4,4,5,5-tetramethyl-1,3,2-dioxaborolan-2-yl)-1H-indazole (Intermediate 1, 35.7 mg, 0.128 mmol), Pd(dppf)Cl$_2$—CH$_2$Cl$_2$ (10 mol %), sat. aq. Na$_2$CO$_3$ (0.37 mL), and 1,4-dioxane (1.5 mL). The vial was evacuated and refilled with N$_2$ (×3), then capped and sealed. The reaction was stirred at 90° C. for 17 h, and then cooled to rt. The mixture was then diluted with EtOAc, and washed with H$_2$O. The aqueous layer was extracted with EtOAc (×2), and the combined organics were washed with brine, dried (Na$_2$SO$_4$), and filtered. After concentrating the filtrate in vacuo, the residue was purified by flash column chromatography (SiO$_2$; 0-50% EtOAc/hexanes) to afford the title compound as a white solid (30.7 mg, 74% yield). MS (ESI): mass calcd. for C$_{15}$H$_7$ClF$_5$N$_5$, 387.0; m/z found, 388.0 [M+H]$^+$. $^1$H NMR (600 MHz, DMSO-d$_6$) δ 13.85 (s, 1H), 9.31 (d, J=7.2 Hz, 1H), 8.32 (s, 1H), 7.87 (s, 1H), 7.73 (d, J=7.3 Hz, 1H), 7.59 (s, 1H), 7.31 (t, J=52.7 Hz, 1H).

Example 2

7-Chloro-8-(7-methyl-1H-indazol-5-yl)-2-(trifluoromethyl)-[1,2,4]triazolo[1,5-a]pyridine

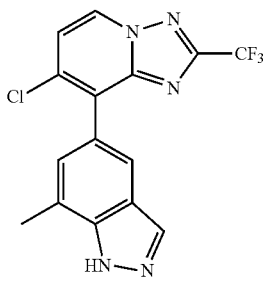 [SMILES: Cc1cc(-c2c(Cl)ccn3nc(C(F)(F)F)nc23)cc2cn[nH]c12]

The title compound was prepared in a manner analogous to Example 1 using 7-chloro-8-iodo-2-(trifluoromethyl)-[1,2,4]triazolo[1,5-a]pyridine (Intermediate 20) and 7-methyl-5-(4,4,5,5-tetramethyl-1,3,2-dioxaborolan-2-yl)-1H-indazole (Intermediate 2), and Pd(PPh$_3$)$_4$ in a microwave reactor at 110° C. for 45 min. MS (ESI): mass calcd. for C$_{15}$H$_9$ClF$_3$N$_5$, 351.0; m/z found, 352.0 [M+H]$^+$. $^1$H NMR (600 MHz, DMSO-d$_6$) δ 13.39 (s, 1H), 9.16 (d, J=7.3 Hz, 1H), 8.20 (s, 1H), 7.78 (s, 1H), 7.69 (d, J=7.3 Hz, 1H), 7.26 (s, 1H), 2.59 (s, 3H).

Example 3

6-(2,7-Bis(trifluoromethyl)-[1,2,4]triazolo[1,5-a]pyridin-8-yl)benzo[d]thiazol-2(3H)-one

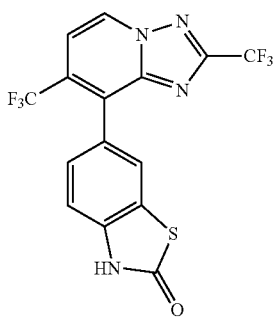 [SMILES: O=c1[nH]c2ccc(-c3c(C(F)(F)F)ccn4nc(C(F)(F)F)nc34)cc2s1]

Step A: 6-(2,7-Bis(trifluoromethyl)-[1,2,4]triazolo[1,5-a]pyridin-8-yl)-3-((2-(trimethylsilyl)ethoxy)methyl)benzo[d]thiazol-2(3H)-one. The title compound was prepared in a manner analogous to Example 1 using 8-chloro-2,7-bis(trifluoromethyl)-[1,2,4]triazolo[1,5-a]pyridine (Intermediate 33) and 6-(4,4,5,5-tetramethyl-1,3,2-dioxaborolan-2-yl)-3-((2-(trimethylsilyl)ethoxy)methyl)benzo[d]thiazol-2(3H)-one (Intermediate 9) in a microwave reactor at 110° C. for 30 min. MS (ESI): mass calcd. for C$_{21}$H$_{20}$F$_6$N$_4$O$_2$SSi, 534.1; m/z found, 535.1 [M+H]$^+$.

Step B: 6-(2,7-Bis(trifluoromethyl)-[1,2,4]triazolo[1,5-a]pyridin-8-yl)benzo[d]thiazol-2(3H)-one. To a solution of 6-(2,7-bis(trifluoromethyl)-[1,2,4]triazolo[1,5-a]pyridin-8-yl)-3-((2-(trimethylsilyl)ethoxy)methyl)benzo[d]thiazol-2 (3H)-one (36.9 mg, 69.1 μmol) in DCM (1.2 mL) was added TFA (0.56 mL), and the mixture stirred at rt for 30 minutes. The solvent was then removed in vacuo, and the residue dissolved in a 2 M solution of NH$_3$ in MeOH (1 mL). The mixture was stirred for 1 hour, the solvent removed in vacuo, and the residue purified by reverse-phase preparative HPLC (XBridge $^{18}$C OBD column, 5-99% ACN in 20 mM NH$_4$OH) to afford the title compound (14.5 mg, 52% yield). MS (ESI): mass calcd. for C$_{15}$H$_6$F$_6$N$_4$OS, 404.0; m/z found, 405.0 [M+H]$^+$. $^1$H NMR (600 MHz, DMSO-d$_6$) δ 12.17 (s, 1H), 9.36 (d, J=7.3 Hz, 1H), 7.82 (d, J=7.3 Hz, 1H), 7.68 (d, J=1.5 Hz, 1H), 7.35 (dd, J=8.3, 1.7 Hz, 1H), 7.27 (d, J=8.2 Hz, 1H).

Example 4

2-Cyclobutyl-7-(4-fluorophenyl)-8-(7-methyl-1H-indazol-5-yl)-[1,2,4]triazolo[1,5-a]pyridine

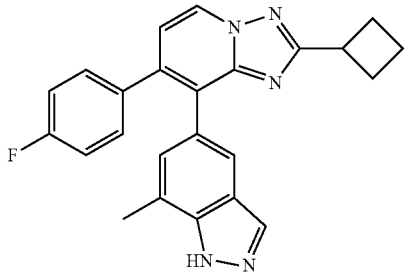 [SMILES: Cc1cc(-c2c(-c3ccc(F)cc3)ccn3nc(C4CCC4)nc23)cc2cn[nH]c12]

Step A: 8-Chloro-2-cyclobutyl-7-(4-fluorophenyl)-[1,2,4]triazolo[1,5-a]pyridine. A microwave vial was charged with 8-chloro-2-cyclobutyl-7-iodo-[1,2,4]triazolo[1,5-a]pyridine (Intermediate 29, 36 mg, 0.108 mmol), 4-fluorophenylboronic acid (15.9 mg, 0.113 mmol), Pd(PPh$_3$)$_4$ (6.3 mg, 5 mol %), sat. aq. Na$_2$CO$_3$ (0.37 mL), and 1,4-dioxane (1.5 mL). The vial was evacuated under vacuum and refilled with N$_2$ (×3), then capped and sealed. The mixture was then stirred in a microwave reactor at 110° C. for 45 minutes.

Step B: 2-Cyclobutyl-7-(4-fluorophenyl)-8-(7-methyl-1H-indazol-5-yl)-[1,2,4]triazolo[1,5-a]pyridine. In the same vial as Step A, 7-methyl-5-(4,4,5,5-tetramethyl-1,3,2-dioxaborolan-2-yl)-1H-indazole (Intermediate 2, 41.8 mg, 0.162 mmol) and XPhos-Pd-G2 precatalyst (7.6 mg, 9 mol %) were added at rt, and the head space was purged with N$_2$. The vial was capped and stirred in a microwave reactor at 150° C. for 45 minutes. After cooling to rt, the mixture was then diluted with EtOAc, and washed with H$_2$O. The aqueous layer was extracted with EtOAc (2×), and the combined organics were washed with brine, dried (Na$_2$SO$_4$) and filtered. After concentrating the filtrate in vacuo, the residue was purified (FCC, SiO$_2$, 0-50% EtOAc/hexanes) to afford title compound as a white solid (21 mg, 49% yield). MS (ESI): mass calcd. for C$_{24}$H$_{20}$FN$_5$, 397.2; m/z found, 398.3 [M+H]$^+$. $^1$H NMR (600 MHz, DMSO-d$_6$) δ 13.20 (s, 1H), 8.90 (d, J=7.0 Hz, 1H), 8.04 (s, 1H), 7.52 (s, 1H), 7.26-7.22 (m, 2H), 7.20 (d, J=7.0 Hz, 1H), 7.09 (t, J=8.9 Hz, 2H), 6.98 (s, 1H), 3.77-3.65 (m, 1H), 2.42 (s, 3H), 2.36-2.27 (m, 4H), 2.09-1.97 (m, 1H), 1.93-1.85 (m, 1H).

Example 5

6-(7-(4-Fluorophenyl)-2-(trifluoromethyl)-[1,2,4]triazolo[1,5-a]pyridin-8-yl)benzo[d]thiazol-2(3H)-one

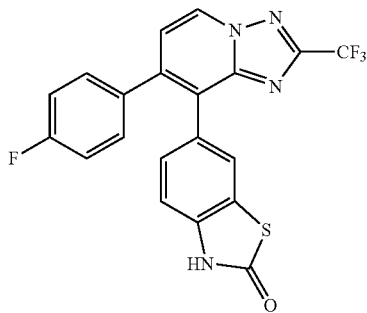 [SMILES: O=c1[nH]c2ccc(-c3c(-c4ccc(F)cc4)ccn4nc(C(F)(F)F)nc34)cc2s1]

Step A: 6-(7-(4-Fluorophenyl)-2-(trifluoromethyl)-[1,2,4]triazolo[1,5-a]pyridin-8-yl)-3-((2-(trimethylsilyl)ethoxy)methyl)benzo[d]thiazol-2(3H)-one. The title compound was prepared in an analogous manner to Example 4 using 8-chloro-7-iodo-2-(trifluoromethyl)-[1,2,4]triazolo[1,5-a]pyridine (Intermediate 19) in Step A and 6-(4,4,5,5-tetramethyl-1,3,2-dioxaborolan-2-yl)-3-((2-(trimethylsilyl)ethoxy)methyl)benzo[d]thiazol-2(3H)-one (Intermediate 9) in Step B in a microwave reactor at 110° C. for 1 h. MS (ESI): mass calcd. for C$_{26}$H$_{24}$F$_4$N$_4$O$_2$SSi, 560.1; m/z found, 561.2 [M+H]$^+$.

Step B: 6-(7-(4-Fluorophenyl)-2-(trifluoromethyl)-[1,2,4]triazolo[1,5-a]pyridin-8-yl)benzo[d]thiazol-2(3H)-one. To a solution of 6-(7-(4-fluorophenyl)-2-(trifluoromethyl)-[1,2,4]triazolo[1,5-a]pyridin-8-yl)-3-((2-(trimethylsilyl)ethoxy)methyl)benzo[d]thiazol-2(3H)-one (48.3 mg, 86.3 μmol) in DCM (1.4 mL) was added TFA (0.7 mL), and the mixture stirred at rt for 1 h. The solvent was then removed in vacuo, and the residue dissolved in a 2 M solution of NH$_3$ in MeOH (1 mL). The mixture was stirred overnight, the solvent removed in vacuo, and the residue purified by reverse-phase preparative HPLC (XBridge $^{18}$C OBD column, 5-99% ACN in 20 mM NH$_4$OH) to afford the title compound (19.4 mg, 52% yield). MS (ESI): mass calcd. for C$_{20}$H$_{10}$F$_4$N$_4$OS, 430.1; m/z found, 431.0 [M+H]$^+$. $^1$H NMR (600 MHz, DMSO-d$_6$) δ 9.15 (d, J=7.1 Hz, 1H), 7.54-7.50 (m, 2H), 7.32-7.28 (m, 2H), 7.19 (t, J=8.9 Hz, 2H), 7.07 (d, J=8.1 Hz, 1H), 7.03 (d, J=8.1 Hz, 1H).

Example 6

7-Cyclopentyl-8-(7-methyl-1H-indazol-5-yl)-2-(trifluoromethyl)-[1,2,4]triazolo[1,5-a]pyridine

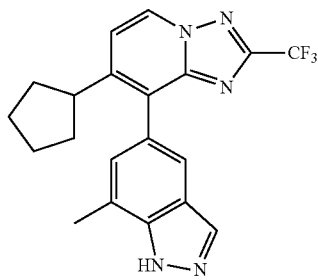 [SMILES: Cc1cc(-c2c(C3CCCC3)ccn3nc(C(F)(F)F)nc23)cc2cn[nH]c12]

Step A: 7-(Cyclopent-1-en-1-yl)-8-(7-methyl-1H-indazol-5-yl)-2-(trifluoromethyl)-[1,2,4]triazolo[1,5-a]pyridine. The title compound was prepared in an analogous manner to Example 4 using 8-chloro-7-iodo-2-(trifluoromethyl)-[1,2,4]triazolo[1,5-a]pyridine (Intermediate 19) and cyclopenten-1-ylboronic acid in Step A. MS (ESI): mass calcd. for C$_{20}$H$_{16}$F$_3$N$_5$, 383.1; m/z found, 384.2 [M+H]$^+$.

Step B: 7-Cyclopentyl-8-(7-methyl-1H-indazol-5-yl)-2-(trifluoromethyl)-[1,2,4]triazolo[1,5-a]pyridine. To a solution of 7-(cyclopent-1-en-1-yl)-8-(7-methyl-1H-indazol-5-yl)-2-(trifluoromethyl)-[1,2,4]triazolo[1,5-a]pyridine (16.8 mg, 0.044 mmol) in MeOH (0.83 mL) was added 20% palladium hydroxide on carbon (2 mg, 0.014 mmol The mixture was stirred under an atmosphere of H$_2$ for 1.5 h, and then filtered over a pad of Celite®. The filtrate was then concentrated and purified by reverse-phase HPLC (XBridge $^{18}$C OBD column, 5-99% ACN in 20 mM NH$_4$OH) to afford the title compound (11.9 mg, 70% yield). MS (ESI): mass calcd. for C$_{20}$H$_{18}$F$_3$N$_5$, 385.1; m/z found, 386.1 [M+H]$^+$. $^1$H NMR (400 MHz, CDCl$_3$) δ 10.90 (bs, 1H), 8.00 (s, 1H), 7.94-7.82 (m, 1H), 7.81-7.70 (m, 1H), 7.57 (d, J=1.4 Hz, 1H), 7.16-7.06 (m, 1H), 3.03-2.86 (m, 1H), 2.09-1.51 (m, 8H).

Example 7

7-(Azetidin-1-yl)-8-(7-methyl-1H-indazol-5-yl)-2-(trifluoromethyl)-[1,2,4]triazolo[1,5-a]pyridine

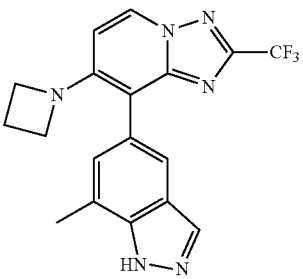 [SMILES: Cc1cc(-c2c(N3CCC3)ccn3nc(C(F)(F)F)nc23)cc2cn[nH]c12]

A microwave vial was charged with 7-chloro-8-(7-methyl-1H-indazol-5-yl)-2-(trifluoromethyl)-[1,2,4]triazolo[1,5-a]pyridine (Example 2, 10 mg, 28.4 μmol), azetidine (3.8 μL, 56.9 μmol), RuPhos-Pd-G3 precatalyst (2.4 mg, 10 mol %), sodium tert-butoxide (8.2 mg, 85.3 μmol), and toluene (0.57 mL; degassed beforehand by bubbling N₂ for 30 minutes). The vial was evacuated and refilled with N₂ (×3), then capped and sealed. The reaction was stirred in a microwave reactor at 150° C. for 1 h. After cooling to rt, BrettPhos-Pd-G3 precatalyst (2.6 mg, 10 mol %), additional azetidine (3.8 µL, 56.9 µmol), and more t-BuONa (8.2 mg, 85.3 µmol) were added, and the reaction was heated in a microwave reactor at 150° C. for 1 h. After cooling to rt, the mixture was then diluted with EtOAc, and washed with H₂O. The aqueous layer was extracted with EtOAc (×2), and the combined organics were washed with brine, dried (Na₂SO₄) and filtered. After concentrating the filtrate in vacuo, the residue was purified by reverse-phase preparative HPLC (XBridge ¹⁸C OBD column, 5-99% ACN in 20 mM NH₄OH), followed by preparative TLC (50% EtOAc/hex) to afford the title compound (1.5 mg, 14% yield). MS (ESI): mass calcd. for $C_{18}H_{15}F_3N_6$, 372.1; m/z found, 373.2 [M+H]⁺. ¹H NMR (600 MHz, DMSO-d₆) δ 13.18 (s, 1H), 8.74 (d, J=7.6 Hz, 1H), 8.10 (s, 1H), 7.59 (s, 1H), 7.15 (t, J=1.2 Hz, 1H), 6.71 (d, J=7.6 Hz, 1H), 3.62 (t, J=7.5 Hz, 4H), 2.56 (s, 3H), 2.06 (p, J=7.4 Hz, 2H).

Example 8

7-(3-Fluoroazetidin-1-yl)-8-(7-methyl-1H-indazol-5-yl)-2-(trifluoromethyl)-[1,2,4]triazolo[1,5-a]pyridine

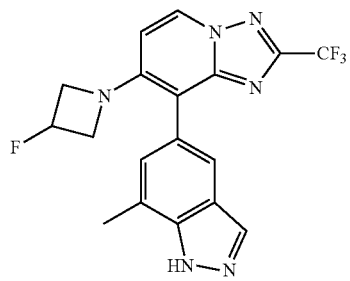 [SMILES: Cc1cc(-c2c(N3CC(F)C3)ccn3nc(C(F)(F)F)nc23)cc2cn[nH]c12]

Step A: 7-Chloro-8-(7-methyl-1-((2-(trimethylsilyl)ethoxy)methyl)-1H-indazol-5-yl)-2-(trifluoromethyl)-[1,2,4]triazolo[1,5-a]pyridine. To a suspension of 7-chloro-8-(7-methyl-1H-indazol-5-yl)-2-(trifluoromethyl)-[1,2,4]triazolo[1,5-a]pyridine (Example 2, 630 mg, 1.79 mmol) in THF (6.3 mL) at 0° C. was added NaH (60% dispersion in mineral oil; 107 mg, 2.69 mmol) portion wise, waiting for effervescence to subside between additions. The reaction mixture was maintained at 0° C. for 20 minutes, and then 2-(trimethylsilyl)ethoxymethyl chloride (0.32 mL, 1.79 mmol) was added dropwise via syringe. The reaction mixture was allowed to warm to rt and stirred for an additional hour. The reaction was diluted with EtOAc and quenched slowly with H₂O. The aqueous layer was extracted with EtOAc (×2), and the combined organics were washed with brine, dried (Na₂SO₄) and filtered. The filtrate was concentrated in vacuo and the residue purified (FCC, SiO₂, 0-20% EtOAc/hexanes) to obtain the title compound as a white foam (447 mg, 52% yield). MS (ESI): mass calcd. for $C_{21}H_{23}ClF_3N_5OSi$, 481.1; m/z found, 482.1 [M+H]⁺.

Step B: 7-(3-Fluoroazetidin-1-yl)-8-(7-methyl-1-((2-(trimethylsilyl)ethoxy)methyl)-1H-indazol-5-yl)-2-(trifluoromethyl)-[1,2,4]triazolo[1,5-a]pyridine.

Method A: A microwave vial was charged with 7-chloro-8-(7-methyl-1-((2-(trimethylsilyl)ethoxy)methyl)-1H-indazol-5-yl)-2-(trifluoromethyl)-[1,2,4]triazolo[1,5-a]pyridine (20 mg, 41.5 µmol), 3-fluoroazetidine hydrochloride (6.9 mg, 62.2 µmol), RuPhos-Pd-G3 pre-catalyst (3.5 mg, 10 mol %), sodium tert-butoxide (16.0 mg, 166 µmol), and 1,4-dioxane (0.67 mL). The vial was evacuated and refilled with N₂ (×3), then capped and sealed. The reaction was then stirred in a microwave reactor at 130° C. for 1 h. The mixture was then diluted with EtOAc and H₂O, and the aqueous layer extracted with EtOAc (×2). The combined organics were washed with brine, dried (Na₂SO₄), and filtered. The filtrate was concentrated in vacuo and the residue used directly in the next step without further purification. MS (ESI): mass calcd. for $C_{24}H_{28}F_4N_6OSi$, 520.2; m/z found, 521.1 [M+H]⁺.

Step C: 7-(3-Fluoroazetidin-1-yl)-8-(7-methyl-1H-indazol-5-yl)-2-(trifluoromethyl)-[1,2,4]triazolo[1,5-a]pyridine. To a solution of 7-(3-fluoroazetidin-1-yl)-8-(7-methyl-1-((2-(trimethylsilyl)ethoxy)methyl)-1H-indazol-5-yl)-2-(trifluoromethyl)-[1,2,4]triazolo[1,5-a]pyridine (65 mg, 0.125 mmol) in DCM (2 mL) was added TFA (1 mL, 13.2 mmol). The reaction was stirred at room temperature for 1 hour, then the solvent removed in vacuo, and the residue purified by reverse-phase preparative HPLC (XBridge ¹⁸C OBD column, 5-99% ACN in 20 mM NH₄OH), to obtain the title compound as a white solid (8 mg, 16% yield). MS (ESI): mass calcd. for $C_{18}H_{14}F_4N_6$, 390.1; m/z found, 391.0 [M+H]⁺. ¹H NMR (600 MHz, DMSO-d₆) δ 13.27 (s, 1H), 8.81 (d, J=7.6 Hz, 1H), 8.12 (s, 1H), 7.62 (s, 1H), 7.16 (s, 1H), 6.80 (d, J=7.6 Hz, 1H), 5.31-5.12 (m, 1H), 3.99-3.86 (m, 2H), 3.74-3.60 (m, 2H), 2.57 (s, 3H).

Example 9

2-Cyclopentyl-7-(4-fluorophenyl)-8-(7-methyl-1H-indazol-5-yl)-[1,2,4]triazolo[1,5-a]pyridine

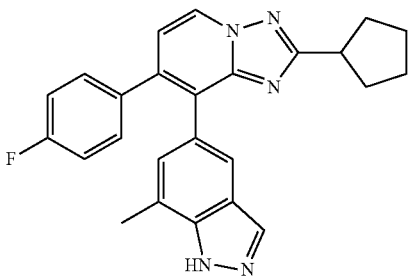 [SMILES: Cc1cc(-c2c(-c3ccc(F)cc3)ccn3nc(C4CCCC4)nc23)cc2cn[nH]c12]

The title compound was prepared in an analogous manner to Example 4 using 8-chloro-2-cyclopentyl-7-iodo-[1,2,4]triazolo[1,5-a]pyridine (Intermediate 31) at 90° C. for 6 h in Step A. MS (ESI): mass calcd. for $C_{25}H_{22}FN_5$, 411.2; m/z found, 412.2 [M+H]⁺. ¹H NMR (600 MHz, DMSO-d₆) δ 13.19 (s, 1H), 8.88 (d, J=7.0 Hz, 1H), 8.03 (s, 1H), 7.51 (d, J=0.7 Hz, 1H), 7.26-7.21 (m, 2H), 7.18 (d, J=7.0 Hz, 1H), 7.09 (t, J=8.9 Hz, 2H), 6.98 (t, J=1.1 Hz, 1H), 3.30-3.23 (m, 1H), 2.41 (s, 3H), 2.07-1.97 (m, 2H), 1.90-1.80 (m, 2H), 1.77-1.68 (m, 2H), 1.66-1.59 (m, 2H).

Example 10

8-(7-Methyl-1H-indazol-5-yl)-2-(trifluoromethyl)-[1,2,4]triazolo[1,5-a]pyridine-7-carbonitrile

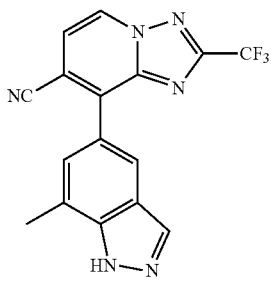 [SMILES: Cc1cc(-c2c(C#N)ccn3nc(C(F)(F)F)nc23)cc2cn[nH]c12]

Step A: 8-(7-Methyl-1-((2-(trimethylsilyl)ethoxy)methyl)-1H-indazol-5-yl)-2-(trifluoromethyl)-[1,2,4]triazolo[1,5-a]pyridine-7-carbonitrile. A microwave vial was charged with 7-chloro-8-(7-methyl-1-((2-(trimethylsilyl)ethoxy)methyl)-1H-indazol-5-yl)-2-(trifluoromethyl)-[1,2,4]triazolo[1,5-a]pyridine (Example 8, product from Step A; 30 mg, 62.2 µmol), $Zn(CN)_2$ (4.4 mg, 37.3 µmol), $Pd(PPh_3)_4$ (3.6 mg, 3.1 µmol), and DMF (0.14 mL). The vial was evacuated and refilled with $N_2$ (×3), then capped and sealed. The reaction was then stirred in a microwave reactor at 130° C. for 15 minutes. The mixture was diluted with EtOAc and the aqueous layer was extracted with EtOAc (×2). The combined organic extracts were washed with brine (×3), dried ($Na_2SO_4$) and filtered. The filtrate was concentrated in vacuo and the residue used directly in the next step without further purification. MS (ESI): mass calcd. for $C_{22}H_{23}F_3N_6OSi$, 472.2; m/z found, 473.1 $[M+H]^+$.

Step B: 8-(7-Methyl-1H-indazol-5-yl)-2-(trifluoromethyl)-[1,2,4]triazolo[1,5-a]pyridine-7-carbonitrile. The title compound was prepared in an analogous manner to Example 8, Step C using 8-(7-methyl-1-((2-(trimethylsilyl)ethoxy)methyl)-1H-indazol-5-yl)-2-(trifluoromethyl)-[1,2,4]triazolo[1,5-a]pyridine-7-carbonitrile to afford the title compound (12.1 mg, 57% yield). MS (ESI): mass calcd. for $C_{16}H_9F_3N_6$, 342.1; m/z found, 343.0 $[M+H]^+$. $^1$H NMR (600 MHz, DMSO-$d_6$) δ 13.48 (s, 1H), 9.29 (d, J=7.1 Hz, 1H), 8.28 (s, 1H), 8.05 (d, J=0.8 Hz, 1H), 7.90 (d, J=7.1 Hz, 1H), 7.51 (s, 1H), 2.62 (s, 3H).

Example 11

7-Methyl-5-[7-methyl-2-(trifluoromethyl)imidazo[1,2-a]pyridin-8-yl]indolin-2-one

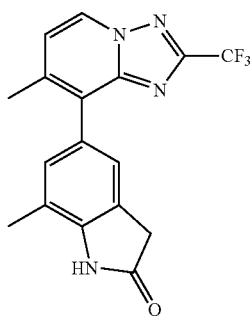 [SMILES: Cc1cc(-c2c(C)ccn3nc(C(F)(F)F)nc23)cc2c1NC(=O)C2]

A microwave vial was charged with 8-bromo-7-methyl-2-(trifluoromethyl)imidazo[1,2-a]pyridine (Intermediate 40, 40 mg, 0.14 mmol), 7-methyl-5-(4,4,5,5-tetramethyl-1,3,2-dioxaborolan-2-yl)indolin-2-one (Intermediate 5, 59 mg, 0.22 mmol), and chloro(2-dicyclohexylphosphino-2',4',6'-triisopropyl-1,1'-biphenyl)[2-(2'-amino-1,1'-biphenyl)]palladium(II) (17 mg, 0.022 mmol). The headspace was purged with Ar and the vessel capped. Dioxane (1.5 mL) and $K_3PO_4$ solution (0.5 mL, 0.5M) were then added and the vial heated at 160° C. for 70 minutes. After cooling to rt, the reaction was diluted with a mixture of EtOAc/$H_2O$. The layers were separated and the aqueous layer was extracted with EtOAc (×2). The combined organic extracts were washed with brine, dried ($MgSO_4$), filtered, and concentrated in vacuo. The residue was purified by reverse-phase preparative HPLC (XBridge $^{18}$C OBD column, 5-99% ACN in 20 mM $NH_4OH$) to provide the title compound as an off-white solid (36 mg, 73% yield). MS (ESI): mass calcd. for $C_{18}H_{14}F_3N_3O$, 345.1 $[M+H]^+$. $^1$H NMR (500 MHz, DMSO-$d_6$) δ 10.54 (s, 1H), 8.49-8.43 (m, 2H), 7.05 (s, 1H), 7.03-6.99 (m, 2H), 3.55 (s, 2H), 2.25 (s, 3H), 2.20 (s, 3H).

Example 12

5-(7-(4-Fluorophenyl)-2-(trifluoromethyl)imidazo[1,2-a]pyridin-8-yl)-1H-indazole

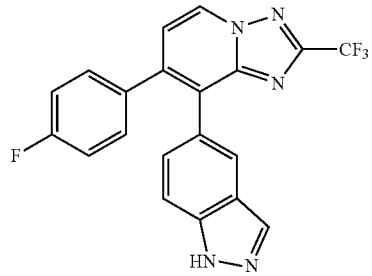 [SMILES: Fc1ccc(-c2ccn3nc(C(F)(F)F)nc3c2-c2ccc3[nH]ncc3c2)cc1]

Step A: 8-Chloro-7-(4-fluorophenyl)-2-(trifluoromethyl)imidazo[1,2-a]pyridine. A microwave vial was charged with 8-chloro-7-iodo-2-(trifluoromethyl)imidazo[1,2-a]pyridine (Intermediate 46, 42 mg, 0.121 mmol), 4-fluorophenylboronic acid (17.8 mg, 0.127 mmol), $Pd(PPh_3)_4$ (7.0 mg, 5 mol %), sat. aq. $Na_2CO_3$ (0.42 mL), and 1,4-dioxane (1.7 mL). The vial was evacuated and refilled with $N_2$ (×3), then capped and sealed. The mixture was then stirred in a microwave reactor at 110° C. for 1 h.

Step B: 5-(7-(4-Fluorophenyl)-2-(trifluoromethyl)imidazo[1,2-a]pyridin-8-yl)-1H-indazole. In the same vial as Step A, 5-(4,4,5-trimethyl-1,3,2-dioxaborolan-2-yl)-1H-indazole (44.4 mg, 0.182 mmol) and $Pd(dppf)Cl_2$—$CH_2Cl_2$ (8.9 mg, 9 mol %) were added at rt, and the head space purged with $N_2$. The vial was capped and stirred in a microwave reactor at 190° C. for 1 h. The mixture was then diluted with EtOAc, and washed with $H_2O$. The aqueous layer was extracted with EtOAc (×2), and the combined organics were washed with brine, dried ($Na_2SO_4$) and filtered. After concentrating the filtrate in vacuo, the residue was purified by preparative reverse-phase HPLC (XBridge $^{18}$C OBD column, 5-99% ACN in 20 mM $NH_4OH$) to afford the title compound as a tan solid (32 mg, 66% yield). MS (ESI): mass calcd. for $C_{21}H_2F_4N_4$, 396.1; m/z found, 397.0 $[M+H]^+$. $^1$H NMR (600 MHz, DMSO-$d_6$) δ 13.12 (s, 1H), 8.67 (d, J=7.1 Hz, 1H), 8.64 (d, J=0.9 Hz, 2H), 8.06 (s, 1H), 7.74 (dd, J=1.5, 0.8 Hz, 1H), 7.46 (d, J=8.6 Hz, 1H), 7.26-7.19 (m, 3H), 7.17 (dd, J=8.6, 1.5 Hz, 1H), 7.08 (t, J=8.9 Hz, 2H).

Example 13

8-(7-Chloro-1H-indazol-5-yl)-2,7-bis(trifluoromethyl)imidazo[1,2-c]pyrimidine

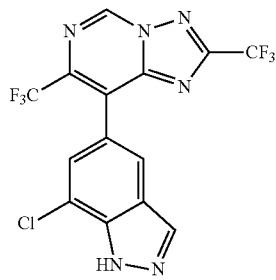 [SMILES: FC(F)(F)c1nc2c(-c3cc(Cl)c4[nH]ncc4c3)c(C(F)(F)F)ncn2n1]

To a solution of 8-bromo-2,7-bis(trifluoromethyl)imidazo [1,2-c]pyrimidine (Intermediate 48, 30 mg, 0.1 mmol), 7-chloro-5-(4,4,5,5-tetramethyl-1,3,2-dioxaborolan-2-yl)-1H-indazole (Intermediate 1, 30 mg, 0.11 mmol) in 4:1 dioxane:aqueous $Na_2CO_3$ was added Pd(dppf)$Cl_2$—$CH_2Cl_2$ (7.3 mg, 10 mol %); the mixture was degassed with nitrogen (×3), and then heated to 90° C. for 16 h. After cooling to rt, the reaction mixture was diluted with water and extracted with DCM (×2). The combined organic extracts were dried ($Na_2SO_4$) and concentrated. Purification (FCC, $SiO_2$; 0-50% EtOAc/hexanes) afforded the title compound as a white solid (9.0 mg, 24%). MS (ESI): mass calcd. for $C_{15}H_6ClF_6N_5$, 405.0; m/z found, 406.0 [M+H]$^+$. $^1$H NMR (600 MHz, DMSO-$d_6$) δ 13.89 (s, 1H), 9.64 (s, 1H), 8.89 (d, J=0.8 Hz, 1H), 8.34 (s, 1H), 7.87 (d, J=1.1 Hz, 1H), 7.57 (d, J=0.6 Hz, 1H).

Example 14

8-(7-Chloro-1H-indazol-5-yl)-2-(difluoromethyl)-7-(trifluoromethyl)imidazo[1,2-c]pyrimidine

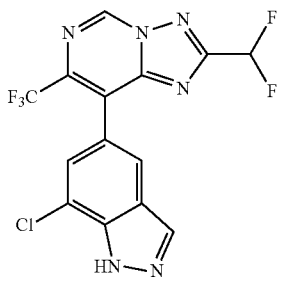 [SMILES: Cc1cc(-c2c(C(F)(F)F)ncn3nc(C(F)F)nc23)cc2cn[nH]c12]

Step A: 5-(7-Chloro-1H-indazol-5-yl)-6-(trifluoromethyl) pyrimidin-4-amine. To a solution of 5-bromo-6-(trifluoromethyl)pyrimidin-4-amine (Intermediate 12, 40 mg, 0.17 mmol), 7-chloro-5-(4,4,5,5-tetramethyl-1,3,2-dioxaborolan-2-yl)-1H-indazole (Intermediate 1, 55 mg, 0.20 mmol) in 4:1 dioxane:sat. aq. $Na_2CO_3$ (2.9 mL) was added Pd(dppf)$Cl_2$—$CH_2Cl_2$ (13.5 mg, 10 mol %). The mixture was degassed with nitrogen, and then heated in a microwave oven at 110° C. for 30 minutes. After cooling to rt, the reaction mixture was diluted with water and extracted with EtOAc (×2). The combined organic extracts were washed with brine, dried ($Na_2SO_4$), filtered, and concentrated. Purification (FCC, $SiO_2$; 0-100% EtOAc/hexanes) afforded the title compound as a white solid (20 mg, 38% yield). MS (ESI): mass calcd. for $C_{12}H_7ClF_3N_5$, 313.0; m/z found, 314.1 [M+H]$^+$.

Step B: 8-(7-Chloro-1H-indazol-5-yl)-2-(difluoromethyl)-7-(trifluoromethyl)imidazo[1,2-c]pyrimidine. To a solution of 5-(7-chloro-1H-indazol-5-yl)-6-(trifluoromethyl)pyrimidin-4-amine (150 mg, 0.62 mmol) in 1,4 dioxane (0.45 mL) were added 3A° molecular sieves (20 mg), followed by the addition of 3-bromo-1,1-difluoropropan-2-one (Intermediate 18, 128 mg, 0.74 mmol). The mixture was heated to 60° C. for 12 h. The reaction mixture was cooled to rt, diluted with EtOAc, and filtered through a pad of Celite®. The filtrate was concentrated in vacuo and the residue purified by preparative TLC ($SiO_2$; 60% EtOAc/ hexanes) to provide the title compound (7.2 mg, 29% yield). MS (ESI): mass calcd. for $C_{15}H_7ClF_5N_5$, 387.0; m/z found, 388.0 [M+H]$^+$. $^1$H NMR (600 MHz, DMSO-$d_6$) δ 13.85 (s, 1H), 9.63 (s, 1H), 8.60 (s, 1H), 8.32 (d, J=1.5 Hz, 1H), 7.87 (s, 1H), 7.57 (d, J=1.2 Hz, 1H), 7.21 (t, J=54.2 Hz, 1H).

Example 15

2-(Difluoromethyl)-8-(7-methyl-1H-indazol-5-yl)-7-(trifluoromethyl)imidazo[1,2-c]pyrimidine

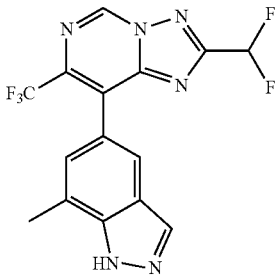

Step A: 5-(7-Methyl-1-((2-(trimethylsilyl)ethoxy) methyl)-1H-indazol-5-yl)-6-(trifluoromethyl)pyrimidin-4-amine. The title compound was prepared in a manner analogous to Example 14 using 5-bromo-6-(trifluoromethyl) pyrimidin-4-amine (Intermediate 12) and 7-methyl-5-(4,4, 5,5-tetramethyl-1,3,2-dioxaborolan-2-yl)-1-((2-(trimethylsilyl)ethoxy)methyl)-1H-indazole (Intermediate 3) in Step A. MS (ESI): mass calcd. for $C_{22}H_{24}F_5N_5OSi$, 497.5; m/z found, 498.2 [M+H]$^+$.

Step B: 2-(Difluoromethyl)-8-(7-methyl-1H-indazol-5-yl)-7-(trifluoromethyl)imidazo[1,2-c]pyrimidine. To a solution of 2-(difluoromethyl)-8-(7-methyl-1-((2-(trimethylsilyl)ethoxy)methyl)-1H-indazol-5-yl)-7-(trifluoromethyl) imidazo[1,2-c]pyrimidine from Step B (56 mg, 0.11 mmol) in DCM (1.8 mL) was added TFA (1.0 mL). The mixture was stirred at rt for 30 minutes. The solvent was concentrated in vacuo and then redissolved in EtOAc. The reaction mixture was diluted with $N_2HCO_3$, extracted with EtOAc (×2) and the combined organic extracts were dried ($Na_2SO_4$), filtered, and concentrated in vacuo. Purification (FCC, $SiO_2$; 0-10% MeOH/DCM) afforded the title compound as a white solid (25.8 mg, 62% yield). MS (ESI): mass calcd. for $C_{16}H_{10}F_5N_5$, 367.1; m/z found, 368.1 [M+H]$^+$. $^1$H NMR (500 MHz, DMSO-$d_6$) δ 13.37 (s, 1H), 9.60 (s, 1H), 8.57 (s, 1H), 8.16 (d, J=1.3 Hz, 1H), 7.66 (s, 1H), 7.33-7.06 (m, 2H), 2.58 (s, 3H).

Example 16

8-(7-Methyl-1H-indazol-5-yl)-2-(difluoromethyl)-7-(trifluoromethyl)-[1,2,4]triazolo[1,5-a]pyridine

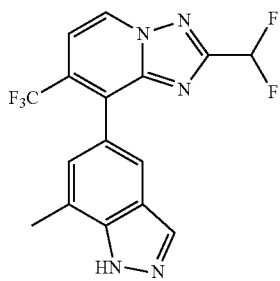 [SMILES: Cc1cc(-c2c(C(F)(F)F)ccn3nc(C(F)F)nc23)cc2cn[nH]c12]

The title compound was prepared in a manner analogous to Example 1 using 7-methyl-5-(4,4,5,5-tetramethyl-1,3,2-dioxaborolan-2-yl)-1H-indazole (Intermediate 2). MS (ESI): mass calcd. for $C_{16}H_{10}F_5N_5$, 367.1; m/z found, 368.1 [M+H]$^+$. $^1$H NMR (600 MHz, DMSO-$d_6$) δ 13.36 (s, 1H), 9.27 (d, J=7.3 Hz, 1H), 8.16 (d, J=1.3 Hz, 1H), 7.71 (d, J=7.3 Hz, 1H), 7.67 (s, 1H), 7.29 (t, J=52.7 Hz, 1H), 7.19 (s, 1H), 2.58 (s, 3H).

Example 17

7-Chloro-5-(2-(difluoromethyl)-7-(trifluoromethyl)-[1,2,4]triazolo[1,5-a]pyridin-8-yl)indolin-2-one

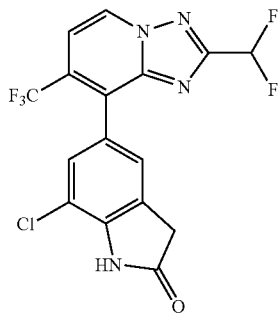 [SMILES: Cc1cc(-c2c(C(F)(F)F)ccn3nc(C(F)F)nc23)cc2c1NC(=O)C2]

The title compound was prepared in a manner analogous to Example 1 using 7-chloro-5-(4,4,5,5-tetramethyl-1,3,2-dioxaborolan-2-yl)indolin-2-one (Intermediate 7). MS (ESI): mass calcd. for $C_{16}H_8ClF_5N_4O$, 402.0; m/z found, 403.0 [M+H]$^+$. $^1$H NMR (600 MHz, DMSO-$d_6$) δ 11.00 (s, 1H), 9.27 (dd, J=7.3, 0.9 Hz, 1H), 7.70 (d, J=7.3 Hz, 1H), 7.43-7.22 (m, 3H), 3.71 (s, 2H).

Example 18

7-Methyl-5-(2-(difluoromethyl)-7-(trifluoromethyl)-[1,2,4]triazolo[1,5-a]pyridin-8-yl)indolin-2-one

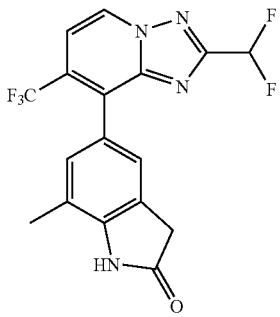

The title compound was prepared in a manner analogous to Example 1 using 7-methyl-5-(4,4,5,5-tetramethyl-1,3,2-dioxaborolan-2-yl)indolin-2-one (Intermediate 5). MS (ESI): mass calcd. for $C_{17}H_{11}F_5N_4O$, 382.1; m/z found, 383.1 [M+H]$^+$. $^1$H NMR (500 MHz, DMSO-$d_6$) δ 10.63 (s, 1H), 9.24 (d, J=7.3 Hz, 1H), 7.68 (d, J=7.3 Hz, 1H), 7.31 (t, $J_{(H-F)}$=52.8 Hz, 1H), 7.12 (s, 1H), 7.07 (s, 1H), 3.58 (s, 2H), 2.25 (s, 3H).

Example 19

8-(7-Chloro-1H-indazol-5-yl)-2,7-bis(trifluoromethyl)-[1,2,4]triazolo[1,5-a]pyridine

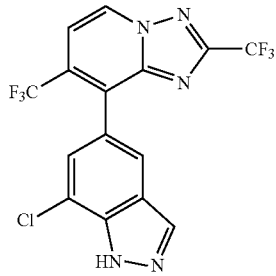 [SMILES: FC(F)(F)c1nc2c(-c3cc(Cl)c4[nH]ncc4c3)c(C(F)(F)F)ccn2n1]

The title compound was prepared in a manner analogous to Example 1 using 8-chloro-2,7-bis(trifluoromethyl)-[1,2,4]triazolo[1,5-a]pyridine (Intermediate 33). MS (ESI): mass calcd. for $C_{15}H_6ClF_6N_5$, 405.0; m/z found, 406.0 [M+H]$^+$. $^1$H NMR (600 MHz, DMSO-$d_6$) δ 13.87 (s, 1H), 9.38 (d, J=7.3 Hz, 1H), 8.34 (s, 1H), 7.89 (s, 1H), 7.83 (d, J=7.3 Hz, 1H), 7.59 (s, 1H).

Example 20

8-(7-Methyl-1H-indazol-5-yl)-2,7-bis(trifluoromethyl)-[1,2,4]triazolo[1,5-a]pyridine

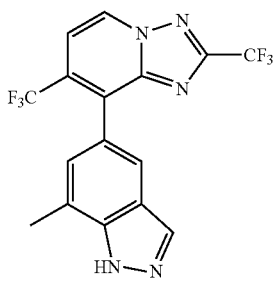 [SMILES: Cc1cc(-c2c(C(F)(F)F)ccn3nc(C(F)(F)F)nc23)cc2cn[nH]c12]

The title compound was prepared in a manner analogous to Example 1 using 8-chloro-2,7-bis(trifluoromethyl)-[1,2,4]triazolo[1,5-a]pyridine (Intermediate 33) and 7-methyl-5-(4,4,5,5-tetramethyl-1,3,2-dioxaborolan-2-yl)-1H-indazole (Intermediate 2) in a microwave reactor at 110° C. for 30 min. MS (ESI): mass calcd. for $C_{16}H_9F_6N_5$, 385.1; m/z found, 386.0 [M+H]$^+$. $^1$H NMR (500 MHz, DMSO-d$_6$) δ 13.40 (s, 1H), 9.34 (d, J=7.3 Hz, 1H), 8.18 (d, J=1.4 Hz, 1H), 7.81 (d, J=7.4 Hz, 1H), 7.68 (s, 1H), 7.20 (s, 1H), 2.58 (s, 3H).

Example 21

5-(2,7-Bis(trifluoromethyl)-[1,2,4]triazolo[1,5-a]pyridin-8-yl)-7-chloroindolin-2-one

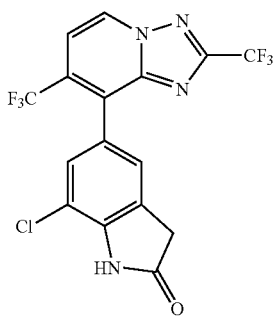

The title compound was prepared in a manner analogous to Example 1 using 8-chloro-2,7-bis(trifluoromethyl)-[1,2,4]triazolo[1,5-a]pyridine (Intermediate 33) and 7-chloro-5-(4,4,5,5-tetramethyl-1,3,2-dioxaborolan-2-yl)indolin-2-one (Intermediate 7) in a microwave reactor at 110° C. for 30 min. MS (ESI): mass calcd. for $C_{16}H_7ClF_6N_4O$, 420.0; m/z found, 421.0 [M+H]$^+$. $^1$H NMR (600 MHz, DMSO-d$_6$) δ 10.99 (s, 1H), 9.33 (d, J=7.3 Hz, 1H), 7.78 (d, J=7.3 Hz, 1H), 7.37 (s, 1H), 7.28 (s, 1H), 3.71 (s, 2H).

Example 22

5-(2,7-Bis(trifluoromethyl)-[1,2,4]triazolo[1,5-a]pyridin-8-yl)-7-methylindolin-2-one

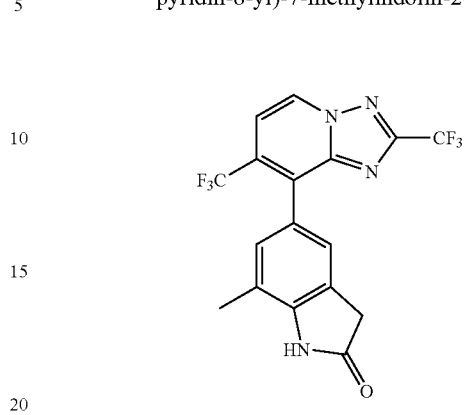

The title compound was prepared in a manner analogous to Example 1 using 8-chloro-2,7-bis(trifluoromethyl)-[1,2,4]triazolo[1,5-a]pyridine (Intermediate 33) and 7-methyl-5-(4,4,5,5-tetramethyl-1,3,2-dioxaborolan-2-yl)indolin-2-one (Intermediate 5) in a microwave reactor at 110° C. for 30 min. MS (ESI): mass calcd. for $C_{17}H_{10}F_6N_4O$, 400.1; m/z found, 401.0 [M+H]$^+$. $^1$H NMR (600 MHz, DMSO-d$_6$) δ 10.66 (s, 1H), 9.31 (d, J=7.3 Hz, 1H), 7.78 (d, J=7.3 Hz, 1H), 7.13 (s, 1H), 7.07 (s, 1H), 3.59 (s, 2H), 2.25 (s, 3H).

Example 23

8-(7-Chloro-1H-indazol-5-yl)-7-(difluoromethyl)-2-(trifluoromethyl)-[1,2,4]triazolo[1,5-a]pyridine

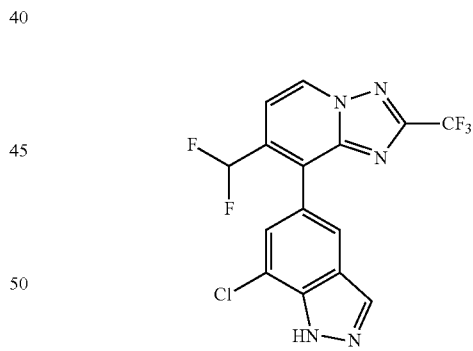

The title compound was prepared in a manner analogous to Example 1 using 8-chloro-7-(difluoromethyl)-2-(trifluoromethyl)-[1,2,4]triazolo[1,5-a]pyridine (Intermediate 38) with microwave heating at 110° C. for 30 min. MS (ESI): mass calcd. for $C_{15}H_7ClF_5N_5$, 387.0; m/z found, 388.0 [M+H]$^+$. $^1$H NMR (500 MHz, DMSO-d$_6$) δ 13.89 (s, 1H), 9.29 (d, J=7.2 Hz, 1H), 8.37 (s, 1H), 7.89 (d, J=1.2 Hz, 1H), 7.72 (d, J=7.3 Hz, 1H), 7.63 (d, J=1.1 Hz, 1H), 6.97 (t, J=53.4 Hz, 1H).

Example 24

8-(7-Methyl-1H-indazol-5-yl)-7-(difluoromethyl)-2-(trifluoromethyl)-[1,2,4]triazolo[1,5-a]pyridine

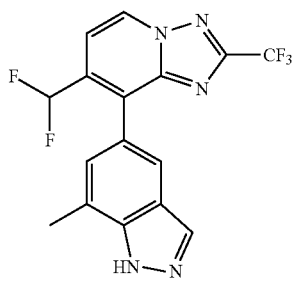

The title compound was prepared in a manner analogous to Example 1 using 8-chloro-7-(difluoromethyl)-2-(trifluoromethyl)-[1,2,4]triazolo[1,5-a]pyridine (Intermediate 38) and 7-Methyl-5-(4,4,5,5-tetramethyl-1,3,2-dioxaborolan-2-yl)-1H-indazole (Intermediate 2) with microwave heating at 110° C. for 30 min. MS (ESI): mass calcd. for $C_{16}H_{10}F_5N_5$, 367.1; m/z found, 368.1[M+H]$^+$. $^1$H NMR (500 MHz, DMSO-d$_6$) δ 13.43 (s, 1H), 9.25 (d, J=7.2 Hz, 1H), 8.22 (s, 1H), 7.75-7.67 (m, 2H), 7.26 (s, 1H), 6.89 (t, J=53.7 Hz, 1H), 2.60 (s, 3H).

Example 25

7-Chloro-5-(7-(difluoromethyl)-2-(trifluoromethyl)-[1,2,4]triazolo[1,5-a]pyridin-8-yl)indolin-2-one

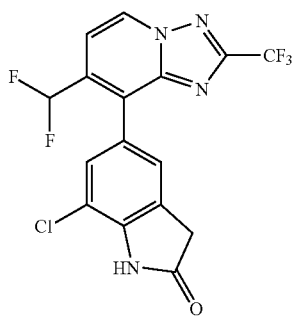 [SMILES: O=C1Cc2cc(-c3c(C(F)F)ccn4nc(C(F)(F)F)nc34)cc(Cl)c2N1]

The title compound was prepared in a manner analogous to Example 1 using 8-chloro-7-(difluoromethyl)-2-(trifluoromethyl)-[1,2,4]triazolo[1,5-a]pyridine (Intermediate 38) and 7-chloro-5-(4,4,5,5-tetramethyl-1,3,2-dioxaborolan-2-yl)indolin-2-one (Intermediate 7) in a microwave reactor at 110° C. for 30 min. MS (ESI): mass calcd. for $C_{16}H_8ClF_5N_4O$, 402.0; m/z found, 403.0 [M+H]$^+$. $^1$H NMR (500 MHz, DMSO-d$_6$) δ 11.07 (s, 1H), 9.25 (d, J=7.2 Hz, 1H), 7.68 (d, J=7.2 Hz, 1H), 7.42 (d, J=1.5 Hz, 1H), 7.32 (d, J=1.2 Hz, 1H), 6.96 (t, J$_{(H-F)}$=53.5 Hz, 1H), 3.73 (s, 2H).

Example 26

7-Methyl-5-(7-(difluoromethyl)-2-(trifluoromethyl)-[1,2,4]triazolo[1,5-a]pyridin-8-yl)indolin-2-one

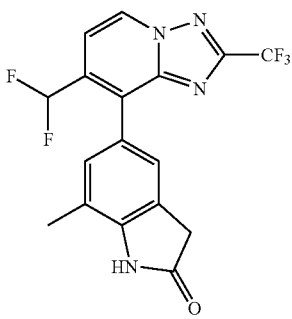 [SMILES: Cc1cc(-c2c(C(F)F)ccn3nc(C(F)(F)F)nc23)cc2c1NC(=O)C2]

The title compound was prepared in a manner analogous to Example 1 using 8-chloro-7-(difluoromethyl)-2-(trifluoromethyl)-[1,2,4]triazolo[1,5-a]pyridine (Intermediate 38) and 7-methyl-5-(4,4,5,5-tetramethyl-1,3,2-dioxaborolan-2-yl)indolin-2-one (Intermediate 5) in a microwave reactor at 110° C. for 30 min. MS (ESI): mass calcd. for $C_{17}H_{11}F_5N_4O$, 382.1; m/z found, 383.1 [M+H]$^+$. $^1$H NMR (500 MHz, DMSO-d$_6$) δ 10.69 (s, 1H), 9.21 (d, J=7.2 Hz, 1H), 7.67 (d, J=7.2 Hz, 1H), 7.19 (s, 1H), 7.13 (s, 1H), 6.89 (t, J$_{(H-F)}$=53.7 Hz, 1H), 3.61 (s, 2H), 2.28 (s, 3H).

Example 27

7-Methyl-8-(7-methyl-1H-indazol-5-yl)-2-(trifluoromethyl)-[1,2,4]triazolo[1,5-a]pyridine

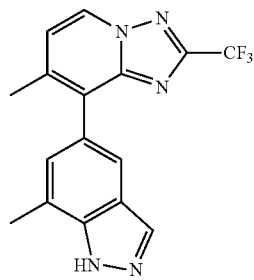 [SMILES: Cc1ccn2nc(C(F)(F)F)nc2c1-c1cc(C)c2[nH]ncc2c1]

The title compound was prepared in a manner analogous to Example 1 using 8-bromo-7-methyl-2-(trifluoromethyl)-[1,2,4]triazolo[1,5-a]pyridine (Intermediate 21) and 7-methyl-5-(4,4,5,5-tetramethyl-1,3,2-dioxaborolan-2-yl)-1H-indazole (Intermediate 2), and XPhos Pd G2 precatalyst in a microwave reactor at 160° C. for 1 h. MS (ESI): mass calcd. for $C_{16}H_{12}F_3N_5$, 331.1; m/z found, 332.1 [M+H]$^+$. $^1$H NMR (600 MHz, DMSO-d$_6$) δ 13.32 (s, 1H), 9.00 (d, J=7.0 Hz, 1H), 8.16 (s, 1H), 7.67 (s, 1H), 7.44 (d, J=7.0 Hz, 1H), 7.19 (t, J=1.2 Hz, 1H), 2.58 (s, 3H), 2.35 (s, 3H).

Example 28

7-Ethyl-8-(7-methyl-1H-indazol-5-yl)-2-(trifluoromethyl)-[1,2,4]triazolo[1,5-a]pyridine

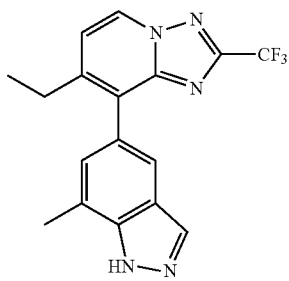 [SMILES: CCc1ccn2nc(C(F)(F)F)nc2c1-c1cc(C)c2[nH]ncc2c1]

The title compound was prepared in a manner analogous to Example 1 using 8-chloro-7-ethyl-2-(trifluoromethyl)-[1,2,4]triazolo[1,5-a]pyridine (Intermediate 39) and 7-methyl-5-(4,4,5,5-tetramethyl-1,3,2-dioxaborolan-2-yl)-1H-indazole (Intermediate 2), and XPhos Pd G2 precatalyst in a microwave reactor at 150° C. for 1 h. MS (ESI): mass calcd. for $C_{17}H_{14}F_3N_5$, 345.1; m/z found, 346.2 [M+H]$^+$. $^1$H NMR (600 MHz, DMSO-d$_6$) δ 13.34 (s, 1H), 9.04 (d, J=7.1 Hz, 1H), 8.15 (s, 1H), 7.63 (s, 1H), 7.48 (d, J=7.1 Hz, 1H), 7.14 (s, 1H), 2.63 (q, J=7.6 Hz, 2H), 2.58 (s, 3H), 1.13 (t, J=7.5 Hz, 3H).

Example 29

7-Methoxy-8-(7-methyl-1H-indazol-5-yl)-2-(trifluoromethyl)-[1,2,4]triazolo[1,5-a]pyridine

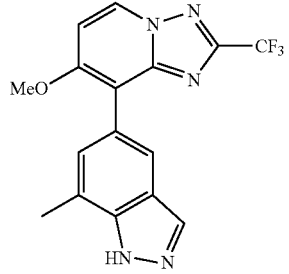 [SMILES: COc1ccn2nc(C(F)(F)F)nc2c1-c1cc(C)c2[nH]ncc2c1]

The title compound was prepared in a manner analogous to Example 1, using 8-iodo-7-methoxy-2-(trifluoromethyl)-[1,2,4]triazolo[1,5-a]pyridine (Intermediate 22) and 7-methyl-5-(4,4,5,5-tetramethyl-1,3,2-dioxaborolan-2-yl)-1H-indazole (Intermediate 2), and XPhos Pd G2 precatalyst in a microwave reactor at 110° C. for 30 min. MS (ESI): mass calcd. for $C_{16}H_{12}F_3N_5O$, 347.1; m/z found, 348.1 [M+H]$^+$. $^1$H NMR (600 MHz, DMSO-d$_6$) δ 13.26 (s, 1H), 9.12 (d, J=7.7 Hz, 1H), 8.14 (d, J=1.5 Hz, 1H), 7.78 (s, 1H), 7.53 (d, J=7.8 Hz, 1H), 7.29 (t, J=1.1 Hz, 1H), 3.95 (s, 3H), 2.56 (s, 3H).

Example 30

8-(7-Chloro-1H-indazol-5-yl)-2-cyclopropyl-7-(trifluoromethyl)-[1,2,4]triazolo[1,5-a]pyridine

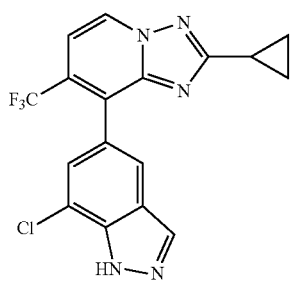 [SMILES: FC(F)(F)c1ccn2nc(C3CC3)nc2c1-c1cc(Cl)c2[nH]ncc2c1]

The title compound was prepared in a manner analogous to Example 1 using 8-chloro-2-cyclopropyl-7-(trifluoromethyl)-[1,2,4]triazolo[1,5-a]pyridine (Intermediate 35). MS (ESI): mass calcd. for $C_{17}H_{11}ClF_3N_5$, 377.1; m/z found, 378.1 [M+H]$^+$. $^1$H NMR (500 MHz, DMSO-d$_6$) δ 13.85 (s, 1H), 9.06 (d, J=7.2 Hz, 1H), 8.30 (s, 1H), 7.92-7.75 (m, 1H), 7.58-7.43 (m, 2H), 2.14 (tt, J=8.2, 4.8 Hz, 1H), 1.02 (ddd, J=8.3, 6.6, 3.9 Hz, 2H), 0.91-0.86 (m, 2H).

Example 31

2-Cyclopropyl-8-(7-methyl-1H-indazol-5-yl)-7-(trifluoromethyl)-[1,2,4]triazolo[1,5-a]pyridine

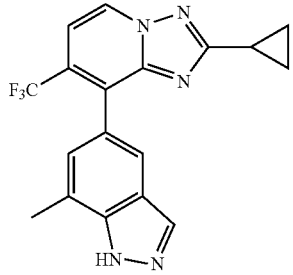 [SMILES: Cc1cc(-c2c(C(F)(F)F)ccn3nc(C4CC4)nc23)cc2cn[nH]c12]

The title compound was prepared in a manner analogous to Example 1 using 8-chloro-2-cyclopropyl-7-(trifluoromethyl)-[1,2,4]triazolo[1,5-a]pyridine (Intermediate 35) and 7-methyl-5-(4,4,5,5-tetramethyl-1,3,2-dioxaborolan-2-yl)-1H-indazole (Intermediate 2) and XPhos Pd G2 precatalyst in a microwave reactor at 110° C. for 30 min. MS (ESI): mass calcd. for $C_{18}H_{14}F_3N_5$, 357.1; m/z found, 358.2 [M+H]$^+$. $^1$H NMR (600 MHz, DMSO-d$_6$) δ 13.35 (s, 1H), 9.03 (d, J=7.2 Hz, 1H), 8.15 (s, 1H), 7.61 (s, 1H), 7.46 (d, J=7.2 Hz, 1H), 7.14 (s, 1H), 2.56 (s, 3H), 2.18-2.08 (m, 1H), 1.04-0.99 (m, 2H), 0.90-0.86 (m, 2H).

Example 32

8-(7-Chloro-1H-indazol-5-yl)-2-methyl-7-(trifluoromethyl)-[1,2,4]triazolo[1,5-a]pyridine

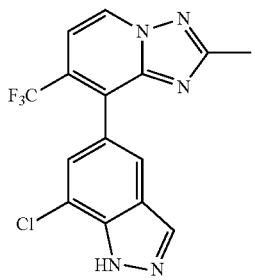 [SMILES: Cc1nc2c(-c3cc(Cl)c4[nH]ncc4c3)c(C(F)(F)F)ccn2n1]

The title compound was prepared in a manner analogous to Example 1 using 8-chloro-2-methyl-7-(trifluoromethyl)-[1,2,4]triazolo[1,5-a]pyridine (Intermediate 34). MS (ESI): mass calcd. for $C_{15}H_9ClF_3N_5$, 351.0; m/z found, 352.0 [M+H]$^+$. $^1$H NMR (500 MHz, DMSO-$d_6$) δ 13.85 (s, 1H), 9.11 (dd, J=7.1, 0.9 Hz, 1H), 8.32 (s, 1H), 7.84 (d, J=1.3 Hz, 1H), 7.62-7.45 (m, 2H), 2.46 (s, 3H).

Example 33

2-Methyl-8-(7-methyl-1H-indazol-5-yl)-7-(trifluoromethyl)-[1,2,4]triazolo[1,5-a]pyridine

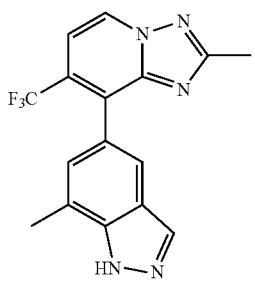 [SMILES: Cc1nc2c(-c3cc(C)c4[nH]ncc4c3)c(C(F)(F)F)ccn2n1]

The title compound was prepared in a manner analogous to Example 1 using 8-chloro-2-methyl-7-(trifluoromethyl)-[1,2,4]triazolo[1,5-a]pyridine (Intermediate 34) and 7-methyl-5-(4,4,5,5-tetramethyl-1,3,2-dioxaborolan-2-yl)-1H-indazole (Intermediate 2). MS (ESI): mass calcd. for $C_{16}H_{12}F_3N_5$, 331.1; m/z found, 332.1 [M+H]$^+$. $^1$H NMR (500 MHz, DMSO-$d_6$) δ 13.34 (s, 1H), 9.07 (dd, J=7.2, 0.8 Hz, 1H), 8.23-8.07 (m, 1H), 7.62 (d, J=1.4 Hz, 1H), 7.49 (d, J=7.2 Hz, 1H), 7.15 (s, 1H), 2.57 (t, J=0.8 Hz, 3H), 2.44 (s, 3H).

Example 34

8-(7-Chloro-1H-indazol-5-yl)-2-ethyl-7-(trifluoromethyl)-[1,2,4]triazolo[1,5-a]pyridine

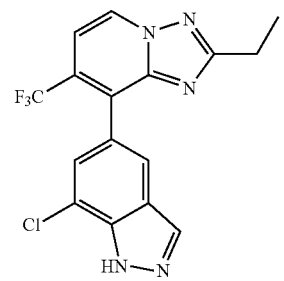 [SMILES: CCc1nc2c(-c3cc(Cl)c4[nH]ncc4c3)c(C(F)(F)F)ccn2n1]

The title compound was prepared in a manner analogous to Example 1 using 8-chloro-2-ethyl-7-(trifluoromethyl)-[1,2,4]triazolo[1,5-a]pyridine (Intermediate 36). MS (ESI): mass calcd. for $C_{16}H_{11}ClF_3N_5$, 365.1; m/z found, 366.0 [M+H]$^+$. $^1$H NMR (500 MHz, DMSO-$d_6$) δ 13.84 (s, 1H), 9.13 (d, J=7.1 Hz, 1H), 8.31 (s, 1H), 7.92-7.77 (m, 1H), 7.60-7.45 (m, 2H), 2.82 (q, J=7.6 Hz, 2H), 1.26 (t, J=7.6 Hz, 3H).

Example 35

2-Ethyl-8-(7-methyl-1H-indazol-5-yl)-7-(trifluoromethyl)-[1,2,4]triazolo[1,5-a]pyridine

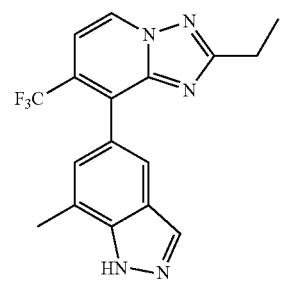 [SMILES: CCc1nc2c(-c3cc(C)c4[nH]ncc4c3)c(C(F)(F)F)ccn2n1]

The title compound was prepared in a manner analogous to Example 1 using 8-chloro-2-ethyl-7-(trifluoromethyl)-[1,2,4]triazolo[1,5-a]pyridine (Intermediate 36) and 7-methyl-5-(4,4,5,5-tetramethyl-1,3,2-dioxaborolan-2-yl)-1H-indazole (Intermediate 2). MS (ESI): mass calcd. for $C_{17}H_{14}F_3N_5$, 345.1; m/z found, 346.0 [M+H]$^+$. $^1$H NMR (500 MHz, DMSO-$d_6$) δ 13.35 (s, 1H), 9.09 (d, J=7.2 Hz, 1H), 8.15 (s, 1H), 7.63 (s, 1H), 7.49 (d, J=7.2 Hz, 1H), 7.16 (s, 1H), 2.81 (q, J=7.6 Hz, 2H), 2.57 (s, 3H), 1.25 (t, J=7.6 Hz, 3H).

Example 36

5-[2-Ethyl-7-(trifluoromethyl)-[1,2,4]triazolo[1,5-a]pyridin-8-yl]-7-methyl-indolin-2-one

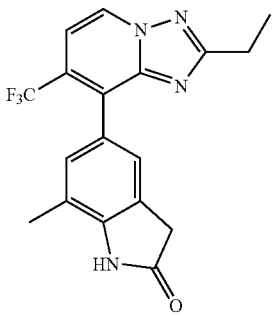 [SMILES: CCc1nc2c(-c3cc(C)c4c(c3)CC(=O)N4)c(C(F)(F)F)ccn2n1]

The title compound was prepared in a manner analogous to Example 1 using 8-chloro-2-ethyl-7-(trifluoromethyl)-[1,2,4]triazolo[1,5-a]pyridine (Intermediate 36) and 7-methyl-5-(4,4,5,5-tetramethyl-1,3,2-dioxaborolan-2-yl)indolin-2-one (Intermediate 5). MS (ESI): mass calcd. for $C_{18}H_{15}F_3N_4O$, 360.1; m/z found, 361.2 [M+H]$^+$. $^1$H NMR (500 MHz, DMSO-d$_6$) δ 10.61 (s, 1H), 9.12-8.90 (m, 1H), 7.46 (d, J=7.2 Hz, 1H), 7.06 (dd, J=25.4, 1.6 Hz, 2H), 3.57 (s, 2H), 2.82 (q, J=7.6 Hz, 2H), 2.25 (s, 3H), 1.27 (t, J=7.6 Hz, 3H).

Example 37

8-(7-Chloro-1H-indazol-5-yl)-2-isopropyl-7-(trifluoromethyl)-[1,2,4]triazolo[1,5-a]pyridine

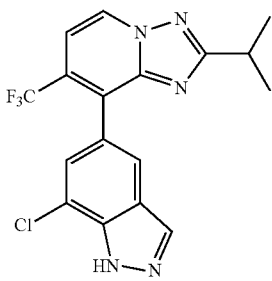 [SMILES: CC(C)c1nc2c(-c3cc(Cl)c4[nH]ncc4c3)c(C(F)(F)F)ccn2n1]

The title compound was prepared in a manner analogous to Example 1 using 8-chloro-2-isopropyl-7-(trifluoromethyl)-[1,2,4]triazolo[1,5-a]pyridine (Intermediate 37). MS (ESI): mass calcd. for $C_{17}H_{13}ClF_3N_5$, 379.1; m/z found, 380.1 [M+H]$^+$. $^1$H NMR (500 MHz, DMSO-d$_6$) δ 13.84 (s, 1H), 9.14 (dd, J=7.2, 0.8 Hz, 1H), 8.31 (s, 1H), 7.84 (d, J=1.3 Hz, 1H), 7.62-7.47 (m, 2H), 3.19-3.08 (m, 1H), 1.29 (d, J=7.0 Hz, 6H).

Example 38

2-Isopropyl-8-(7-methyl-1H-indazol-5-yl)-7-(trifluoromethyl)-[1,2,4]triazolo[1,5-a]pyridine

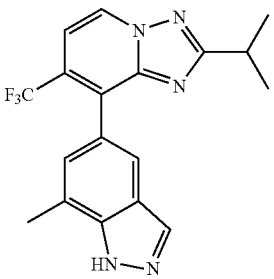 [SMILES: Cc1cc(-c2c(C(F)(F)F)ccn3nc(C(C)C)nc23)cc2cn[nH]c12]

The title compound was prepared in a manner analogous to Example 1 using 8-chloro-2-isopropyl-7-(trifluoromethyl)-[1,2,4]triazolo[1,5-a]pyridine (Intermediate 37) and 7-methyl-5-(4,4,5,5-tetramethyl-1,3,2-dioxaborolan-2-yl)-1H-indazole (Intermediate 2). MS (ESI): mass calcd. for $C_{18}H_{16}F_3N_5$, 359.1; m/z found, 360.1 [M+H]$^+$. $^1$H NMR (500 MHz, DMSO-d$_6$) δ 13.35 (s, 1H), 9.09 (dd, J=7.2, 0.7 Hz, 1H), 8.15 (s, 1H), 7.63 (d, J=1.4 Hz, 1H), 7.48 (d, J=7.2 Hz, 1H), 7.16 (s, 1H), 3.12 (dt, J=13.9, 7.0 Hz, 1H), 2.57 (t, J=0.8 Hz, 3H), 1.28 (d, J=7.0 Hz, 6H).

Example 39

5-[2-Isopropyl-7-(trifluoromethyl)-[1,2,4]triazolo[1,5-a]pyridin-8-yl]-7-methyl-indolin-2-one

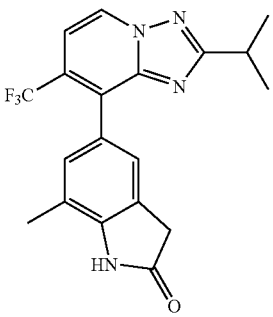 [SMILES: Cc1cc(-c2c(C(F)(F)F)ccn3nc(C(C)C)nc23)cc2c1NC(=O)C2]

The title compound was prepared in a manner analogous to Example 1 using 8-chloro-2-isopropyl-7-(trifluoromethyl)-[1,2,4]triazolo[1,5-a]pyridine (Intermediate 37) and 7-methyl-5-(4,4,5,5-tetramethyl-1,3,2-dioxaborolan-2-yl)indolin-2-one (Intermediate 5). MS (ESI): mass calcd. for $C_{19}H_{17}F_3N_4O$, 374.1; m/z found, 375.1 [M+H]$^+$. $^1$H NMR (500 MHz, DMSO-d$_6$) δ 10.61 (s, 1H), 9.06 (d, J=7.2 Hz, 1H), 7.45 (d, J=7.2 Hz, 1H), 7.12-6.97 (m, 2H), 3.57 (s, 2H), 3.19-3.10 (m, 1H), 2.25 (s, 3H), 1.30 (d, J=6.9 Hz, 6H).

Example 40

2-Isopropyl-7-methyl-8-(7-methyl-1H-indazol-5-yl)-[1,2,4]triazolo[1,5-a]pyridine

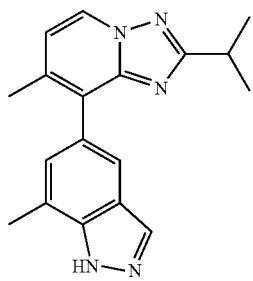 [SMILES: Cc1ccn2nc(C(C)C)nc2c1-c1cc(C)c2[nH]ncc2c1]

The title compound was prepared in a manner analogous to Example 1 using 8-bromo-2-isopropyl-7-methyl-[1,2,4]triazolo[1,5-a]pyridine (Intermediate 32) and 7-methyl-5-(4,4,5,5-tetramethyl-1,3,2-dioxaborolan-2-yl)-1H-indazole (Intermediate 2), and XPhos Pd G2 precatalyst in a microwave reactor at 160° C. for 1 h. MS (ESI): mass calcd. for $C_{18}H_{19}N_5$, 305.2; m/z found, 306.1 [M+H]$^+$. $^1$H NMR (500 MHz, CDCl$_3$) δ 13.12 (s, 1H), 8.44 (d, J=6.9 Hz, 1H), 7.78 (s, 1H), 7.31 (s, 1H), 6.93 (d, J=6.9 Hz, 1H), 6.77 (s, 1H), 3.44-3.28 (m, 1H), 2.23 (s, 3H), 2.21 (s, 3H), 1.50 (d, J=6.9 Hz, 6H).

Example 41

7-Chloro-8-(7-chloro-1H-indazol-5-yl)-2-(trifluoromethyl)-[1,2,4]triazolo[1,5-a]pyridine

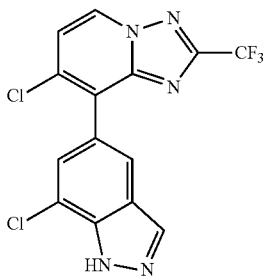 [SMILES: FC(F)(F)c1nc2c(-c3cc(Cl)c4[nH]ncc4c3)c(Cl)ccn2n1]

The title compound was prepared in a manner analogous to Example 1 using 7-chloro-8-iodo-2-(trifluoromethyl)-[1,2,4]triazolo[1,5-a]pyridine (Intermediate 20). MS (ESI): mass calcd. for $C_{14}H_6Cl_2F_3N_5$, 371.0; m/z found, 374.0 [M+H]$^+$. $^1$H NMR (400 MHz, DMSO-d$_6$) δ 13.86 (s, 1H), 9.18 (d, J=7.3 Hz, 1H), 8.35 (s, 1H), 8.00 (d, J=1.3 Hz, 1H), 7.71 (d, J=7.3 Hz, 1H), 7.65 (d, J=1.4 Hz, 1H).

Example 42

7-(4-Fluorophenyl)-8-(7-fluoro-1H-indazol-5-yl)-2-(trifluoromethyl)-[1,2,4]triazolo[1,5-a]pyridine

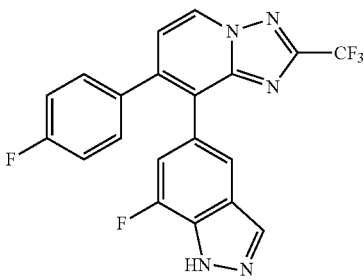 [SMILES: Fc1ccc(-c2ccn3nc(C(F)(F)F)nc3c2-c2cc(F)c3[nH]ncc3c2)cc1]

The title compound was prepared in a manner analogous to Example 4 using 8-chloro-7-iodo-2-(trifluoromethyl)-[1,2,4]triazolo[1,5-a]pyridine (Intermediate 19) in Step A, and 7-fluoro-5-(4,4,5,5-tetramethyl-1,3,2-dioxaborolan-2-yl)-1H-indazole in Step B. MS (ESI): mass calcd. for $C_{20}H_{10}F_5N_5$, 415.1; m/z found, 416.1 [M+H]$^+$. $^1$H NMR (400 MHz, MeOD) δ 8.91 (d, J=7.1 Hz, 1H), 8.09 (d, J=3.3 Hz, 1H), 7.62 (d, J=1.2 Hz, 1H), 7.46 (d, J=7.1 Hz, 1H), 7.32-7.27 (m, 2H), 7.07-7.00 (m, 3H).

Example 43

7-(4-Fluorophenyl)-8-(7-chloro-1H-indazol-5-yl)-2-(trifluoromethyl)-[1,2,4]triazolo[1,5-a]pyridine

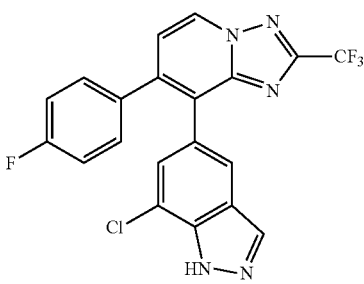

The title compound was prepared in an analogous manner to Example 4 using 8-chloro-7-iodo-2-(trifluoromethyl)-[1,2,4]triazolo[1,5-a]pyridine (Intermediate 19) at 90° C. for 6 h in Step A, and 7-chloro-5-(4,4,5,5-tetramethyl-1,3,2-dioxaborolan-2-yl)-1H-indazole (Intermediate 1) with Pd(dppf)Cl$_2$—CH$_2$Cl$_2$ in a microwave reactor at 130° C. for 30 min in Step B. MS (ESI): mass calcd. for $C_{20}H_{10}ClF_4N_5$, 431.1; m/z found, 432.0 [M+H]$^+$. $^1$H NMR (600 MHz, DMSO-d$_6$) δ 13.72 (s, 1H), 9.19 (d, J=7.1 Hz, 1H), 8.22 (s, 1H), 7.75 (d, J=1.3 Hz, 1H), 7.54 (d, J=7.1 Hz, 1H), 7.34-7.29 (m, 3H), 7.16 (t, J=8.9 Hz, 2H).

Example 44

7-(4-Fluorophenyl)-8-(7-methyl-1H-indazol-5-yl)-2-(trifluoromethyl)-[1,2,4]triazolo[1,5-a]pyridine

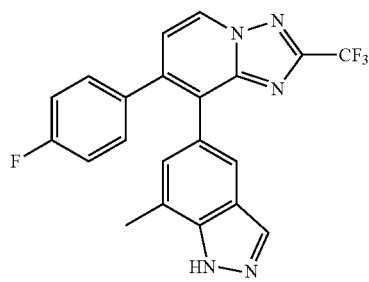 [SMILES: Cc1cc(-c2c(-c3ccc(F)cc3)ccn3nc(C(F)(F)F)nc23)cc2cn[nH]c12]

The title compound was prepared in an analogous manner to Example 4 using 8-chloro-7-iodo-2-(trifluoromethyl)-[1,2,4]triazolo[1,5-a]pyridine (Intermediate 19) in Step A, and Pd(dppf)Cl$_2$—CH$_2$Cl$_2$ in a microwave reactor at 190° C. for 1 h in Step B. MS (ESI): mass calcd. for C$_{11}$H$_{13}$F$_4$N$_5$, 411.1; m/z found, 412.0 [M+H]$^+$. $^1$H NMR (500 MHz, MeOD) δ 8.88 (d, J=7.1 Hz, 1H), 8.00 (s, 1H), 7.61 (s, 1H), 7.45 (d, J=7.1 Hz, 1H), 7.30-7.24 (m, 2H), 7.06 (s, 1H), 6.99 (t, J=8.8 Hz, 2H), 2.47 (s, 3H).

Example 45

8-(3-Fluoro-1H-indazol-5-yl)-7-(4-fluorophenyl)-2-(trifluoromethyl)-[1,2,4]triazolo[1,5-a]pyridine

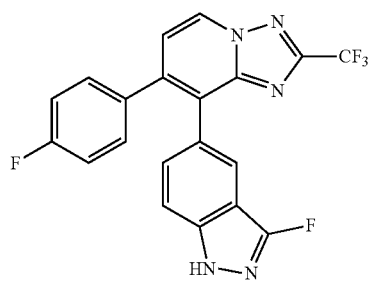 [SMILES: Fc1ccc(-c2ccn3nc(C(F)(F)F)nc3c2-c2ccc3[nH]nc(F)c3c2)cc1]

The title compound was prepared in an analogous manner to Example 4 using 8-chloro-7-iodo-2-(trifluoromethyl)-[1,2,4]triazolo[1,5-a]pyridine (Intermediate 19) in a microwave reactor at 100° C. for 1 h in Step A, and 3-fluoro-5-(4,4,5,5-tetramethyl-1,3,2-dioxaborolan-2-yl)-1H-indazole (Intermediate 4) in Step B. MS (ESI): mass calcd. for C$_{20}$H$_{10}$F$_5$N$_5$, 415.1; m/z found, 416.1 [M+H]$^+$. $^1$H NMR (600 MHz, DMSO-d$_6$) δ 12.66 (s, 1H), 9.18 (d, J=7.1 Hz, 1H), 7.73 (s, 1H), 7.54 (d, J=7.1 Hz, 1H), 7.44 (dd, J=8.8, 1.5 Hz, 1H), 7.32-7.28 (m, 2H), 7.26 (dd, J=8.8, 1.6 Hz, 1H), 7.15 (t, J=8.9 Hz, 2H).

Example 46

2-(Difluoromethyl)-7-(4-fluorophenyl)-8-(7-methyl-1H-indazol-5-yl)-[1,2,4]triazolo[1,5-a]pyridine

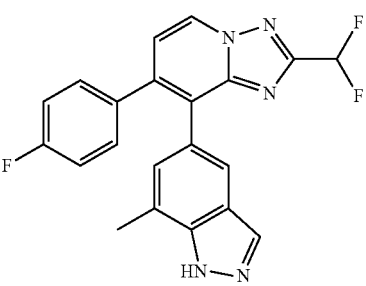 [SMILES: Cc1cc(-c2c(-c3ccc(F)cc3)ccn3nc(C(F)F)nc23)cc2cn[nH]c12]

The title compound was prepared in an analogous manner to Example 4 using 8-chloro-2-(difluoromethyl)-7-iodo-[1,2,4]triazolo[1,5-a]pyridine (Intermediate 23) at 90° C. for 6 h in Step A. MS (ESI): mass calcd. for C$_{21}$H$_{14}$F$_3$N$_5$, 393.1; m/z found, [M+H]$^+$. $^1$H NMR (600 MHz, DMSO-d$_6$) δ 13.23 (s, 1H), 9.10 (d, J=7.1 Hz, 1H), 8.05 (s, 1H), 7.55 (d, J=0.7 Hz, 1H), 7.44 (d, J=7.1 Hz, 1H), 7.38-7.18 (m, 3H), 7.13 (t, J=8.9 Hz, 2H), 7.00 (s, 1H), 2.43 (s, 3H).

Example 47

7-(4-Fluorophenyl)-2-(methoxymethyl)-8-(7-methyl-1H-indazol-5-yl)-[1,2,4]triazolo[1,5-a]pyridine

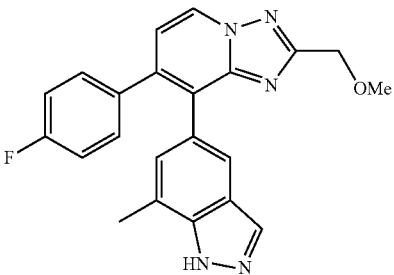 [SMILES: COCc1nc2c(-c3cc(C)c4[nH]ncc4c3)c(-c3ccc(F)cc3)ccn2n1]

The title compound was prepared in an analogous manner to Example 4 using 8-chloro-7-iodo-2-(methoxymethyl)-[1,2,4]triazolo[1,5-a]pyridine (Intermediate 24) in Step A. MS (ESI): mass calcd. for C$_{22}$H$_{15}$FN$_5$O, 387.1; m/z found, 388.2 [M+H]$^+$. $^1$H NMR (600 MHz, DMSO-d$_6$) δ 13.17 (s, 1H), 8.95 (d, J=7.0 Hz, 1H), 8.03 (s, 1H), 7.52 (s, 1H), 7.28-7.24 (m, 3H), 7.10 (t, J=8.9 Hz, 2H), 6.99 (s, 1H), 4.57 (s, 2H), 3.33 (s, 3H), 2.42 (s, 3H).

Example 48

2-Cyclopropyl-7-(4-fluorophenyl)-8-(7-methyl-1H-indazol-5-yl)-[1,2,4]triazolo[1,5-a]pyridine

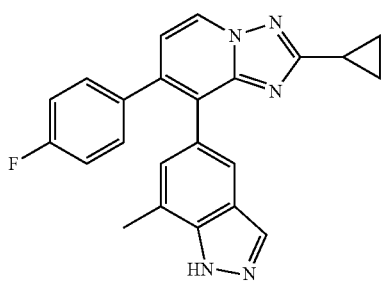 [SMILES: Cc1cc(-c2c(-c3ccc(F)cc3)ccn3nc(C4CC4)nc23)cc2cn[nH]c12]

The title compound was prepared in an analogous manner to Example 4 using 8-chloro-2-cyclopropyl-7-iodo-[1,2,4]triazolo[1,5-a]pyridine (Intermediate 26) at 90° C. for 6 h in Step A. MS (ESI): mass calcd. for $C_{23}H_{18}FN_5$, 383.2; m/z found, 384.1 [M+H]$^+$. $^1$H NMR (600 MHz, DMSO-d$_6$) δ 13.15 (s, 1H), 8.82 (d, J=7.0 Hz, 1H), 8.01 (s, 1H), 7.49 (s, 1H), 7.25-7.20 (m, 2H), 7.15 (d, J=7.0 Hz, 1H), 7.08 (t, J=8.9 Hz, 2H), 6.97 (s, 1H), 2.41 (s, 3H), 2.15-2.08 (m, 1H), 1.04-0.98 (m, 2H), 0.93-0.88 (m, 2H).

Example 49

7-Isopropyl-8-(7-methyl-1H-indazol-5-yl)-2-(trifluoromethyl)-[1,2,4]triazolo[1,5-a]pyridine

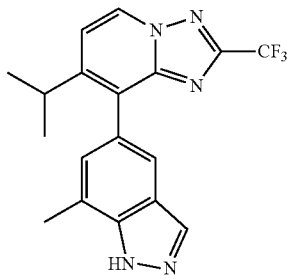

The title compound was prepared in a manner analogous to Example 4 using isopropylboronic acid pinacol ester and 8-chloro-7-iodo-2-(trifluoromethyl)-[1,2,4]triazolo[1,5-a]pyridine (Intermediate 19) in Step A. MS (ESI): mass calcd. for $C_{18}H_{16}F_3N_5$, 359.1; m/z found, 360.1 [M+H]$^+$. $^1$H NMR (400 MHz, CDCl$_3$) δ 10.80 (s, 1H), 8.01 (s, 1H), 7.89 (d, J=9.4 Hz, 1H), 7.77 (d, J=9.4 Hz, 1H), 7.57 (dd, J=1.4, 0.7 Hz, 1H), 7.09 (t, J=1.2 Hz, 1H), 3.04-2.90 (m, 1H), 2.52 (s, 3H), 1.24 (d, J=6.9 Hz, 3H), 1.18 (d, J=6.9 Hz, 3H).

Example 50

8-(1H-Indazol-5-yl)-7-methyl-2-(trifluoromethyl)imidazo[1,2-a]pyridine

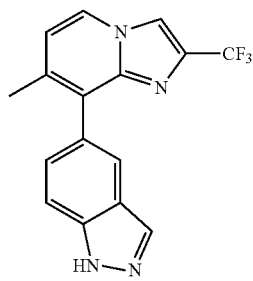 [SMILES: Cc1ccn2cc(C(F)(F)F)nc2c1-c1ccc2[nH]ncc2c1]

The title compound was prepared in a manner analogous to Example 11 using 8-bromo-7-methyl-2-(trifluoromethyl)imidazo[1,2-a]pyridine (Intermediate 40) and 5-(4,4,5,5-tetramethyl-1,3,2-dioxaborolan-2-yl)-1H-indazole. MS (ESI): mass calcd. for $C_{16}H_{11}F_3N_4$, 316.1; m/z found, 317.1 [M+H]$^+$. $^1$H NMR (500 MHz, DMSO-d$_6$) δ 13.18 (s, 1H), 8.52-8.48 (m, 2H), 8.14 (d, J=1.0 Hz, 1H), 7.82-7.79 (m, 1H), 7.65 (d, J=8.6 Hz, 1H), 7.37 (dd, J=8.5, 1.5 Hz, 1H), 7.07 (d, J=7.0 Hz, 1H), 2.23 (s, 3H).

Example 51

7-Fluoro-5-[7-methyl-2-(trifluoromethyl)imidazo[1,2-a]pyridin-8-yl]indolin-2-one

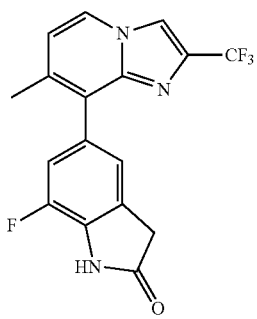 [SMILES: Cc1ccn2cc(C(F)(F)F)nc2c1-c1cc(F)c2c(c1)CC(=O)N2]

The title compound was prepared in a manner analogous to Example 11 using 8-bromo-7-methyl-2-(trifluoromethyl)imidazo[1,2-a]pyridine (Intermediate 40) and 7-fluoro-5-(4,4,5,5-tetramethyl-1,3,2-dioxaborolan-2-yl)indolin-2-one (Intermediate 6) at 130° C. Crude product after work-up was triturated in a mixture of EtOAc/Hexanes (1:1), the solids filtered, and washed with EtOAc/Hexanes (1:1). MS (ESI): mass calcd. for $C_{17}H_{11}F_4N_3O$, 349.1; m/z found, 349.7 [M+H]$^+$. $^1$H NMR (500 MHz, DMSO-d$_6$) δ 10.98 (s, 1H), 8.50-8.47 (m, 2H), 7.20-7.15 (m, 1H), 7.13-7.10 (m, 1H), 7.04 (d, J=7.0 Hz, 1H), 3.64 (s, 2H), 2.24 (s, 3H).

Example 52

7-Methyl-8-(7-methyl-1H-indazol-5-yl)-2-(trifluoromethyl)imidazo[1,2-a]pyridine

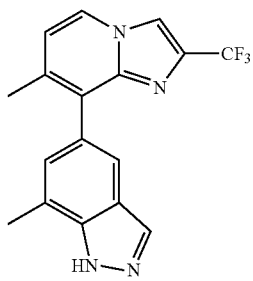 [SMILES: Cc1ccn2cc(C(F)(F)F)nc2c1-c1cc(C)c2[nH]ncc2c1]

The title compound was prepared in a manner analogous to Example 11 using 8-bromo-7-methyl-2-(trifluoromethyl)imidazo[1,2-a]pyridine (Intermediate 40) and 7-methyl-5-(4,4,5,5-tetramethyl-1,3,2-dioxaborolan-2-yl)-1H-indazole (Intermediate 2) at 140° C. MS (ESI): mass calcd. for $C_{17}H_{13}F_3N_4$, 330.1; m/z found, 331.1 [M+H]$^+$. $^1$H NMR (500 MHz, DMSO-d$_6$) δ 13.26 (s, 1H), 8.51-8.48 (m, 2H), 8.12 (s, 1H), 7.60-7.58 (m, 1H), 7.13-7.11 (m, 1H), 7.06 (d, J=7.0 Hz, 1H), 2.57 (s, 3H), 2.21 (s, 3H).

Example 53

2-tert-Butyl-7-methyl-8-(7-methyl-1H-indazol-5-yl)imidazo[1,2-a]pyridine

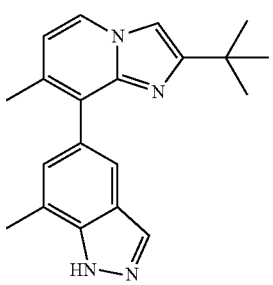 [SMILES: Cc1ccn2cc(C(C)(C)C)nc2c1-c1cc(C)c2[nH]ncc2c1]

The title compound was prepared in a manner analogous to Example 11 using 8-bromo-2-(tert-butyl)-7-methylimidazo[1,2-a]pyridine (Intermediate 41) and 7-methyl-5-(4,4,5,5-tetramethyl-1,3,2-dioxaborolan-2-yl)-1H-indazole (Intermediate 2). MS (ESI): mass calcd. for $C_{20}H_{22}N_4$, 318.2; m/z found, 319.2 [M+H]$^+$. $^1$H NMR (500 MHz, Methanol-d$_4$) δ 8.21 (d, J=6.9 Hz, 1H), 8.08 (s, 1H), 7.59-7.56 (m, 1H), 7.54 (s, 1H), 7.15-7.13 (m, 1H), 6.80 (d, J=6.9 Hz, 1H), 2.63-2.61 (m, 3H), 2.16 (s, 3H), 1.30 (s, 9H).

Example 54

5-(2-tert-Butyl-7-methyl-imidazo[1,2-a]pyridin-8-yl)-7-methyl-indolin-2-one

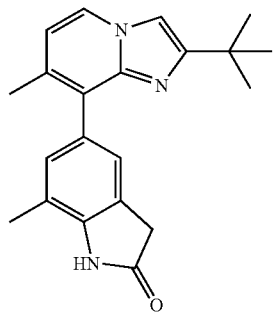 [SMILES: Cc1cc(-c2c(C)ccn3cc(C(C)(C)C)nc23)cc2c1NC(=O)C2]

The title compound was prepared in a manner analogous to Example 11 using 8-bromo-2-(tert-butyl)-7-methylimidazo[1,2-a]pyridine (Intermediate 41) and 7-methyl-5-(4,4,5,5-tetramethyl-1,3,2-dioxaborolan-2-yl)indolin-2-one (Intermediate 5). MS (ESI): mass calcd. for $C_{11}H_{23}N_3O$, 333.2; m/z found, 334.2 [M+H]$^+$. $^1$H NMR (500 MHz, DMSO-d$_6$) δ 10.51 (s, 1H), 8.28 (d, J=6.9 Hz, 1H), 7.59 (s, 1H), 7.07 (s, 1H), 7.04-7.02 (m, 1H), 6.73 (d, J=6.9 Hz, 1H), 3.53 (s, 2H), 2.24 (s, 3H), 2.15 (s, 3H), 1.24 (s, 9H).

Example 55

7-Methyl-5-(7-methyl-2-phenyl-imidazo[1,2-a]pyridin-8-yl)indolin-2-one

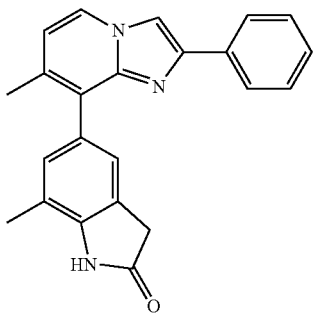 [SMILES: Cc1cc(-c2c(C)ccn3cc(-c4ccccc4)nc23)cc2c1NC(=O)C2]

The title compound was prepared in a manner analogous to Example 11 using 8-bromo-7-methyl-2-phenylimidazo[1,2-a]pyridine (Intermediate 42) and 7-methyl-5-(4,4,5,5-tetramethyl-1,3,2-dioxaborolan-2-yl)indolin-2-one (Intermediate 5) at 140° C. MS (ESI): mass calcd. for $C_{23}H_{19}N_3O$, 353.2; m/z found, 354.2 [M+H]$^+$. $^1$H NMR (500 MHz, DMSO-d$_6$) δ 10.54 (s, 1H), 8.38 (d, J=6.9 Hz, 1H), 7.85-7.80 (m, 2H), 7.40-7.35 (m, 2H), 7.29-7.24 (m, 1H), 7.13 (s, 1H), 7.08 (s, 1H), 6.84 (d, J=6.9 Hz, 1H), 3.57 (s, 2H), 2.27 (s, 3H), 2.19 (s, 3H).

Example 56

7-Methyl-8-(7-methyl-1H-indazol-5-yl)-2-phenyl-imidazo[1,2-a]pyridine

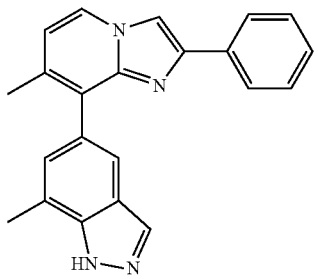 [SMILES: Cc1ccn2cc(-c3ccccc3)nc2c1-c1cc(C)c2[nH]ncc2c1]

The title compound was prepared in a manner analogous to Example 11 using 8-bromo-7-methyl-2-phenylimidazo[1,2-a]pyridine (Intermediate 42) and 7-methyl-5-(4,4,5,5-tetramethyl-1,3,2-dioxaborolan-2-yl)-1H-indazole (Intermediate 2) at 140° C. MS (ESI): mass calcd. for $C_{22}H_{18}N_4$, 338.2; m/z found, 339.2 [M+H]$^+$. $^1$H NMR (500 MHz, DMSO-$d_6$) δ 13.23 (s, 1H), 8.42 (d, J=6.9 Hz, 1H), 8.35 (s, 1H), 8.12 (s, 1H), 7.82-7.78 (m, 2H), 7.65-7.62 (m, 1H), 7.38-7.33 (m, 2H), 7.28-7.22 (m, 1H), 7.22-7.19 (m, 1H), 6.88 (d, J=6.9 Hz, 1H), 2.59 (s, 3H), 2.19 (s, 3H).

Example 57

2-Cyclopropyl-7-methyl-8-(7-methyl-1H-indazol-5-yl)imidazo[1,2-a]pyridine

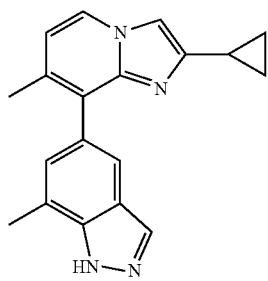 [SMILES: Cc1ccn2cc(C3CC3)nc2c1-c1cc(C)c2[nH]ncc2c1]

The title compound was prepared in a manner analogous to Example 11 using 8-bromo-2-cyclopropyl-7-methylimidazo[1,2-a]pyridine (Intermediate 43) and 7-methyl-5-(4,4,5,5-tetramethyl-1,3,2-dioxaborolan-2-yl)-1H-indazole (Intermediate 2) at 140° C. MS (ESI): mass calcd. for $C_{19}H_{18}N_4$, 302.2; m/z found, 303.2 [M+H]$^+$. $^1$H NMR (500 MHz, DMSO-$d_6$) δ 13.20 (s, 1H), 8.28 (d, J=6.9 Hz, 1H), 8.09 (s, 1H), 7.60 (s, 1H), 7.55-7.52 (m, 1H), 7.12-7.09 (m, 1H), 6.77 (d, J=6.9 Hz, 1H), 2.55 (s, 3H), 2.14 (s, 3H), 1.92-1.85 (m, 1H), 0.83-0.78 (m, 2H), 0.64-0.60 (m, 2H).

Example 58

5-[7-Methoxy-2-(trifluoromethyl)imidazo[1,2-a]pyridin-8-yl]-7-methyl-indolin-2-one

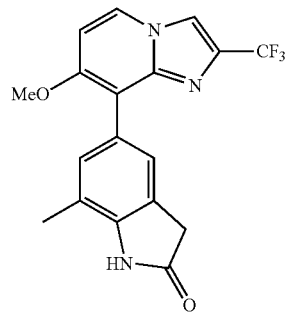 [SMILES: COc1ccn2cc(C(F)(F)F)nc2c1-c1cc(C)c2c(c1)CC(=O)N2]

The title compound was prepared in a manner analogous to Example 11 using 8-iodo-7-methoxy-2-(trifluoromethyl)imidazo[1,2-a]pyridine (Intermediate 44) and 7-methyl-5-(4,4,5,5-tetramethyl-1,3,2-dioxaborolan-2-yl)indolin-2-one (Intermediate 5) at 130° C. MS (ESI): mass calcd. for $C_{18}H_{14}F_3N_3O_2$, 361.1; m/z found, 362.01 [M+H]$^+$. $^1$H NMR (400 MHz, Methanol-$d_4$) δ 8.55 (d, J=7.7 Hz, 1H), 8.35-8.32 (m, 1H), 7.32 (d, J=7.6 Hz, 1H), 7.24-7.21 (m, 1H), 7.21-7.18 (m, 1H), 3.94 (s, 3H), 3.59 (s, 2H), 2.31 (s, 1H).

Example 59

7-Methoxy-8-(7-methyl-1H-indazol-5-yl)-2-(trifluoromethyl)imidazo[1,2-a]pyridine

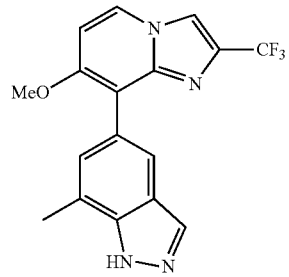 [SMILES: COc1ccn2cc(C(F)(F)F)nc2c1-c1cc(C)c2[nH]ncc2c1]

The title compound was prepared in a manner analogous to Example 11 using 8-iodo-7-methoxy-2-(trifluoromethyl)imidazo[1,2-a]pyridine (Intermediate 44) and 7-methyl-5-(4,4,5,5-tetramethyl-1,3,2-dioxaborolan-2-yl)-1H-indazole (Intermediate 2) at 130° C. MS (ESI): mass calcd. for $C_{17}H_{13}F_3N_4O$, 346.1; m/z found, 347.1 [M+H]$^+$. $^1$H NMR (400 MHz, Methanol-$d_4$) δ 8.60 (d, J=7.6 Hz, 1H), 8.40-8.36 (m, 1H), 8.10 (s, 1H), 7.78-7.75 (m, 1H), 7.37 (d, J=7.7 Hz, 1H), 7.30-7.27 (m, 1H), 3.95 (s, 3H), 2.61 (s, 3H).

Example 60

7-Chloro-8-(7-methyl-1H-indazol-5-yl)-2-(trifluoromethyl)imidazo[1,2-a]pyridine

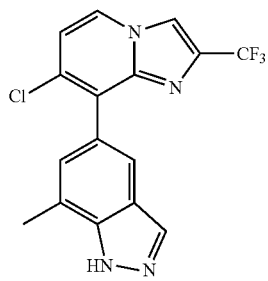 [SMILES: Cc1cc(-c2c(Cl)ccn3cc(C(F)(F)F)nc23)cc2cn[nH]c12]

The title compound was prepared in a manner analogous to Example 11 using Intermediate 45 and 7-methyl-5-(4,4,5,5-tetramethyl-1,3,2-dioxaborolan-2-yl)-1H-indazole (Intermediate 2) at 130° C., using Pd (PPh$_3$)$_4$ for catalyst. MS (ESI): mass calcd. for C$_{16}$H$_{10}$ClF$_3$N$_4$, 350.1; m/z found, 350.1 [M+H]$^+$. $^1$H NMR (500 MHz, DMSO-d$_6$) δ 13.32 (s, 1H), 8.64-8.60 (m, 2H), 8.15 (s, 1H), 7.71 (s, 1H), 7.30 (d, J=7.3 Hz, 1H), 7.20 (s, 1H), 2.58 (s, 3H).

Example 61

5-(2,7-Bis(trifluoromethyl)imidazo[1,2-a]pyridin-8-yl)-1H-indazole

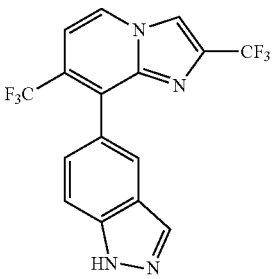 [SMILES: FC(F)(F)c1cn2ccc(C(F)(F)F)c(-c3ccc4[nH]ncc4c3)c2n1]

The title compound was prepared in a manner analogous to Example 11 using 8-chloro-2,7-bis(trifluoromethyl)imidazo[1,2-a]pyridine (Intermediate 47) and 5-(4,4,5,5-tetramethyl-1,3,2-dioxaborolan-2-yl)-1H-indazole. Microwave irradiation was employed (190° C. for 60 minutes). Pd(dppf)Cl$_2$-DCM used for catalyst. MS (ESI): mass calcd. for C$_{16}$H$_8$F$_6$N$_4$, 370.1; m/z found, 371.0 [M+H]$^+$. $^1$H NMR (500 MHz, MeOD) δ 8.67 (d, J=7.3 Hz, 1H), 8.50 (s, 1H), 8.12 (s, 1H), 7.84 (s, 1H), 7.65 (d, J=8.6 Hz, 1H), 7.42 (dd, J=8.6, 1.5 Hz, 1H), 7.37 (d, J=7.3 Hz, 1H).

Example 62

5-(2,7-Bis(trifluoromethyl)imidazo[1,2-a]pyridin-8-yl)-7-methyl-1H-indazole

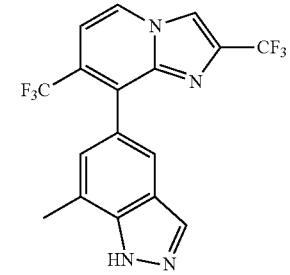 [SMILES: Cc1cc(-c2c(C(F)(F)F)ccn3cc(C(F)(F)F)nc23)cc2cn[nH]c12]

The title compound was prepared in a manner analogous to Example 11 using 8-chloro-2,7-bis(trifluoromethyl)imidazo[1,2-a]pyridine (Intermediate 47) and 7-methyl-5-(4,4,5,5-tetramethyl-1,3,2-dioxaborolan-2-yl)-1H-indazole (Intermediate 2). Microwave irradiation was employed (150° C. for 45 minutes). MS (ESI): mass calcd. for C$_{17}$H$_{10}$F$_6$N$_4$, 384.1; m/z found, 385.2 [M+H]$^+$. $^1$H NMR (600 MHz, DMSO-d$_6$) δ 13.30 (s, 1H), 8.80 (d, J=7.4 Hz, 1H), 8.78 (s, 1H), 8.14 (s, 1H), 7.61 (s, 1H), 7.44 (d, J=7.3 Hz, 1H), 7.14 (s, 1H), 2.57 (s, 3H).

Example 63

8-(7-Methyl-1H-indazol-5-yl)-2,7-bis(trifluoromethyl)imidazo[1,2-c]pyrimidine

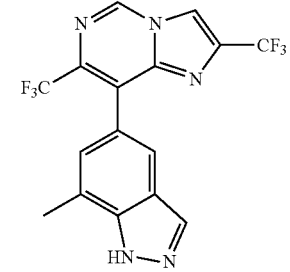 [SMILES: Cc1cc(-c2c(C(F)(F)F)ncn3cc(C(F)(F)F)nc23)cc2cn[nH]c12]

The title compound was prepared in a manner analogous to Example 13 using 8-bromo-2,7-bis(trifluoromethyl)imidazo[1,2-c]pyrimidine (Intermediate 48) and 7-methyl-5-(4,4,5,5-tetramethyl-1,3,2-dioxaborolan-2-yl)-1H-indazole (Intermediate 2). MS (ESI): mass calcd. for C$_{16}$H$_9$F$_6$N$_5$, 385.1; m/z found, 386.1 [M+H]$^+$. $^1$H NMR (500 MHz, MeOD) δ 9.44 (s, 1H), 8.60 (s, 1H), 8.13 (s, 1H), 7.72 (s, 1H), 7.25 (s, 1H), 2.64 (s, 3H).

Example 64

8-(7-Chloro-1H-indazol-5-yl)-2-ethyl-7-(trifluoromethyl)imidazo[1,2-c]pyrimidine

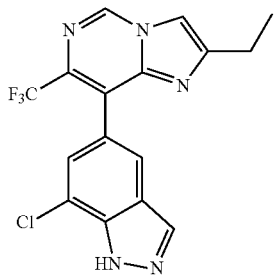 [SMILES: CCc1cn2cnc(C(F)(F)F)c(-c3cc(Cl)c4[nH]ncc4c3)c2n1]

The title compound was prepared in a manner analogous to Example 13 using 8-bromo-2-ethyl-7-(trifluoromethyl)imidazo[1,2-c]pyrimidine (Intermediate 50). MS (ESI): mass calcd. for $C_{16}H_{11}ClF_3N_5$, 365.1; m/z found, 366.0 [M+H]$^+$. $^1$H NMR (500 MHz, DMSO-d$_6$) δ 13.82 (s, 1H), 9.50 (s, 1H), 8.31 (s, 1H), 8.05 (s, 1H), 7.83 (s, 1H), 7.54 (s, 1H), 2.70 (q, J=7.5 Hz, 2H), 1.20 (t, J=7.5 Hz, 3H).

Example 65

2-Ethyl-8-(7-methyl-1H-indazol-5-yl)-7-(trifluoromethyl)imidazo[1,2-c]pyrimidine

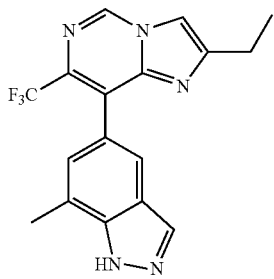 [SMILES: CCc1cn2cnc(C(F)(F)F)c(-c3cc(C)c4[nH]ncc4c3)c2n1]

The title compound was prepared in a manner analogous to Example 13 using 8-bromo-2-ethyl-7-(trifluoromethyl)imidazo[1,2-c]pyrimidine (Intermediate 50) and 7-methyl-5-(4,4,5,5-tetramethyl-1,3,2-dioxaborolan-2-yl)-1H-indazole (Intermediate 2). MS (ESI): mass calcd. for $C_{17}H_{14}F_3N_5$, 345.1; m/z found, 346.1 [M+H]$^+$. $^1$H NMR (600 MHz, DMSO-d$_6$) δ 13.31 (s, 1H), 9.46 (s, 1H), 8.14 (d, J=1.4 Hz, 1H), 8.03 (s, 1H), 7.62 (s, 1H), 7.15 (s, 1H), 2.69 (q, J=7.9 Hz, 2H), 2.57 (s, 3H), 1.20 (t, J=7.5 Hz, 3H).

Example 66

8-(7-Chloro-1H-indazol-5-yl)-2-isopropyl-7-(trifluoromethyl)imidazo[1,2-c]pyrimidine

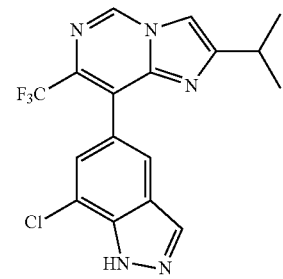 [SMILES: CC(C)c1cn2cnc(C(F)(F)F)c(-c3cc(Cl)c4[nH]ncc4c3)c2n1]

The title compound was prepared in a manner analogous to Example 13 using 8-bromo-2-isopropyl-7-(trifluoromethyl)imidazo[1,2-c]pyrimidine (Intermediate 51). MS (ESI): mass calcd. for $C_{17}H_{13}ClF_3N_5$, 379.1; m/z found, 380.1 [M+H]$^+$. $^1$H NMR (600 MHz, DMSO-d$_6$) δ 13.82 (s, 1H), 9.48 (s, 1H), 8.31 (s, 1H), 8.04 (s, 1H), 7.84 (d, J=1.1 Hz, 1H), 7.54 (d, J=0.9 Hz, 1H), 3.05-2.93 (m, 1H), 1.23 (d, J=6.9 Hz, 6H).

Example 67

8-(7-Chloro-1H-indazol-5-yl)-2-cyclopropyl-7-(trifluoromethyl)imidazo[1,2-c]pyrimidine

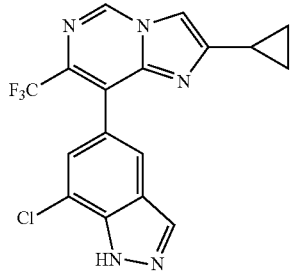 [SMILES: FC(F)(F)c1ncn2cc(C3CC3)nc2c1-c1cc(Cl)c2[nH]ncc2c1]

The title compound was prepared in a manner analogous to Example 13 using 8-bromo-2-cyclopropyl-7-(trifluoromethyl)imidazo[1,2-c]pyrimidine (Intermediate 49). MS (ESI): mass calcd. for $C_{17}H_{11}ClF_3N_5$, 377.1; m/z found, 378.1[M+H]$^+$. $^1$H NMR (600 MHz, DMSO-d$_6$) δ 13.80 (s, 1H), 9.44 (s, 1H), 8.30 (s, 1H), 8.03 (s, 1H), 7.82 (d, J=1.3 Hz, 1H), 7.52 (s, 1H), 2.09-2.02 (m, 1H), 0.95-0.89 (m, 2H), 0.75-0.70 (m, 2H).

Example 68

2-Cyclopropyl-8-(7-methyl-1H-indazol-5-yl)-7-(trifluoromethyl)imidazo[1,2-c]pyrimidine

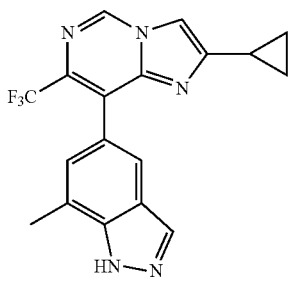 [SMILES: Cc1cc(-c2c(C(F)(F)F)ncn3cc(C4CC4)nc23)cc2cn[nH]c12]

The title compound was prepared in a manner analogous to Example 13 using 8-bromo-2-cyclopropyl-7-(trifluoromethyl)imidazo[1,2-c]pyrimidine (Intermediate 49) and 7-methyl-5-(4,4,5,5-tetramethyl-1,3,2-dioxaborolan-2-yl)-1H-indazole (Intermediate 2). MS (ESI): mass calcd. for $C_{18}H_{14}F_3N_5$, 357.1; m/z found, 358.1 [M+H]$^+$. $^1$H NMR (500 MHz, DMSO-d$_6$) δ 13.28 (s, 1H), 9.41 (s, 1H), 8.16-8.12 (m, 1H), 8.02 (s, 1H), 7.61 (s, 1H), 7.14 (s, 1H), 2.57 (s, 3H), 2.09-2.00 (m, 1H), 0.96-0.88 (m, 2H), 0.75-0.68 (m, 2H).

Example 69

7-Chloro-5-[2-cyclopropyl-7-(trifluoromethyl)imidazo[1,2-c]pyrimidin-8-yl]indolin-2-one

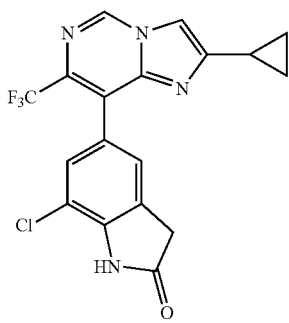

The title compound was prepared in a manner analogous to Example 13 using 8-bromo-2-cyclopropyl-7-(trifluoromethyl)imidazo[1,2-c]pyrimidine (Intermediate 49) and 7-chloro-5-(4,4,5,5-tetramethyl-1,3,2-dioxaborolan-2-yl)indolin-2-one (Intermediate 7). MS (ESI): mass calcd. for $C_{18}H_{12}ClF_3N_4O$, 392.1; m/z found, 393.0 [M+H]$^+$. $^1$H NMR (400 MHz, DMSO-d$_6$) δ 10.99 (s, 1H), 9.41 (s, 1H), 8.01 (s, 1H), 7.27 (dd, J=34.4, 1.6 Hz, 2H), 3.70 (s, 2H), 2.07 (tt, J=8.3, 4.9 Hz, 1H), 0.95 (ddd, J=8.3, 6.4, 3.9 Hz, 2H), 0.81-0.64 (m, 2H).

Example 70

5-[2-Cyclopropyl-7-(trifluoromethyl)imidazo[1,2-c]pyrimidin-8-yl]-7-fluoro-indolin-2-one

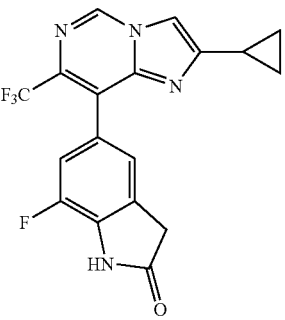 [SMILES: O=C1Cc2cc(-c3c(C(F)(F)F)ncn4cc(C5CC5)nc34)cc(F)c2N1]

The title compound was prepared in a manner analogous to Example 13 using 8-bromo-2-cyclopropyl-7-(trifluoromethyl)imidazo[1,2-c]pyrimidine (Intermediate 49) and 7-fluoro-5-(4,4,5,5-tetramethyl-1,3,2-dioxaborolan-2-yl)indolin-2-one (Intermediate 6). MS (ESI): mass calcd. for $C_{18}H_{12}F_4N_4O$, 376.1; m/z found, 377.1 [M+H]$^+$. $^1$H NMR (400 MHz, DMSO-d$_6$) δ 10.69 (d, J=2.5 Hz, 1H), 9.43 (s, 1H), 8.03 (s, 1H), 6.88-6.72 (m, 2H), 3.66 (s, 2H), 2.12-2.04 (m, 1H), 0.97-0.92 (m, 2H), 0.78-0.73 (m, 2H).

Example 71

8-(7-Chloro-1H-indazol-5-yl)-7-isopropyl-2-(trifluoromethyl)imidazo[1,2-c]pyrimidine

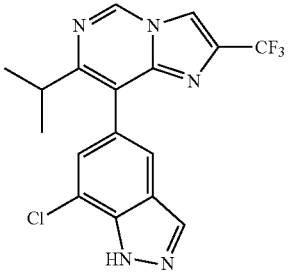 [SMILES: CC(C)c1ncn2cc(C(F)(F)F)nc2c1-c1cc(Cl)c2[nH]ncc2c1]

The title compound was prepared in a manner analogous to Example 13 using 8-bromo-7-isopropyl-2-(trifluoromethyl)imidazo[1,2-c]pyrimidine (Intermediate 52). MS (ESI): mass calcd. for $C_{17}H_{13}ClF_3N_5$, 379.1; m/z found, 380.1 [M+H]$^+$. $^1$H NMR (600 MHz, DMSO-d$_6$) δ 13.81 (s, 1H), 9.47 (s, 1H), 8.62 (d, J=1.1 Hz, 1H), 8.30 (s, 1H), 7.82 (d, J=1.3 Hz, 1H), 7.50 (d, J=1.3 Hz, 1H), 3.04-2.94 (m, 1H), 1.18 (d, J=6.6 Hz, 6H).

Example 72

8-(7-Chloro-1H-indazol-5-yl)-2-(difluoromethyl)-7-isopropyl-imidazo[1,2-c]pyrimidine

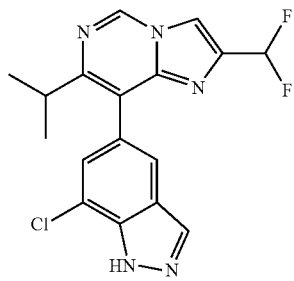 [SMILES: CC(C)c1ncn2cc(C(F)F)nc2c1-c1cc(Cl)c2[nH]ncc2c1]

The title compound was prepared in a manner analogous to Example 13 using 8-bromo-2-(difluoromethyl)-7-isopropylimidazo[1,2-c]pyrimidine (Intermediate 53). MS (ESI): mass calcd. for $C_{17}H_{14}ClF_2N_5$, 361.1; m/z found, 362.1 [M+H]$^+$. $^1$H NMR (600 MHz, DMSO-d$_6$) δ 13.79 (s, 1H), 9.46 (s, 1H), 8.33 (t, J=1.9 Hz, 1H), 8.29 (s, 1H), 7.80 (d, J=1.3 Hz, 1H), 7.49 (d, J=1.3 Hz, 1H), 7.12 (t, J$_{(H-F)}$=54.5 Hz, 1H), 3.04-2.95 (m, 1H), 1.18 (d, J=6.6 Hz, 6H).

Example 73

8-(7-Chloro-1H-indazol-5-yl)-7-ethyl-2-(trifluoromethyl)imidazo[1,2-c]pyrimidine

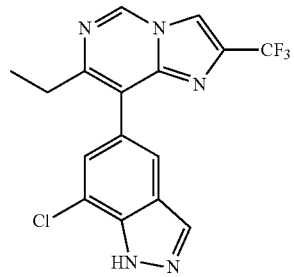 [SMILES: CCc1ncn2cc(C(F)(F)F)nc2c1-c1cc(Cl)c2[nH]ncc2c1]

The title compound was prepared in a manner analogous to Example 13 using 8-bromo-7-ethyl-2-(trifluoromethyl)imidazo[1,2-c]pyrimidine (Intermediate 54). MS (ESI): mass calcd. for $C_{16}H_{14}ClF_3N_5$, 365.1; m/z found, 366.0 [M+H]$^+$. $^1$H NMR (400 MHz, DMSO-d$_6$) δ 13.80 (s, 1H), 9.44 (s, 1H), 8.69-8.59 (m, 1H), 8.30 (d, J=1.3 Hz, 1H), 7.85 (d, J=1.3 Hz, 1H), 7.62-7.46 (m, 1H), 2.69-2.59 (m, 2H), 1.18 (t, J=7.5 Hz, 3H).

Example 74

7-Ethyl-8-(7-methyl-1H-indazol-5-yl)-2-(trifluoromethyl)imidazo[1,2-c]pyrimidine

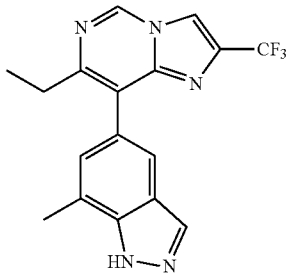 [SMILES: CCc1ncn2cc(C(F)(F)F)nc2c1-c1cc(C)c2[nH]ncc2c1]

The title compound was prepared in a manner analogous to Example 13 using 8-bromo-7-ethyl-2-(trifluoromethyl)imidazo[1,2-c]pyrimidine (Intermediate 54) and 7-methyl-5-(4,4,5,5-tetramethyl-1,3,2-dioxaborolan-2-yl)-1H-indazole (Intermediate 2). MS (ESI): mass calcd. for $C_{17}H_{14}F_3N_5$, 345.1; m/z found, 346.0 [M+H]$^+$. $^1$H NMR (400 MHz, DMSO-d$_6$) δ 13.32 (s, 1H), 9.41 (s, 1H), 8.60 (q, J=1.1 Hz, 1H), 8.22-8.07 (m, 1H), 7.64 (t, J=1.0 Hz, 1H), 7.15 (t, J=1.3 Hz, 1H), 2.63-2.57 (m, 5H), 1.17 (t, J=7.5 Hz, 3H).

Example 75

8-(7-Chloro-1H-indazol-5-yl)-2-(difluoromethyl)-7-ethyl-imidazo[1,2-c]pyrimidine

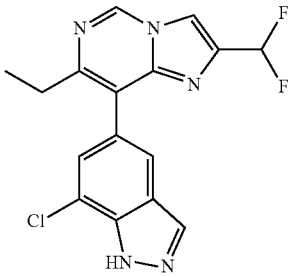 [SMILES: CCc1ncn2cc(C(F)F)nc2c1-c1cc(Cl)c2[nH]ncc2c1]

The title compound was prepared in a manner analogous to Example 13 using 8-bromo-2-(difluoromethyl)-7-ethyl-imidazo[1,2-c]pyrimidine (Intermediate 55). MS (ESI): mass calcd. for $C_{16}H_{12}ClF_2N_5$, 347.1; m/z found, 348.0 [M+H]$^+$. $^1$H NMR (400 MHz, DMSO-d$_6$) δ 13.78 (s, 1H), 9.43 (s, 1H), 8.34 (t, J=2.0 Hz, 1H), 8.29 (s, 1H), 7.83 (d, J=1.3 Hz, 1H), 7.52 (d, J=1.4 Hz, 1H), 7.27-6.96 (m, 1H), 2.61 (q, J=7.5 Hz, 2H), 1.18 (t, J=7.4 Hz, 3H).

Example 76

8-(7-Chloro-1H-indazol-5-yl)-7-methyl-2-(trifluoromethyl)imidazo[1,2-c]pyrimidine

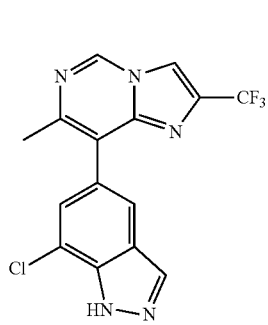 [SMILES: Cc1ncn2cc(C(F)(F)F)nc2c1-c1cc(Cl)c2[nH]ncc2c1]

The title compound was prepared in a manner analogous to Example 13 using 8-bromo-7-methyl-2-(trifluoromethyl)imidazo[1,2-c]pyrimidine (Intermediate 56). MS (ESI): mass calcd. for $C_{15}H_9ClF_3N_5$, 351.0; m/z found, 352.0 [M+H]$^+$. $^1$H NMR (400 MHz, DMSO-d$_6$) δ 13.84 (s, 1H), 9.39 (s, 1H), 8.71-8.51 (m, 1H), 8.30 (s, 1H), 8.03-7.80 (m, 1H), 7.57 (d, J=1.3 Hz, 1H), 2.38 (s, 3H).

Example 77

8-(7-Chloro-1H-indazol-5-yl)-7-cyclopropyl-2-(trifluoromethyl)imidazo[1,2-c]pyrimidine

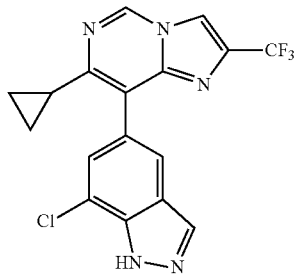 [SMILES: FC(F)(F)c1cn2cnc(C3CC3)c(-c3cc(Cl)c4[nH]ncc4c3)c2n1]

The title compound was prepared in a manner analogous to Example 13 using 8-bromo-7-cyclopropyl-2-(trifluoromethyl)imidazo[1,2-c]pyrimidine (Intermediate 57). MS (ESI): mass calcd. for $C_{17}H_{11}ClF_3N_5$, 377.7; m/z found, 378.0 [M+H]$^+$. $^1$H NMR (600 MHz, DMSO-d$_6$) δ 13.77 (s, 1H), 9.33 (s, 1H), 8.56 (d, J=1.1 Hz, 1H), 8.31 (s, 1H), 7.93 (d, J=1.3 Hz, 1H), 7.59 (d, J=1.3 Hz, 1H), 2.03-1.88 (m, 1H), 1.11-1.04 (m, 2H), 0.95-0.88 (m, 2H).

Example 78

8-(7-Chloro-1H-indazol-5-yl)-7-cyclopropyl-2-(difluoromethyl)imidazo[1,2-c]pyrimidine

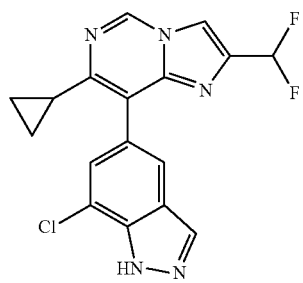 [SMILES: FC(F)c1cn2cnc(C3CC3)c(-c3cc(Cl)c4[nH]ncc4c3)c2n1]

The title compound was prepared in a manner analogous to Example 13 using 8-bromo-7-cyclopropyl-2-(difluoromethyl)imidazo[1,2-c]pyrimidine (Intermediate 58). MS (ESI): mass calcd. for $C_{17}H_{12}ClF_2N_5$, 359.7; m/z found, 360.0 [M+H]$^+$. $^1$H NMR (600 MHz, DMSO-d$_6$) δ 13.76 (s, 1H), 9.32 (s, 1H), 8.30 (s, 1H), 8.28 (t, J=2.0 Hz, 1H), 7.92 (d, J=1.2 Hz, 1H), 7.58 (d, J=1.3 Hz, 1H), 7.10 (t, J$_{(H-F)}$=54.5 Hz, 1H), 1.98-1.91 (m, 1H), 1.08-1.03 (m, 2H), 0.93-0.88 (m, 2H).

Example 79

8-(7-Chloro-1H-indazol-5-yl)-7-cyclopropyl-5-methyl-2-trifluoromethyl)imidazo[1,2-c]pyrimidine

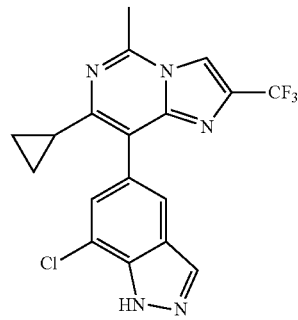 [SMILES: Cc1nc(C2CC2)c(-c2cc(Cl)c3[nH]ncc3c2)c2nc(C(F)(F)F)cn12]

The title compound was prepared in a manner analogous to Example 13 using 8-bromo-7-cyclopropyl-5-methyl-2-(trifluoromethyl)imidazo[1,2-c]pyrimidine (Intermediate 59). MS (ESI): mass calcd. for $C_{18}H_{13}ClF_3N_5$, 391.1; m/z found, 392.1 [M+H]$^+$. $^1$H NMR (500 MHz, DMSO-d$_6$) δ 13.78 (s, 1H), 8.61 (q, J=1.3 Hz, 1H), 8.31-8.29 (m, 1H), 7.89 (t, J=1.5 Hz, 1H), 7.55 (t, J=1.5 Hz, 1H), 2.81 (d, J=1.5 Hz, 3H), 1.96-1.90 (m, 1H), 1.08-1.04 (m, 2H), 0.91-0.87 (m, 2H).

Example 80

8-(7-Chloro-1H-indazol-5-yl)-7-cyclopropyl-2-(difluoromethyl)-5-methyl-imidazo[1,2-c]pyrimidine

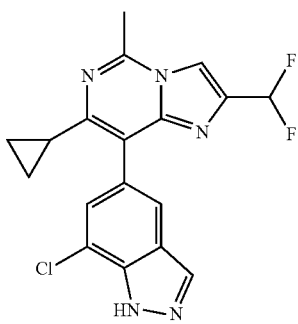 [SMILES: Cc1nc(C2CC2)c(-c2cc(Cl)c3[nH]ncc3c2)c2nc(C(F)F)cn12]

The title compound was prepared in a manner analogous to Example 13 using 8-bromo-7-cyclopropyl-2-(difluoromethyl)-5-methylimidazo[1,2-c]pyrimidine (Intermediate 60). MS (ESI): mass calcd. for $C_{18}H_{14}ClF_2N_5$, 373.1; m/z found, 374.1 [M+H]$^+$. $^1$H NMR (400 MHz, DMSO-d$_6$) δ 13.75 (s, 1H), 8.30-8.28 (m, 2H), 7.90 (d, J=1.3 Hz, 1H), 7.56 (d, J=1.3 Hz, 1H), 7.11 (t, $J_{(H-F)}$=54.6 Hz, 1H), 2.80 (s, 3H), 1.98-1.91 (m, 1H), 1.09-1.04 (m, 2H), 0.91-0.86 (m, 2H).

Example 81

3-Chloro-8-(7-chloro-1H-indazol-5-yl)-2-cyclopropyl-7-(trifluoromethyl)imidazo[1,2-c]pyrimidine

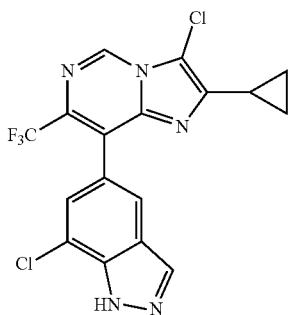 [SMILES: FC(F)(F)c1ncn2c(Cl)c(C3CC3)nc2c1-c1cc(Cl)c2[nH]ncc2c1]

The title compound was prepared in a manner analogous to Example 13 using 8-bromo-3-chloro-2-cyclopropyl-7-(trifluoromethyl)imidazo[1,2-c]pyrimidine (Intermediate 61). MS (ESI): mass calcd. for $C_{17}H_{10}Cl_2F_3N_5$, 411.0; m/z found, 411.9 [M+H]$^+$. $^1$H NMR (600 MHz, DMSO-d$_6$) δ 13.84 (s, 1H), 9.53 (s, 1H), 8.31 (s, 1H), 7.81 (d, J=1.3 Hz, 1H), 7.48 (s, 1H), 2.11-2.03 (m, 1H), 1.20-1.15 (m, 2H), 0.93-0.89 (m, 2H).

Example 82

8-(7-Chloro-1H-indazol-5-yl)-2-cyclopropyl-3-fluoro-7-(trifluoromethyl)imidazo[1,2-c]pyrimidine

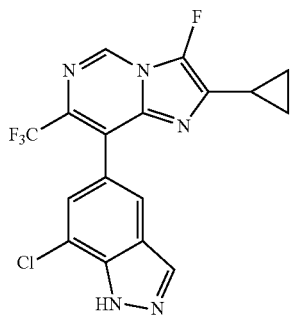 [SMILES: Fc1c(C2CC2)nc2c(-c3cc(Cl)c4[nH]ncc4c3)c(C(F)(F)F)ncn12]

The title compound was prepared in a manner analogous to Example 13 using 8-bromo-2-cyclopropyl-3-fluoro-7-(trifluoromethyl)imidazo[1,2-c]pyrimidine (Intermediate 62). MS (ESI): mass calcd. for $C_{17}H_{10}ClF_4N_5$, 395.1; m/z found, 396.0 [M+H]$^+$. $^1$H NMR (400 MHz, DMSO-d$_6$) δ 13.86 (s, 1H), 9.57 (s, 1H), 8.32 (s, 1H), 7.82 (d, J=1.2 Hz, 1H), 7.51 (d, J=1.3 Hz, 1H), 2.12-2.03 (m, 1H), 1.17-1.10 (m, 2H), 0.88-0.81 (m, 2H).

Example 83

7-Cyclopropyl-2-(difluoromethyl)-5-methyl-8-(7-(trifluoromethyl)-1H-indazol-5-yl)imidazo[1,2-c]pyrimidine

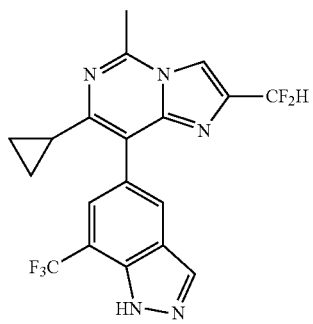 [SMILES: Cc1nc(C2CC2)c(-c2cc(C(F)(F)F)c3[nH]ncc3c2)c2nc(C(F)F)cn12]

The title compound may be prepared in a manner analogous to Example 1 by using 8-bromo-7-cyclopropyl-5-methyl-2-(trifluoromethyl)imidazo[1,2-c]pyrimidine (Intermediate 59) and 5-(4,4,5,5-tetramethyl-1,3,2-dioxaborolan-2-yl)-7-(trifluoromethyl)-1H-indazole, which can be prepared in a manner analogous to 7-chloro-5-(4,4,5,5-tetramethyl-1,3,2-dioxaborolan-2-yl)-1H-indazole (Intermediate 1).

Example 84

8-(7-Chloro-1H-indazol-5-yl)-7-(difluoromethyl)-2-ethyl-[1,2,4]triazolo[1,5-a]pyridine

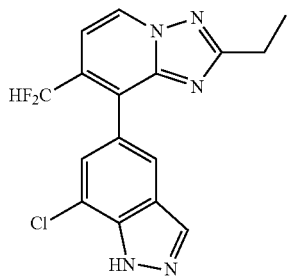

The title compound may be prepared in a manner analogous to Example 1 by using 7-chloro-5-(4,4,5,5-tetramethyl-1,3,2-dioxaborolan-2-yl)-1H-indazole (Intermediate 1) and 8-chloro-7-(difluoromethyl)-2-ethyl-[1,2,4]triazolo[1,5-a]pyridine, which can be prepared in a manner analogous to 8-chloro-7-(difluoromethyl)-2-(trifluoromethyl)-[1,2,4]triazolo[1,5-a]pyridine (Intermediate 38).

Example 85

8-(7-Chloro-1H-indazol-5-yl)-2-cyclopropyl-7-(difluoromethyl)-[1,2,4]triazolo[1,5-a]pyridine

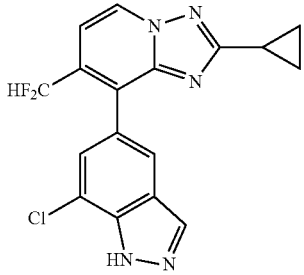

The title compound may be prepared in a manner analogous to Example 1 by using 7-chloro-5-(4,4,5,5-tetramethyl-1,3,2-dioxaborolan-2-yl)-1H-indazole (Intermediate 1) and 8-chloro-2-cyclopropyl-7-(difluoromethyl)-[1,2,4]triazolo[1,5-a]pyridine, which can be prepared in a manner analogous to 8-chloro-7-(difluoromethyl)-2-(trifluoromethyl)-[1,2,4]triazolo[1,5-a]pyridine. (Intermediate 38).

Example 86

5-(2,7-Bis(trifluoromethyl)imidazo[1,2-a]pyridin-8-yl)-7-chloroindolin-2-one

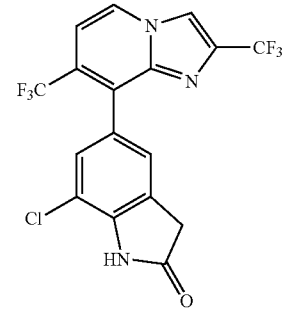 [SMILES: O=C1Cc2cc(-c3c(C(F)(F)F)ccn4cc(C(F)(F)F)nc34)cc(Cl)c2N1]

The title compound was be prepared in a manner analogous to Example 11 by using 7-chloro-5-(4,4,5,5-tetramethyl-1,3,2-dioxaborolan-2-yl)indolin-2-one (Intermediate 7) and 8-chloro-2,7-bis(trifluoromethyl)imidazo[1,2-a]pyridine (Intermediate 47). MS (ESI): mass calcd. for $C_{17}H_8ClF_6N_3O$, 419.0; m/z found, 420.0 [M+H]$^+$. $^1$H NMR (500 MHz, DMSO-d$_6$) δ 10.97 (s, 1H), 8.80 (d, J=7.2 Hz, 1H), 8.78 (s, 1H), 7.43 (d, J=7.3 Hz, 1H), 7.33-7.29 (m, 1H), 7.25-7.21 (m, 1H), 3.70 (s, 2H).

Example 87

5-(2,7-Bis(trifluoromethyl)imidazo[1,2-a]pyridin-8-yl)-7-methylindolin-2-one

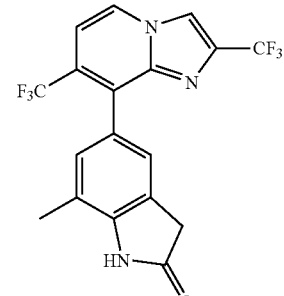

The title compound was be prepared in a manner analogous to Example 11 by using 7-methyl-5-(4,4,5,5-tetramethyl-1,3,2-dioxaborolan-2-yl)indolin-2-one (Intermediate 5) and 8-chloro-2,7-bis(trifluoromethyl)imidazo[1,2-a]pyridine (Intermediate 47). MS (ESI): mass calcd. for $C_{18}H_{11}F_6N_3O$, 399.1; m/z found, 400.1 [M+H]$^+$. $^1$H NMR (500 MHz, DMSO-d$_6$) δ 10.59 (s, 1H), 8.78-8.74 (m, 2H), 7.40 (d, J=7.3 Hz, 1H), 7.08-7.05 (m, 1H), 7.02-7.00 (m, 1H), 3.56 (s, 2H), 2.25 (s, 3H).

Example 88

5-(2,7-Bis(trifluoromethyl)imidazo[1,2-a]pyridin-8-yl)-7-chloro-1H-indazole

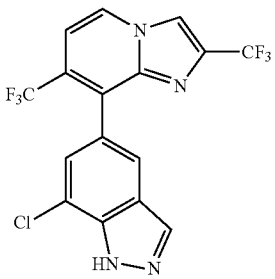 [SMILES: FC(F)(F)c1cn2ccc(C(F)(F)F)c(-c3cc(Cl)c4[nH]ncc4c3)c2n1]

The title compound was prepared in a manner analogous to Example 11 by using 7-chloro-5-(4,4,5,5-tetramethyl-1,3,2-dioxaborolan-2-yl)-1H-indazole (Intermediate 1) and 8-chloro-2,7-bis(trifluoromethyl)imidazo[1,2-a]pyridine (Intermediate 47). MS (ESI): mass calcd. for $C_{16}H_7ClF_6N_4$, 404.0; m/z found, 405.0 [M+H]$^+$. $^1$H NMR (300 MHz, DMSO-$d_6$) δ 13.84 (br s, 1H), 8.84 (d, J=7.2 Hz, 1H), 8.80 (s, 1H), 8.31 (s, 1H), 7.86-7.79 (m, 1H), 7.56-7.51 (m, 1H), 7.47 (d, J=7.3 Hz, 1H).

Example 89

8-(7-Chloro-1H-indazol-5-yl)-2-isopropyl-7-(trifluoromethyl)imidazo[1,2-a]pyridine

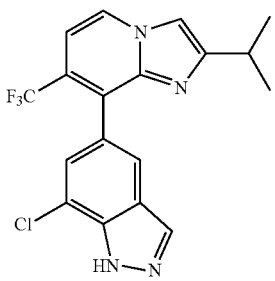

The title compound was prepared in a manner analogous to Example 11 by using 7-chloro-5-(4,4,5,5-tetramethyl-1,3,2-dioxaborolan-2-yl)-1H-indazole (Intermediate 1) and 8-chloro-2-isopropyl-7-(trifluoromethyl)imidazo[1,2-a]pyridine (Intermediate 66). MS (ESI): mass calcd. for $C_{18}H_{14}ClF_3N_4$, 378.1; m/z found, 379.1 [M+H]$^+$. $^1$H NMR (500 MHz, DMSO-$d_6$) δ 13.76 (s, 1H), 8.69 (d, J=7.3 Hz, 1H), 8.27 (d, J=1.5 Hz, 1H), 7.99 (s, 1H), 7.78-7.76 (m, 1H), 7.49-7.45 (m, 1H), 7.21 (d, J=7.2 Hz, 1H), 3.00-2.89 (m, 1H), 1.20 (d, J=6.9 Hz, 6H).

Example 90

2-Isopropyl-8-(7-methyl-1H-indazol-5-yl)-7-(trifluoromethyl)imidazo[1,2-a]pyridine

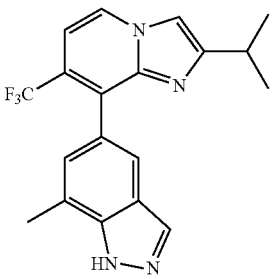 [SMILES: Cc1cc(-c2c(C(F)(F)F)ccn3cc(C(C)C)nc23)cc2cn[nH]c12]

The title compound was prepared in a manner analogous to Example 11 by using 7-methyl-5-(4,4,5,5-tetramethyl-1,3,2-dioxaborolan-2-yl)-1H-indazole (Intermediate 2) and 8-chloro-2-isopropyl-7-(trifluoromethyl)imidazo[1,2-a]pyridine (Intermediate 66). MS (ESI): mass calcd. for $C_{16}H_7ClF_6N_4$, 404.0; m/z found, 405.0 [M+H]$^+$. $^1$H NMR (500 MHz, DMSO-$d_6$) δ 13.27 (br s, 1H), 8.65 (d, J=7.2 Hz, 1H), 8.12 (d, J=1.2 Hz, 1H), 7.97-7.94 (m, 1H), 7.58-7.55 (m, 1H), 7.18 (d, J=7.2 Hz, 1H), 7.12-7.09 (m, 1H), 2.97-2.87 (m, 1H), 2.56 (s, 3H), 1.20 (d, J=6.9 Hz, 6H).

Example 91

2-Cyclopropyl-8-(7-methyl-1H-indazol-5-yl)-7-(trifluoromethyl)imidazo[1,2-a]pyridine

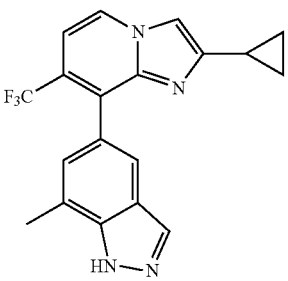 [SMILES: Cc1cc(-c2c(C(F)(F)F)ccn3cc(C4CC4)nc23)cc2cn[nH]c12]

The title compound was prepared in a manner analogous to Example 11 by using 7-methyl-5-(4,4,5,5-tetramethyl-1,3,2-dioxaborolan-2-yl)-1H-indazole (Intermediate 2) and 8-chloro-2-cyclopropyl-7-(trifluoromethyl)imidazo[1,2-a]pyridine (Intermediate 67). $^1$H NMR (500 MHz, DMSO-$d_6$) δ 13.27 (br s, 1H), 8.65 (d, J=7.2 Hz, 1H), 8.12 (d, J=1.2 Hz, 1H), 7.97-7.94 (m, 1H), 7.58-7.55 (m, 1H), 7.18 (d, J=7.2 Hz, 1H), 7.12-7.09 (m, 1H), 2.97-2.87 (m, 1H), 2.56 (s, 3H), 1.20 (d, J=6.9 Hz, 6H).

Example 92

2-Ethyl-8-(7-methyl-1H-indazol-5-yl)-7-(trifluoromethyl)imidazo[1,2-a]pyridine

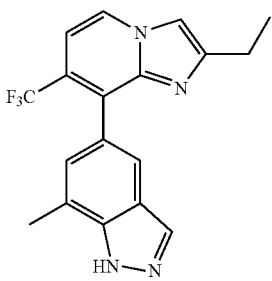 [SMILES: CCc1cn2ccc(C(F)(F)F)c(-c3cc(C)c4[nH]ncc4c3)c2n1]

The title compound was prepared in a manner analogous to Example 11 by using 7-methyl-5-(4,4,5,5-tetramethyl-1,3,2-dioxaborolan-2-yl)-1H-indazole (Intermediate 2) and 8-chloro-2-ethyl-7-(trifluoromethyl)imidazo[1,2-a]pyridine (Intermediate 65). $^1$H NMR (500 MHz, DMSO-$d_6$) δ 13.27 (s, 1H), 8.66 (d, J=7.1 Hz, 1H), 8.13-8.10 (m, 1H), 7.96 (s, 1H), 7.57-7.54 (m, 1H), 7.18 (d, J=7.2 Hz, 1H), 7.12-7.08 (m, 1H), 2.64 (q, J=7.5 Hz, 2H), 2.56 (s, 3H), 1.18 (t, J=7.6 Hz, 3H).

Example 93

2-(Difluoromethyl)-8-(7-methyl-1H-indazol-5-yl)-7-(trifluoromethyl)imidazo[1,2-a]pyridine

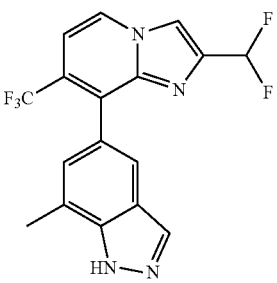 [SMILES: Cc1cc(-c2c(C(F)(F)F)ccn3cc(C(F)F)nc23)cc2cn[nH]c12]

The title compound was prepared in a manner analogous to Example 11 by using 7-methyl-5-(4,4,5,5-tetramethyl-1,3,2-dioxaborolan-2-yl)-1H-indazole (Intermediate 2) and 8-chloro-2-difluoromethyl-7-(trifluoromethyl)imidazo[1,2-a]pyridine (Intermediate 63). $^1$H NMR (300 MHz, DMSO-$d_6$) δ 13.32 (s, 1H), 8.80 (d, J=7.2 Hz, 1H), 8.56-8.45 (m, 1H), 8.18-8.08 (m, 1H), 7.66-7.54 (m, 1H), 7.37 (d, J=7.2 Hz, 1H), 7.15-7.09 (m, 1H), 7.12 (t, J=54.4 Hz, 1H), 2.56 (s, 3H).

Example 94

2-Methyl-8-(7-methyl-1H-indazol-5-yl)-7-(trifluoromethyl)imidazo[1,2-a]pyridine

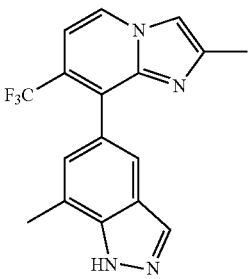 [SMILES: Cc1cn2ccc(C(F)(F)F)c(-c3cc(C)c4[nH]ncc4c3)c2n1]

The title compound was prepared in a manner analogous to Example 11 by using 7-methyl-5-(4,4,5,5-tetramethyl-1,3,2-dioxaborolan-2-yl)-1H-indazole (Intermediate 2) and 8-chloro-2-methyl-7-(trifluoromethyl)imidazo[1,2-a]pyridine (Intermediate 64). $^1$H NMR (500 MHz, DMSO-$d_6$) δ 13.27 (s, 1H), 8.65 (d, J=7.1 Hz, 1H), 8.11 (d, J=1.2 Hz, 1H), 7.95-7.92 (m, 1H), 7.57-7.53 (m, 1H), 7.18 (d, J=7.2 Hz, 1H), 7.11-7.08 (m, 1H), 2.56 (s, 3H), 2.27 (s, 3H).

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904).

An in vitro assay was used to determine the potency of test compounds as inhibitors of the glutamate response of the channel formed by GluA1o-γ8. To ensure a 1:1 stoichiometry of GluA1o and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): 633-640), the C-terminus of the cDNA for GRIA1o was fused to the N-terminus of the cDNA for γ8. The linker sequence was QQQQQQQQQQEFAT. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay.

Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$, 1 mM $MgCl_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 µM glutamate was monitored using a Molecular Devices FLIPR Tetra.

The fluorescence in each well was normalized to the fluorescence of negative and positive control wells. The negative control wells had no added compounds, and the positive control wells had been incubated with 10 µM CP465022 (a non-subtype-selective AMPA receptor antagonist) (Lazzaro et al. (2002). "Functional characterization of CP-465,022, a selective, noncompetitive AMPA receptor antagonist." *Neuropharmacology* 42(2): 143-153). The responses to glutamate as functions of the test compound concentrations were fitted to a four-parameter logistic function. The fitted parameter corresponding to the midpoint was taken to be the potency of inhibition of the compound. The data in Table 4 below illustrates the observed potency for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 4

| Ex # | Compound Name | pIC50 |
|---|---|---|
| 1 | 8-(7-Chloro-1H-indazol-5-yl)-2-(difluoromethyl)-7-(trifluoromethyl)-[1,2,4]triazolo[1,5-a]pyridine; | 9.5 |
| 2 | 7-Chloro-8-(7-methyl-1H-indazol-5-yl)-2-(trifluoromethyl)-[1,2,4]triazolo[1,5-a]pyridine; | 8.5 |
| 3 | 6-(2,7-Bis(trifluoromethyl)-[1,2,4]triazolo[1,5-a]pyridin-8-yl)benzo[d]thiazol-2(3H)-one; | 8.1 |
| 4 | 2-Cyclobutyl-7-(4-fluorophenyl)-8-(7-methyl-1H-indazol-5-yl)-[1,2,4]triazolo[1,5-a]pyridine; | 10.6 |
| 5 | 6-(7-(4-Fluorophenyl)-2-(trifluoromethyl)-[1,2,4]triazolo[1,5-a]pyridin-8-yl)benzo[d]thiazol-2(3H)-one; | 9.6 |
| 6 | 7-Cyclopentyl-8-(7-methyl-1H-indazol-5-yl)-2-(trifluoromethyl)-[1,2,4]triazolo[1,5-a]pyridine; | 10.1 |
| 7 | 7-(Azetidin-1-yl)-8-(7-methyl-1H-indazol-5-yl)-2-(trifluoromethyl)-[1,2,4]triazolo[1,5-a]pyridine; | 9.5 |
| 8 | 7-(3-Fluoroazetidin-1-yl)-8-(7-methyl-1H-indazol-5-yl)-2-(trifluoromethyl)-[1,2,4]triazolo[1,5-a]pyridine; | 8.6 |
| 9 | 2-Cyclopentyl-7-(4-fluorophenyl)-8-(7-methyl-1H-indazol-5-yl)-[1,2,4]triazolo[1,5-a]pyridine; | 10.8 |
| 10 | 8-(7-Methyl-1H-indazol-5-yl)-2-(trifluoromethyl)-[1,2,4]triazolo[1,5-a]pyridine-7-carbonitrile; | 7.7 |
| 11 | 7-Methyl-5-[7-methyl-2-(trifluoromethyl)imidazo[1,2-a]pyridin-8-yl]indolin-2-one; | 9.0 |
| 12 | 5-(7-(4-Fluorophenyl)-2-(trifluoromethyl)imidazo[1,2-a]pyridin-8-yl)-1H-indazole; | 8.5 |
| 13 | 8-(7-Chloro-1H-indazol-5-yl)-2,7-bis(trifluoromethyl)imidazo[1,2-c]pyrimidine; | 9.5 |
| 14 | 8-(7-Chloro-1H-indazol-5-yl)-2-(difluoromethyl)-7-(trifluoromethyl)imidazo[1,2-c]pyrimidine; | 9.4 |
| 15 | 2-(Difluoromethyl)-8-(7-methyl-1H-indazol-5-yl)-7-(trifluoromethyl)imidazo[1,2-c]pyrimidine; | 8.7 |
| 16 | 8-(7-Methyl-1H-indazol-5-yl)-2-(difluoromethyl)-7-(trifluoromethyl)-[1,2,4]triazolo[1,5-a]pyridine; | 9.0 |
| 17 | 7-Chloro-5-(2-(difluoromethyl)-7-(trifluoromethyl)-[1,2,4]triazolo[1,5-a]pyridin-8-yl)indolin-2-one; | 8.9 |
| 18 | 7-Methyl-5-(2-(difluoromethyl)-7-(trifluoromethyl)-[1,2,4]triazolo[1,5-a]pyridin-8-yl)indolin-2-one; | 8.6 |
| 19 | 8-(7-Chloro-1H-indazol-5-yl)-2,7-bis(trifluoromethyl)-[1,2,4]triazolo[1,5-a]pyridine; | 9.6 |
| 20 | 8-(7-Methyl-1H-indazol-5-yl)-2,7-bis(trifluoromethyl)-[1,2,4]triazolo[1,5-a]pyridine; | 9.3 |
| 21 | 5-(2,7-Bis(trifluoromethyl)-[1,2,4]triazolo[1,5-a]pyridin-8-yl)-7-chloroindolin-2-one; | 9.5 |
| 22 | 5-(2,7-Bis(trifluoromethyl)-[1,2,4]triazolo[1,5-a]pyridin-8-yl)-7-methylindolin-2-one; | 9.1 |
| 23 | 8-(7-Chloro-1H-indazol-5-yl)-7-(difluoromethyl)-2-(trifluoromethyl)-[1,2,4]triazolo[1,5-a]pyridine; | 9.4 |
| 24 | 8-(7-Methyl-1H-indazol-5-yl)-7-(difluoromethyl)-2-(trifluoromethyl)-[1,2,4]triazolo[1,5-a]pyridine; | 9.2 |
| 25 | 7-Chloro-5-(7-(difluoromethyl)-2-(trifluoromethyl)-[1,2,4]triazolo[1,5-a]pyridin-8-yl)indolin-2-one; | 9.2 |
| 26 | 7-Methyl-5-(7-(difluoromethyl)-2-(trifluoromethyl)-[1,2,4]triazolo[1,5-a]pyridin-8-yl)indolin-2-one; | 9.0 |
| 27 | 7-Methyl-8-(7-methyl-1H-indazol-5-yl)-2-(trifluoromethyl)-[1,2,4]triazolo[1,5-a]pyridine; | 8.4 |
| 28 | 7-Ethyl-8-(7-methyl-1H-indazol-5-yl)-2-(trifluoromethyl)-[1,2,4]triazolo[1,5-a]pyridine; | 9.1 |
| 29 | 7-Methoxy-8-(7-methyl-1H-indazol-5-yl)-2-(trifluoromethyl)-[1,2,4]triazolo[1,5-a]pyridine; | 7.6 |
| 30 | 8-(7-Chloro-1H-indazol-5-yl)-2-cyclopropyl-7-(trifluoromethyl)-[1,2,4]triazolo[1,5-a]pyridine; | 9.8 |
| 31 | 2-Cyclopropyl-8-(7-methyl-1H-indazol-5-yl)-7-(trifluoromethyl)-[1,2,4]triazolo[1,5-a]pyridine; | 9.7 |
| 32 | 8-(7-Chloro-1H-indazol-5-yl)-2-methyl-7-(trifluoromethyl)-[1,2,4]triazolo[1,5-a]pyridine; | 8.3 |

TABLE 4-continued

| Ex # | Compound Name | pIC50 |
|---|---|---|
| 33 | 2-Methyl-8-(7-methyl-1H-indazol-5-yl)-7-(trifluoromethyl)-[1,2,4]triazolo[1,5-a]pyridine; | 7.9 |
| 34 | 8-(7-Chloro-1H-indazol-5-yl)-2-ethyl-7-(trifluoromethyl)-[1,2,4]triazolo[1,5-a]pyridine; | 9.4 |
| 35 | 2-Ethyl-8-(7-methyl-1H-indazol-5-yl)-7-(trifluoromethyl)-[1,2,4]triazolo[1,5-a]pyridine; | 8.8 |
| 36 | 5-[2-Ethyl-7-(trifluoromethyl)-[1,2,4]triazolo[1,5-a]pyridin-8-yl]-7-methyl-indolin-2-one; | 8.7 |
| 37 | 8-(7-Chloro-1H-indazol-5-yl)-2-isopropyl-7-(trifluoromethyl)-[1,2,4]triazolo[1,5-a]pyridine; | 9.9 |
| 38 | 2-Isopropyl-8-(7-methyl-1H-indazol-5-yl)-7-(trifluoromethyl)-[1,2,4]triazolo[1,5-a]pyridine; | 8.7 |
| 39 | 5-[2-Isopropyl-7-(trifluoromethyl)-[1,2,4]triazolo[1,5-a]pyridin-8-yl]-7-methyl-indolin-2-one; | 9.2 |
| 40 | 2-Isopropyl-7-methyl-8-(7-methyl-1H-indazol-5-yl)-[1,2,4]triazolo[1,5-a]pyridine; | 6.9 |
| 41 | 7-Chloro-8-(7-chloro-1H-indazol-5-yl)-2-(trifluoromethyl)-[1,2,4]triazolo[1,5-a]pyridine; | 9.0 |
| 42 | 7-(4-Fluorophenyl)-8-(7-fluoro-1H-indazol-5-yl)-2-(trifluoromethyl)-[1,2,4]triazolo[1,5-a]pyridine; | 9.0 |
| 43 | 7-(4-Fluorophenyl)-8-(7-chloro-1H-indazol-5-yl)-2-(trifluoromethyl)-[1,2,4]triazolo[1,5-a]pyridine; | 11.0 |
| 44 | 7-(4-Fluorophenyl)-8-(7-methyl-1H-indazol-5-yl)-2-(trifluoromethyl)-[1,2,4]triazolo[1,5-a]pyridine; | 10.5 |
| 45 | 8-(3-Fluoro-1H-indazol-5-yl)-7-(4-fluorophenyl)-2-(trifluoromethyl)-[1,2,4]triazolo[1,5-a]pyridine; | 7.6 |
| 46 | 2-(Difluoromethyl)-7-(4-fluorophenyl)-8-(7-methyl-1H-indazol-5-yl)-[1,2,4]triazolo[1,5-a]pyridine; | 10.5 |
| 47 | 7-(4-Fluorophenyl)-2-(methoxymethyl)-8-(7-methyl-1H-indazol-5-yl)-[1,2,4]triazolo[1,5-a]pyridine; | 8.7 |
| 48 | 2-Cyclopropyl-7-(4-fluorophenyl)-8-(7-methyl-1H-indazol-5-yl)-[1,2,4]triazolo[1,5-a]pyridine; | 10.1 |
| 49 | 7-Isopropyl-8-(7-methyl-1H-indazol-5-yl)-2-(trifluoromethyl)-[1,2,4]triazolo[1,5-a]pyridine; | 10.5 |
| 50 | 8-(1H-Indazol-5-yl)-7-methyl-2-(trifluoromethyl)imidazo[1,2-a]pyridine; | 7.2 |
| 51 | 7-Fluoro-5-[7-methyl-2-(trifluoromethyl)imidazo[1,2-a]pyridin-8-yl]indolin-2-one; | 7.2 |
| 52 | 7-Methyl-8-(7-methyl-1H-indazol-5-yl)-2-(trifluoromethyl)imidazo[1,2-a]pyridine; | 8.0 |
| 53 | 2-tert-Butyl-7-methyl-8-(7-methyl-1H-indazol-5-yl)imidazo[1,2-a]pyridine; | 7.5 |
| 54 | 5-(2-tert-Butyl-7-methyl-imidazo[1,2-a]pyridin-8-yl)-7-methyl-indolin-2-one; | 7.1 |
| 55 | 7-Methyl-5-(7-methyl-2-phenyl-imidazo[1,2-a]pyridin-8-yl)indolin-2-one; | 7.4 |
| 56 | 7-Methyl-8-(7-methyl-1H-indazol-5-yl)-2-phenyl-imidazo[1,2-a]pyridine; | 7.9 |
| 57 | 2-Cyclopropyl-7-methyl-8-(7-methyl-1H-indazol-5-yl)imidazo[1,2-a]pyridine; | 7.6 |
| 58 | 5-[7-Methoxy-2-(trifluoromethyl)imidazo[1,2-a]pyridin-8-yl]-7-methyl-indolin-2-one; | 7.8 |
| 59 | 7-Methoxy-8-(7-methyl-1H-indazol-5-yl)-2-(trifluoromethyl)imidazo[1,2-a]pyridine; | 8.1 |
| 60 | 7-Chloro-8-(7-methyl-1H-indazol-5-yl)-2-(trifluoromethyl)imidazo[1,2-a]pyridine; | 9.0 |
| 61 | 5-(2,7-Bis(trifluoromethyl)imidazo[1,2-a]pyridin-8-yl)-1H-indazole; | 7.5 |
| 62 | 5-(2,7-Bis(trifluoromethyl)imidazo[1,2-a]pyridin-8-yl)-7-methyl-1H-indazole; | 9.5 |
| 63 | 8-(7-Methyl-1H-indazol-5-yl)-2,7-bis(trifluoromethyl)imidazo[1,2-c]pyrimidine; | 8.9 |
| 64 | 8-(7-Chloro-1H-indazol-5-yl)-2-ethyl-7-(trifluoromethyl)imidazo[1,2-c]pyrimidine; | 9.3 |
| 65 | 2-Ethyl-8-(7-methyl-1H-indazol-5-yl)-7-(trifluoromethyl)imidazo[1,2-c]pyrimidine; | 8.8 |
| 66 | 8-(7-Chloro-1H-indazol-5-yl)-2-isopropyl-7-(trifluoromethyl)imidazo[1,2-c]pyrimidine; | 10.0 |
| 67 | 8-(7-Chloro-1H-indazol-5-yl)-2-cyclopropyl-7-(trifluoromethyl)imidazo[1,2-c]pyrimidine; | 9.9 |
| 68 | 2-Cyclopropyl-8-(7-methyl-1H-indazol-5-yl)-7-(trifluoromethyl)imidazo[1,2-c]pyrimidine; | 9.6 |
| 69 | 7-Chloro-5-[2-cyclopropyl-7-(trifluoromethyl)imidazo[1,2-c]pyrimidin-8-yl]indolin-2-one; | 9.5 |
| 70 | 5-[2-Cyclopropyl-7-(trifluoromethyl)imidazo[1,2-c]pyrimidin-8-yl]-7-fluoro-indolin-2-one; | 5.3 |
| 71 | 8-(7-Chloro-1H-indazol-5-yl)-7-isopropyl-2-(trifluoromethyl)imidazo[1,2-c]pyrimidine; | 9.8 |

TABLE 4-continued

| Ex # | Compound Name | pIC50 |
|---|---|---|
| 72 | 8-(7-Chloro-1H-indazol-5-yl)-2-(difluoromethyl)-7-isopropyl-imidazo[1,2-c]pyrimidine; | 9.5 |
| 73 | 8-(7-Chloro-1H-indazol-5-yl)-7-ethyl-2-(trifluoromethyl)imidazo[1,2-c]pyrimidine; | 9.1 |
| 74 | 7-Ethyl-8-(7-methyl-1H-indazol-5-yl)-2-(trifluoromethyl)imidazo[1,2-c]pyrimidine; | 8.7 |
| 75 | 8-(7-Chloro-1H-indazol-5-yl)-2-(difluoromethyl)-7-ethyl-imidazo[1,2-c]pyrimidine; | 8.9 |
| 76 | 8-(7-Chloro-1H-indazol-5-yl)-7-methyl-2-(trifluoromethyl)imidazo[1,2-c]pyrimidine; | 8.5 |
| 77 | 8-(7-Chloro-1H-indazol-5-yl)-7-cyclopropyl-2-(trifluoromethyl)imidazo[1,2-c]pyrimidine; | 9.0 |
| 78 | 8-(7-Chloro-1H-indazol-5-yl)-7-cyclopropyl-2-(difluoromethyl)imidazo[1,2-c]pyrimidine; | 8.6 |
| 79 | 8-(7-Chloro-1H-indazol-5-yl)-7-cyclopropyl-5-methyl-2-trifluoromethyl)imidazo[1,2-c]pyrimidine; | 8.9 |
| 80 | 8-(7-Chloro-1H-indazol-5-yl)-7-cyclopropyl-2-(difluoromethyl)-5-methyl-imidazo[1,2-c]pyrimidine; | 9.2 |
| 81 | 3-Chloro-8-(7-chloro-1H-indazol-5-yl)-2-cyclopropyl-7-(trifluoromethyl)imidazo[1,2-c]pyrimidine; | 9.9 |
| 82 | 8-(7-Chloro-1H-indazol-5-yl)-2-cyclopropyl-3-fluoro-7-(trifluoromethyl)imidazo[1,2-c]pyrimidine; | 9.5 |
| 86 | 5-(2,7-Bis(trifluoromethyl)imidazo[1,2-a]pyridin-8-yl)-7-chloroindolin-2-one; | 9.8 |
| 87 | 5-(2,7-Bis(trifluoromethyl)imidazo[1,2-a]pyridin-8-yl)-7-methylindolin-2-one; | 9.4 |
| 88 | 5-(2,7-Bis(trifluoromethyl)imidazo[1,2-a]pyridin-8-yl)-7-chloro-1H-indazole; | 10.3 |
| 89 | 8-(7-Chloro-1H-indazol-5-yl)-2-isopropyl-7-(trifluoromethyl)imidazo[1,2-a]pyridine; | 10.6 |
| 90 | 2-Isopropyl-8-(7-methyl-1H-indazol-5-yl)-7-(trifluoromethyl)imidazo[1,2-a]pyridine; | 10.0 |
| 91 | 2-Cyclopropyl-8-(7-methyl-1H-indazol-5-yl)-7-(trifluoromethyl)imidazo[1,2-a]pyridine; | 9.6 |
| 92 | 2-Ethyl-8-(7-methyl-1H-indazol-5-yl)-7-(trifluoromethyl)imidazo[1,2-a]pyridine; | 9.4 |
| 93 | 2-(Difluoromethyl)-8-(7-methyl-1H-indazol-5-yl)-7-(trifluoromethyl)imidazo[1,2-a]pyridine; and | 9.3 |
| 94 | 2-Methyl-8-(7-methyl-1H-indazol-5-yl)-7-(trifluoromethyl)imidazo[1,2-a]pyridine. | 8.1 |

Electrophysiology Assay

The effects of selected compounds upon endogenous gamma8-containing AMPA receptor currents are evaluated using whole-cell electrophysiology on acutely-dissociated mouse hippocampal neurons. Hippocampus was chosen for this assay, since CACNG8 (the protein encoded by this gene is a type I transmembrane AMPA receptor regulatory protein i.e., TARP) is preferentially enriched in this brain region (Tomita et al. (2003). "Functional studies and distribution define a family of transmembrane AMPA receptor regulatory proteins." *J Cell Biol* 161(4): 805-816.2003). Hippocampi are dissected from C57black6 mice at 4-12 weeks postnatal, following the protocol described by Brewer (Brewer, G. J. (1997). "Isolation and culture of adult rat hippocampal neurons." *Journal of Neuroscience Methods* 71(2): 143-155). The following is a brief summary of the procedure. Mice are asphyxiated with $CO_2$ then decapitated. The brain is rapidly removed, then placed into ice-cold HABG medium. The recipe for HABG medium is: HibernateA supplemented with 2% B27 and 0.5 mM Glutamax (all reagents from Life Technologies). Hippocampi are micro-dissected from the brains, then washed with HABG without calcium (Hibernate A minus Calcium, BrainBits; 2% B27, Life Technologies; 0.5 mM glutamax, Life Technologies).

The hippocampi are then transferred to HABG without calcium, supplemented with 2 mg/mL papain (Worthington Biochemical). They are incubated at 30° C. on a roller for 40 min, then gently triturated with a fire-polished glass pipette. The supernatant containing dissociated neurons is collected, then centrifuged for 2 min at 200 g. The cell pellet is collected, and then resuspended in 8 mL of HABG. Live cells are counted, then plated onto 12 mm glass coverslips in 2 mL of HABG in 24-well plates at a density of 50-100 cells per coverslip. These cells are maintained at rt until use. Whole-cell electrophysiology is performed using 1.5 mm diameter glass capillary tubes (World Precision Instruments TW150-4), pulled to a fine tip with a Sutter P-97 micropipette puller. The intracellular buffer was 90 mM KF, 30 mM KCl, 10 mM HEPES, and 5 mM EGTA, pH 7.4, 290 mOs. The extracellular buffer was 135 mM NaCl, 4 mM KCl, 2 mM $CaCl_2$, 1 mM $MgCl_2$, 5 mM glucose, 10 mM HEPES, pH 7.4, 300 mOs. The open-tip resistances of the micropipettes using these solutions are 2-4 MΩ. Whole-cell recordings of neuron cell bodies are performed in voltage-clamp mode using an Axon Axopatch 200B amplifier. Whole-cell current is measured holding the interior of the cell at −60 mV, using a 5 kHz lowpass filter. The cells are continuously perfused through 7 mm square glass barrels using a solenoid-controlled solution switching device (Warner Instruments, PF-77B). The peak current in response to a 500 ms exposure to 10 mM glutamate every 5 seconds is measured, before and after exposure to test compound.

For analysis, the mean peak current of 5 traces in the presence of test compound is divided by the mean peak current of 5 traces prior to the addition of test compound. Compounds are tested at concentrations at least ten times higher than their estimated potency in the calcium flux assay, in order to ensure near-saturating occupancy of the receptor.

All patents, patent applications, publications and presentations referred to herein are incorporated by reference in their entirety.

Any combination of the groups described above for the various variables is contemplated herein. Throughout the specification, groups and substituents thereof are chosen by one skilled in the field to provide stable moieties and compounds.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula (I):

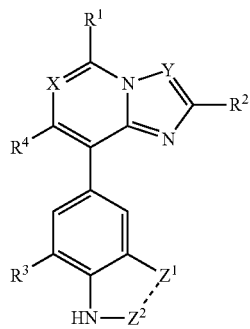

(I)

wherein
X is N or CH;
Y is selected from the group consisting of: N, CH, CF, and CCl;
$R^1$ is H or $CH_3$;
$R^2$ is selected from the group consisting of: $C_{1-6}$alkyl, $C_{1-6}$haloalkyl, $CH_2OCH_3$, $C_{3-8}$cycloalkyl and phenyl;
$R^3$ is selected from the group consisting of: H, halo, $CH_3$, and $CF_3$;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

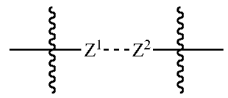

is selected from the group consisting of: —CH=N—; —CF=N—; —CH$_2$—C(=O)—; and —S—C(=O)—; and pharmaceutically acceptable salts, N-oxides, or solvates thereof.

2. The compound of claim 1, wherein X is N.
3. The compound of claim 1, wherein X is CH.
4. The compound of claim 1, wherein Y is N.
5. The compound of claim 1, wherein Y is CH, CF, or CCl.
6. The compound of claim 1, wherein Y is CH.
7. The compound of claim 1, wherein $R^1$ is H.
8. The compound of claim 1, wherein $R^1$ is $CH_3$.

9. The compound of claim 1, wherein $R^2$ is $C_{1-6}$alkyl, $C_{1-6}$haloalkyl, $CH_2OCH_3$, cyclopropyl, cyclobutyl, cyclopentyl, or phenyl.
10. The compound of claim 1, wherein $R^2$ is $CH_3$, $CH_2CH_3$, $CH(CH_3)_2$, $C(CH_3)_3$, $CF_2H$, $CF_3$.
11. The compound of claim 1, wherein $R^2$ is $CF_3$.
12. The compound of claim 1, wherein $R^3$ is H, F, Cl, or $CH_3$.
13. The compound of claim 1, wherein $R^4$ is $C_{1-6}$alkyl, $C_{1-6}$haloalkyl, Cl, CN, $OCH_3$, phenyl substituted with F, cyclopropyl, cyclopentyl, azetidinyl, or azetidinyl substituted with F.
14. The compound of claim 1, wherein $R^4$ is $CF_3$.
15. The compound of claim 1, wherein

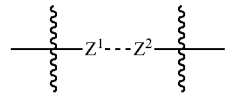

is —CH=N—.

16. The compound of claim 1, wherein

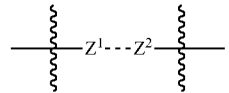

is $CH_2$—C(=O)—.

17. The compound of claim 1, and pharmaceutically acceptable salts, solvates, or N-oxides thereof, having the structure of Formula (1A):

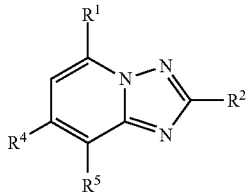

(IA)

wherein
$R^1$ is H;
$R^2$ is selected from the group consisting of: $C_{1-6}$alkyl, $C_{1-6}$haloalkyl, $CH_2OCH_3$, and $C_{3-8}$cycloalkyl;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and
$R^5$ is selected from the group consisting of:

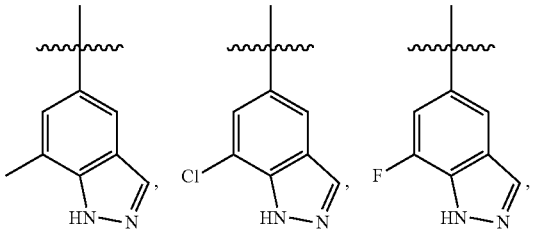

-continued

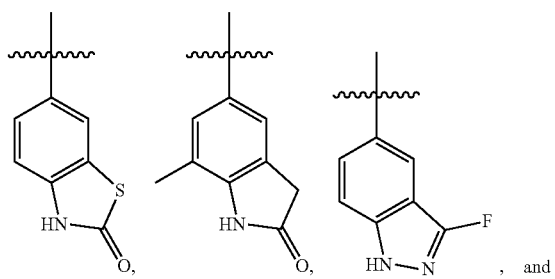

, and

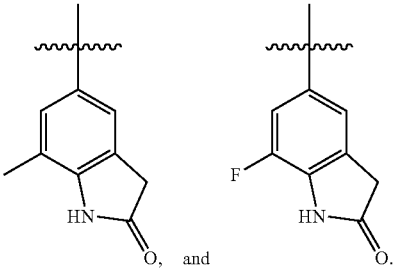

and

19. The compound of claim 1, and pharmaceutically acceptable salts, solvates, or N—oxides thereof, having the structure of Formula (1C):

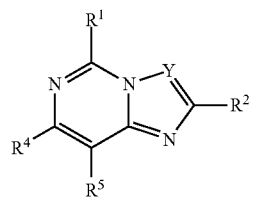

(IC)

wherein

Y is selected from the group consisting of: CH, CF, and CCl;

$R^1$ is H or $CH_3$;

$R^2$ is selected from the group consisting of: $C_{1-6}$alkyl, $C_{1-6}$haloalkyl, $CH_2OCH_3$, $C_{3-8}$cycloalkyl and phenyl;

$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and $R^5$ is selected from the group consisting of:

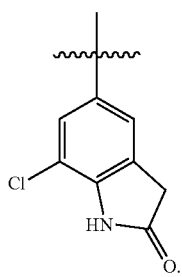

18. The compound of claim 1, and pharmaceutically acceptable salts, solvates, or N—oxides thereof, having the structure of Formula (1B):

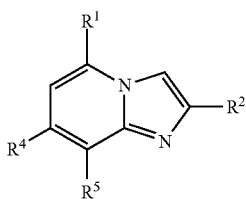

(IB)

wherein $R^1$ is H;

$R^2$ is selected from the group consisting of: $C_{1-6}$alkyl, $C_{1-6}$haloalkyl, $CH_2OCH_3$, $C_{3-8}$cycloalkyl and phenyl;

$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and $R^5$ is selected from the group consisting of:

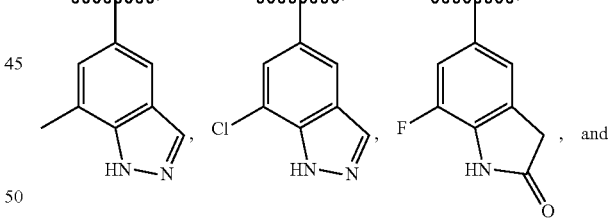

, and

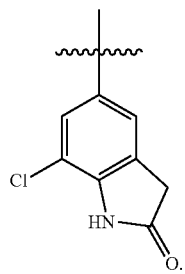

20. A compound selected from the group consisting of:
8-(7-Chloro-1H-indazol-5-yl)-2-(difluoromethyl)-7-(trifluoromethyl)-[1,2,4]triazolo[1,5-a]pyridine;
7-Chloro-8-(7-methyl-1H-indazol-5-yl)-2-(trifluoromethyl)-[1,2,4]triazolo[1,5-a]pyridine;

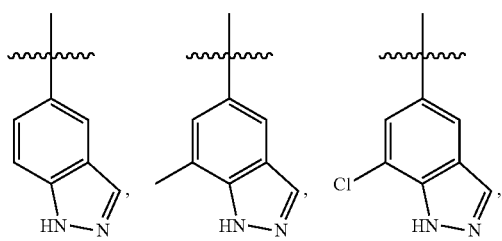

6-(2,7-Bis(trifluoromethyl)-[1,2,4]triazolo[1,5-a]pyridin-8-yl)benzo[d]thiazol-2(3H)-one;
2-Cyclobutyl-7-(4-fluorophenyl)-8-(7-methyl-1H-indazol-5-yl)-[1,2,4]triazolo[1,5-a]pyridine;
6-(7-(4-Fluorophenyl)-2-(trifluoromethyl)-[1,2,4]triazolo[1,5-a]pyridin-8-yl)benzo[d]thiazol-2(3H)-one;
7-Cyclopentyl-8-(7-methyl-1H-indazol-5-yl)-2-(trifluoromethyl)-[1,2,4]triazolo[1,5-a]pyridine;
7-(Azetidin-1-yl)-8-(7-methyl-1H-indazol-5-yl)-2-(trifluoromethyl)-[1,2,4]triazolo[1,5-a]pyridine;
7-(3-Fluoroazetidin-1-yl)-8-(7-methyl-1H-indazol-5-yl)-2-(trifluoromethyl)-[1,2,4]triazolo[1,5-a]pyridine;
2-Cyclopentyl-7-(4-fluorophenyl)-8-(7-methyl-1H-indazol-5-yl)-[1,2,4]triazolo[1,5-a]pyridine;
8-(7-Methyl-1H-indazol-5-yl)-2-(trifluoromethyl)-[1,2,4]triazolo[1,5-a]pyridine-7-carbonitrile;
7-Methyl-5-[7-methyl-2-(trifluoromethyl)imidazo[1,2-a]pyridin-8-yl]indolin-2-one;
5-(7-(4-Fluorophenyl)-2-(trifluoromethyl)imidazo[1,2-a]pyridin-8-yl)-1H-indazole;
8-(7-Chloro-1H-indazol-5-yl)-2,7-bis(trifluoromethyl)imidazo[1,2-c]pyrimidine;
8-(7-Chloro-1H-indazol-5-yl)-2-(difluoromethyl)-7-(trifluoromethyl)imidazo[1,2-c]pyrimidine;
2-(Difluoromethyl)-8-(7-methyl-1H-indazol-5-yl)-7-(trifluoromethyl)imidazo[1,2-c]pyrimidine;
8-(7-Methyl-1H-indazol-5-yl)-2-(difluoromethyl)-7-(trifluoromethyl)-[1,2,4]triazolo[1,5-a]pyridine;
7-Chloro-5-(2-(difluoromethyl)-7-(trifluoromethyl)-[1,2,4]triazolo[1,5-a]pyridin-8-yl)indolin-2-one;
7-Methyl-5-(2-(difluoromethyl)-7-(trifluoromethyl)-[1,2,4]triazolo[1,5-a]pyridin-8-yl)indolin-2-one;
8-(7-Chloro-1H-indazol-5-yl)-2,7-bis(trifluoromethyl)-[1,2,4]triazolo[1,5-a]pyridine;
8-(7-Methyl-1H-indazol-5-yl)-2,7-bis(trifluoromethyl)-[1,2,4]triazolo[1,5-a]pyridine;
5-(2,7-Bis(trifluoromethyl)-[1,2,4]triazolo[1,5-a]pyridin-8-yl)-7-chloroindolin-2-one;
5-(2,7-Bis(trifluoromethyl)-[1,2,4]triazolo[1,5-a]pyridin-8-yl)-7-methylindolin-2-one;
8-(7-Chloro-1H-indazol-5-yl)-7-(difluoromethyl)-2-(trifluoromethyl)-[1,2,4]triazolo[1,5-a]pyridine;
8-(7-Methyl-1H-indazol-5-yl)-7-(difluoromethyl)-2-(trifluoromethyl)-[1,2,4]triazolo[1,5-a]pyridine;
7-Chloro-5-(7-(difluoromethyl)-2-(trifluoromethyl)-[1,2,4]triazolo[1,5-a]pyridin-8-yl)indolin-2-one;
7-Methyl-5-(7-(difluoromethyl)-2-(trifluoromethyl)-[1,2,4]triazolo[1,5-a]pyridin-8-yl)indolin-2-one;
7-Methyl-8-(7-methyl-1H-indazol-5-yl)-2-(trifluoromethyl)-[1,2,4]triazolo[1,5-a]pyridine;
7-Ethyl-8-(7-methyl-1H-indazol-5-yl)-2-(trifluoromethyl)-[1,2,4]triazolo[1,5-a]pyridine;
7-Methoxy-8-(7-methyl-1H-indazol-5-yl)-2-(trifluoromethyl)-[1,2,4]triazolo[1,5-a]pyridine;
8-(7-Chloro-1H-indazol-5-yl)-2-cyclopropyl-7-(trifluoromethyl)-[1,2,4]triazolo[1,5-a]pyridine;
2-Cyclopropyl-8-(7-methyl-1H-indazol-5-yl)-7-(trifluoromethyl)-[1,2,4]triazolo[1,5-a]pyridine;
8-(7-Choro-1H-indazol-5-yl)-2-methyl-7-(trifluoromethyl)-[1,2,4]triazolo[1,5-a]pyridine;
2-Methyl-8-(7-methyl-1H-indazol-5-yl)-7-(trifluoromethyl)-[1,2,4]triazolo[1,5-a]pyridine;
8-(7-Chloro-1H-indazol-5-yl)-2-ethyl-7-(trifluoromethyl)-[1,2,4]triazolo[1,5-a]pyridine;
2-Ethyl-8-(7-methyl-1H-indazol-5-yl)-7-(trifluoromethyl)-[1,2,4]triazolo[1,5-a]pyridine;

5-[2-Ethyl-7-(trifluoromethyl)-[1,2,4]triazolo[1,5-a]pyridin-8-yl]-7-methyl-indolin-2-one;
8-(7-Chloro-1H-indazol-5-yl)-2-isopropyl-7-(trifluoromethyl)-[1,2,4]triazolo[1,5-a]pyridine;
2-Isopropyl-8-(7-methyl-1H-indazol-5-yl)-7-(trifluoromethyl)-[1,2,4]triazolo[1,5-a]pyridine;
5-[2-Isopropyl-7-(trifluoromethyl)-[1,2,4]triazolo[1,5-a]pyridin-8-yl]-7-methyl-indolin-2-one;
2-Isopropyl-7-methyl-8-(7-methyl-1H-indazol-5-yl)-[1,2,4]triazolo[1,5-a]pyridine;
7-Chloro-8-(7-chloro-1H-indazol-5-yl)-2-(trifluoromethyl)-[1,2,4]triazolo[1,5-a]pyridine;
7-(4-Fluorophenyl)-8-(7-fluoro-1H-indazol-5-yl)-2-(trifluoromethyl)-[1,2,4]triazolo[1,5-a]pyridine;
7-(4-Fluorophenyl)-8-(7-chloro-1H-indazol-5-yl)-2-(trifluoromethyl)[1,2,4]triazolo[1,5-a]pyridine;
7-(4-Fluorophenyl)-8-(7-methyl-1H-indazol-5-yl)-2-(trifluoromethyl)-[1,2,4]triazolo[1,5-a]pyridine;
8-(3-Fluoro-1H-indazol-5-yl)-7-(4-fluorophenyl)-2-(trifluoromethyl)-[1,2,4]triazolo[1,5-a]pyridine;
2-(Difluoromethyl)-7-(4-fluorophenyl)-8-(7-methyl-1H-indazol-5-yl)-[1,2,4]triazolo[1,5-a]pyridine;
7-(4-Fluorophenyl)-2-(methoxymethyl)-8-(7-methyl-1H-indazol-5-yl)-[1,2,4]triazolo[1,5-a]pyridine;
2-Cyclopropyl-7-(4-fluorophenyl)-8-(7-methyl- 1H-indazol-5-yl)-[1,2,4]triazolo[1,5-a]pyridine;
7-Isopropyl-8-(7-methyl-1H-indazol-5-yl)-2-(trifluoromethyl)-[1,2,4]triazolo[1,5-a]pyridine;
8-(1H-Indazol-5-yl)-7-methyl-2-(trifluoromethyl)imidazo[1,2-a]pyridine;
7-Fluoro-5-[7-methyl-2-(trifluoromethyl)imidazo[1,2-a]pyridin-8-yl]indolin-2-one;
7-Methyl-8-(7-methyl-1H-indazol-5-yl)-2-(trifluoromethyl)imidazo[1,2-a]pyridine;
2-tert-Butyl-7-methyl-8-(7-methyl-1H-indazol-5-yl)imidazo[1,2-a]pyridine;
5-(2-tert-Butyl-7-methyl-imidazo[1,2-a]pyridin-8-yl)-7-methyl-indolin-2-one;
7-Methyl-5-(7-methyl-2-phenyl-imidazo[1,2-a]pyridin-8-yl)indolin-2-one;
7-Methyl-8-(7-methyl- 1H-indazol-5-yl)-2-phenyl-imidazo[1,2-a]pyridine;
2-Cyclopropyl-7-methyl-8-(7-methyl- 1H-indazol-5-yl)imidazo[1,2-a]pyridine;
5-[7-Methoxy-2-(trifluoromethyl)imidazo[1,2-a]pyridin-8-yl]-7-methyl-indolin-2-one;
7-Methoxy-8-(7-methyl- 1H-indazol-5-yl)-2-(trifluoromethyl)imidazo[1,2-a]pyridine;
7-Chloro-8-(7-methyl- 1H-indazol-5-yl)-2-(trifluoromethyl)imidazo[1,2-a]pyridine;
5-(2,7-Bis(trifluoromethyl)imidazo[1,2-a]pyridin-8-yl)-1H-indazole;
5-(2,7-Bis(trifluoromethyl)imidazo[1,2-a]pyridin-8-yl)-7-methyl-1H-indazole;
8-(7-Methyl-1H-indazol-5-yl)-2,7-bis(trifluoromethyl)imidazo[1,2-c]pyrimidine;
8-(7-Chloro- 1H-indazol-5-yl)-2-ethyl-7-(trifluoromethyl)imidazo[1,2-c]pyrimidine;
2-Ethyl-8-(7-methyl-1H-indazol-5-yl)-7-(trifluoromethyl)imidazo[1,2-c]pyrimidine;
8-(7-Chloro-1H-indazol-5-yl)-2-isopropyl-7-(trifluoromethyl)imidazo[1,2-c]pyrimidine;
8-(7-Chloro-1H-indazol-5-yl)-2-cyclopropyl-7-(trifluoromethyl)imidazo[1,2-c]pyrimidine;
2-Cyclopropyl-8-(7-methyl-1H-indazol-5-yl)-7-(trifluoromethyl)imidazo[1,2-c]pyrimidine;

7-Chloro-5-[2-cyclopropyl-7-(trifluoromethyl)imidazo[1,2-c]pyrimidin-8-yl]indolin-2-one;

5-[2-Cyclopropyl-7-(trifluoromethyl)imidazo[1,2-c]pyrimidin-8-yl]-7-fluoro-indolin-2-one;

8-(7-Chloro-1H-indazol-5-yl)-7-isopropyl-2-(trifluoromethyl)imidazo[1,2-c]pyrimidine;

8-(7-Chloro-1H-indazol-5-yl)-2-(difluoromethyl)-7-isopropyl-imidazo[1,2-c]pyrimidine;

8-(7-Chloro-1H-indazol-5-yl)-7-ethyl-2-(trifluoromethyl)imidazo[1,2-c]pyrimidine;

7-Ethyl-8-(7-methyl-1H-indazol-5-yl)-2-(trifluoromethyl)imidazo[1,2-c]pyrimidine;

8-(7-Chloro-1H-indazol-5-yl)-2-(difluoromethyl)-7-ethyl-imidazo[1,2-c]pyrimidine;

8-(7-Chloro-1H-indazol-5-yl)-7-methyl-2-(trifluoromethyl)imidazo[1,2-c]pyrimidine;

8-(7-Chloro-1H-indazol-5-yl)-7-cyclopropyl-2-(trifluoromethyl)imidazo[1,2-c]pyrimidine;

8-(7-Chloro-1H-indazol-5-yl)-7-cyclopropyl-2-(difluoromethyl)imidazo[1,2-c]pyrimidine;

8-(7-Chloro-1H-indazol-5-yl)-7-cyclopropyl-5-methyl-2-trifluoromethyl)imidazo[1,2-c]pyrimidine;

8-(7-Chloro-1H-indazol-5-yl)-7-cyclopropyl-2-(difluoromethyl)-5-methyl-imidazo[1,2-c]pyrimidine;

3-Chloro-8-(7-chloro-1H-indazol-5-yl)-2-cyclopropyl-7-(trifluoromethyl)imidazo[1,2-c]pyrimidine; and 8-(7-Chloro-1H-indazol-5-yl)-2-cyclopropyl-3-fluoro-7-(trifluoromethyl)imidazo[1,2-c]pyrimidine;

5-(2,7-Bis(trifluoromethyl)imidazo[1,2-a]pyridin-8-yl)-7-chloroindolin-2-one;

5-(2,7-Bis(trifluoromethyl)imidazo[1,2-a]pyridin-8-yl)-7-methylindolin-2-one;

5-(2,7-Bis(trifluoromethyl)imidazo[1,2-a]pyridin-8-yl)-7-chloro-1H-indazole;

8-(7-Chloro-1H-indazol-5-yl)-2-isopropyl-7-(trifluoromethyl)imidazo[1,2-a]pyridine;

2-Isopropyl-8-(7-methyl-1H-indazol-5-yl)-7-(trifluoromethyl)imidazo[1,2-a]pyridine;

2-Cyclopropyl-8-(7-methyl-1H-indazol-5-yl)-7-(trifluoromethyl)imidazo[1,2-a]pyridine;

2-Ethyl-8-(7-methyl-1H-indazol-5-yl)-7-(trifluoromethyl)imidazo[1,2-a]pyridine;

2-(Difluoromethyl)-8-(7-methyl-1H-indazol-5-yl)-7-(trifluoromethyl)imidazo[1,2-a]pyridine; and 2-Methyl-8-(7-methyl-1H-indazol-5-yl)-7-(trifluoromethyl)imidazo[1,2-a]pyridine; and pharmaceutically acceptable salts, N-oxides or solvates thereof.

21. A compound selected from the group consisting of:

7-Cyclopropyl-2-(difluoromethyl)-5-methyl-8-(7-(trifluoromethyl)-1H-indazol-5-yl)imidazo[1,2-c]pyrimidine;

8-(7-Chloro-1H-indazol-5-yl)-7-(difluoromethyl)-2-ethyl-[1,2,4]triazolo[1,5-a]pyridine; and 8-(7-chloro-1H-indazol-5-yl)-2-cyclopropyl-7-(difluoromethyl)-[1,2,4]triazolo[1,5-a]pyridine; and pharmaceutically acceptable salts, N-oxides or solvates thereof.

22. A pharmaceutical composition comprising:
(A) an effective amount of at least one compound of Formula (I):

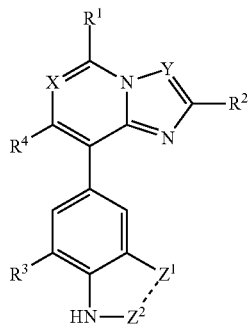

(I)

wherein
X is N or CH;
Y is selected from the group consisting of: N, CH, CF, or CCl;
$R^1$ is H or $CH_3$;
$R^2$ is selected from the group consisting of: $C_{1-6}$alkyl, $C_{1-6}$haloalkyl, $CH_2OCH_3$, $C_{3-8}$cycloalkyl and phenyl;
$R^3$ is selected from the group consisting of: H, halo, $CH_3$, and $CF_3$;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

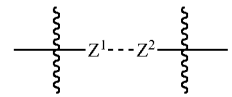

is selected from the group consisting of: —CH=N—; —CF=N—; —CH$_2$—C(=O)—; and —S—C(=O)—; and pharmaceutically acceptable salts, N-oxides or solvates of compounds of Formula (I); and (B) at least one pharmaceutically acceptable excipient.

23. A pharmaceutical composition comprising an effective amount of at least one compound of claim 21 and at least one pharmaceutically acceptable excipient.

24. A method of treating a subject suffering from or diagnosed with a disease, disorder, or medical condition mediated by AMPA receptor activity, comprising administering to a subject in need of such treatment an effective amount of at least one compound of Formula (I):

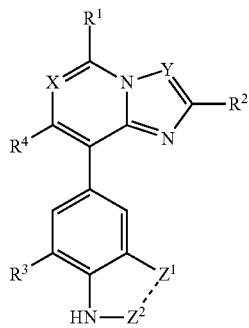

(I)

wherein
X is N or CH;
Y is selected from the group consisting of: N, CH, CF, and CCl;
$R^1$ is H or $CH_3$;
$R^2$ is selected from the group consisting of: $C_{1-6}$alkyl, $C_{1-6}$haloalkyl, $CH_2OCH_3$, $C_{3-8}$cycloalkyl and phenyl;
$R^3$ is selected from the group consisting of: H, halo, $CH_3$, and $CF_3$;
$R^4$ is selected from the group consisting of: halo, $C_{1-6}$alkyl, $C_{1-6}$alkoxy, $C_{1-6}$haloalkyl, CN, $C_{3-8}$cycloalkyl, azetidinyl, azetidinyl substituted with F, and phenyl substituted with F; and

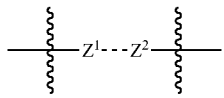

is selected from the group consisting of: —CH=N—; —CF=N—; —CH$_2$—C(=O)—; and —S—C(=O)—; and pharmaceutically acceptable salts, N-oxides or solvates of compounds of Formula (I).

25. The method of claim 24, wherein the AMPA receptor mediated disease, disorder, or medical condition is selected from cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, neurodegenerative diseases, chronic pain, migraine, cancer pain, diabetic neuropathy, encephalitis, acute disseminated encephalomyelitis, acute demyelinating polyneuropathy, chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder, schizophrenia, prodromal schizophrenia, cognitive disorder, depression, anxiety disorders, anxious depression, and bipolar disorder.

26. The method of claim 24, wherein the AMPA receptor mediated disease, disorder or condition is depression, post traumatic stress disorder, epilepsy, schizophrenia, prodromal schizophrenia, or a cognitive disorder.

* * * * *